(12) United States Patent
Walther et al.

(10) Patent No.: US 10,961,551 B2
(45) Date of Patent: *Mar. 30, 2021

(54) PROCESS FOR PRODUCING AT LEAST ONE METABOLITE OF INTEREST BY CONVERSION OF A PENTOSE IN A MICROORGANISM

(71) Applicants: INSTITUT NATIONAL DE LA RECHERCHE AGRONOMIQUE—INRA, Paris (FR); INSTITUT NATIONAL DES SCIENCES APPLIQUEES—INSA, Toulouse (FR); CENTRE NATIONAL DE LA RECHERCHE SCIENTIFIQUE, Paris (FR)

(72) Inventors: Thomas Walther, Lacroix-Falgarde (FR); Yvan Cam, Castanet-Tolosan (FR); Jean-Marie Francois, Plaisance du Touch (FR); Ceren Alkim, Toulouse (FR)

(73) Assignees: INSTITUT NATIONAL DE RECHERCHE POUR L'AGRICULTURE, L'ALIMENTATION ET L'ENVIRONMENT, Paris (FR); INSTITUT NATIONAL DES SCIENCES APPLIQUEES—INSA, Toulouse (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 16/671,683

(22) Filed: Nov. 1, 2019

(65) Prior Publication Data

US 2020/0063167 A1 Feb. 27, 2020

Related U.S. Application Data

(63) Continuation of application No. 15/526,444, filed as application No. PCT/FR2015/053138 on Nov. 19, 2015, now Pat. No. 10,570,423.

(30) Foreign Application Priority Data

Nov. 19, 2014 (FR) .................................. 1461183

(51) Int. Cl.
C12P 7/42 (2006.01)
C12P 7/18 (2006.01)

(52) U.S. Cl.
CPC .. *C12P 7/42* (2013.01); *C12P 7/18* (2013.01)

(58) Field of Classification Search
CPC .................... C12P 7/42; C12P 7/18
See application file for complete search history.

(56) References Cited

U.S. PATENT DOCUMENTS

| | | | |
|---|---|---|---|
| 7,195,891 B2* | 3/2007 | Yuan | C12Q 1/26 435/28 |
| 7,445,917 B2 | 11/2008 | Dicosimo et al. | |
| 9,394,549 B2 | 7/2016 | Nukui | |
| 9,994,876 B2* | 6/2018 | Stephanopoulos | C12Y 401/02017 |
| 10,570,423 B2* | 2/2020 | Walther | C12P 7/42 |
| 2009/0155867 A1 | 6/2009 | Soucaille | |
| 2012/0315682 A1 | 12/2012 | Dischert et al. | |
| 2015/0147794 A1* | 5/2015 | Chung | C12N 9/92 435/158 |

FOREIGN PATENT DOCUMENTS

| | | |
|---|---|---|
| EP | 2 025 759 | 2/2009 |
| EP | 2 025 760 | 2/2009 |
| WO | WO 2006/069110 | 6/2006 |
| WO | WO 2007/140816 | 12/2007 |
| WO | WO 2007/141336 | 12/2007 |
| WO | WO 2010/108909 | 9/2010 |
| WO | WO 2011/130378 | 10/2011 |
| WO | WO 2012/177983 | 12/2012 |
| WO | WO 2013/126721 | 8/2013 |

OTHER PUBLICATIONS

U.S. Appl. No. 15/526,444, filed May 12, 2017.
International Search Report issued in Application No. PCT/FR2015/053138, dated Feb. 3, 2016.
Badia, J., et al., "L-Lyxose Metabolism Employs the L-Rhamnose Pathway in Mutant Cells of *Escherichia coli* Adapted to Grow on L-Lyxose," Journal of Bateriology, vol. 173, No. 16, Aug. 1991, pp. 5144-5150.
Liu, H., et al., "Biosynthesis of Ehtylene Glycol in *Escherichia coli*," Applied Microbiology and Biotechnology, vol. 9, No. 8, Apr. 2013, pp. 3409-3417.

(Continued)

*Primary Examiner* — Ganapathirama Raghu
(74) *Attorney, Agent, or Firm* — Nixon & Vanderhye

(57) ABSTRACT

Disclosed is a process for producing at least one metabolite of interest by conversion of a pentose in a microorganism. The process includes at least: (i) an operation of culturing a recombinant microorganism expressing a synthetic pathway for pentose assimilation which includes at least the following steps: a) phosphorylation in position 1 of a pentose chosen from (D)-xylulose and/or (L)-ribulose, b) cleavage of the pentose-1-phosphate obtained at the end of step a), in order to obtain glycolaldehyde and dihydroxyacetone phosphate (DHAP), and (ii) an operation of recovering the at least one metabolite of interest obtained at the end of the culturing operation (i). Also disclosed is an associated microorganism.

1 Claim, 7 Drawing Sheets

Figure 1:
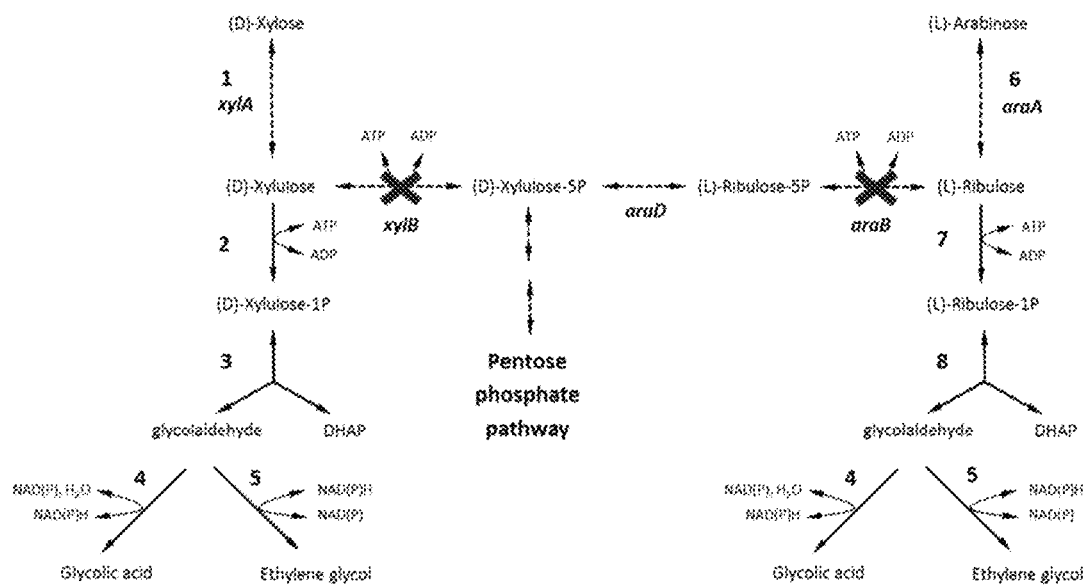

Specification includes a Sequence Listing.

(56) References Cited

OTHER PUBLICATIONS

James, H.M., et al., "Models for the Metabolic Production of Oxalate from Xylitol in Humans: A Role for Fructokinase and Aldolase," Aust. J. Exp. Biol. Med. Sci., vol. 60, 1982, pp. 117-122.
Asipu, A., et al., "Properties of Normal and Mutant Recombinant Human Ketohexokinases and Implications for the Pathogenesis of Essential Fructosuria," Diabetes, vol. 52, No. 9, Sep. 2003, pp. 2426-2432.
Baba, T., et al., "Construction of Escherichia coli K-12 In-Frame, Single-Gene Knockout Mutants: the Keio Collection," Molecular Systems Biology, 2006, pp. 1-11.
Bais, R., et al., "The Purification and Properties of Human Liver Ketohexokinase," Biochem. J., vol. 230, 1985, pp. 53-60.
Brat, D., et al., "Functional Expression of a Bacterial Xylose Isomerase in Saccharomyces cerevisiae," Applied and Environmental Microbiology, vol. 75, No. 8, Apr. 2009, pp. 2304-2311.
Cherepanov, P., et al., "Gene Disruption in Escherichia coli: TcR and KmR Cassettes with the Option of Flp-Catalyzed Excision of the Antibiotic-Resistance Determinant," Gene, vol. 158, 1995, pp. 9-14.
Dagert, M., et al., "Prolonged Incubation in Calcium Chloride Improves the Competence of Escherichia coli Cells," Gene, vol. 6, 1979, pp. 23-28.
Datsenko, K., et al., "One-Step Inactivation of Chromosomal Genes in Escherichia coli K-12 Using PCR Products," Proc. Natl. Acad. Sci, vol. 97, No. 12, Jun. 2000, pp. 6640-6645.
Davis, J., et al., "Design, Construction and Characterization of a Set of Insulated Bacterial Promoters," Nucleic Acids Research, vol. 39, No. 3, 2011, pp. 1131-1141.
Dykxhoorn, D., et al., "A Set of Compatible TAC Promoter Expression Vectors," Gene, vol. 177, 1996, pp. 133-136.
Eliasson, A., et al., "Anaerobic Xylose Fermentation by Recombinant Saccharomyces cerevisiae Carrying XYL1, XYL2, and XKS1 in Mineral Medium Chemostat Cultures," Applied and Environmental Microbiology, vol. 66, No. 8, Aug. 2000, pp. 3381-3386.
Gietz, R., et al., "Transformation of Yeast by Lithium Acetate/ Single-Stranded Carrier DNA/Polyethylene Glycol Method," Methods Enzymol, vol. 350, 2002, pp. 87-96.
Klamt, S., et al., "A Methodology for the Structural and Functional Analysis of Signaling and Regulatory Networks," BMC Bioinformatics, vol. 7, No. 56, 2006, pp. 1-26.

Lee, C., et al., "Glyoxal Detoxification in Escherichia coli K-12 by NADPH Dependent Aldo-Keto Reductases," Journal of Microbiology, vol. 51, No. 4, 2013, pp. 527-530.
Salis, H., "The Ribosome Binding Site Calculator," Methods Enzymol, vol. 498, pp. 19-42.
Winzeler, E., et al., "Functional Characterization of S. Cerevisiae Genome by Gene Deletion and Parallel Analysis," Science, vol. 285, Aug. 1999, pp. 901-906.
LeBlanc et al., Metabolism of D-arabinose: origin of a D-ribulokinase activity in Escherichia coli. J. Bacterial., 1971, vol. 106( 1); 82-89.
Alkim et al., Optimization of ethylene glycol production from (D)-xylose via a synthetic pathway implemented in Escherichia coli. Microb. Cell Fact., 2015, vol. 15:127, pp. 1-12. (Year: 2015).
Broun et al., Catalytic plasticity of fatty acid modification enzymes underlying chemical diversity of plant lipids. Science, 1998, vol. 282: 1315-1317. (Year: 1998).
Cam et al., Engineering of a synthetic metabolic pathway for asimilation of (d)-xylose into value added chemicals. ACS Synth. Biol., 2016, vol. 5: 607-318. (Year 2016).
Choi et al., Snapshots of catalysis: the structure of fructose-1 ,6-(bis)phosphate aldolase covalently bound to substrate dihydroxyacetone phosphate. Biochem., 2001, vol. 40: 13868-13875. (Year: 2001).
Devos et al., Practical limits of function prediction. Proteins: Structure, Function, and Genetics. 2000, vol. 41: 98-107. (Year: 2000).
Lee et al., Transcriptional activation of the aldehyde reductase YqhD by YqhC and its implication in glyoxal metabolis of Escherichia coli K-12. J. Bacteriol., 201, vol. 192(16): 4205-4214. (Year: 2010).
Lee et al., Direct Microbial Conversion of Biomass to Advance Biofuels; Chapter 12, Remaining Challenges in the Metabolic Engineering of Yeasts for Biofuels, pp. 209-237; publisher Elsevier B,V. 2015 (Year: 2015).
Seffernick et al., Melarnine dearninase and Atrazine chlorohydrolase: 98 percent identical but functionally different. J. Bacteriol., 2001, vol. 183 (8): 2405-2410. (Year: 2001).
Whisstock et al., Prediction of protein function from protein sequence. Q. Rev. Biophysics., 2003, vol. 36 (3): 307-340. (Year: 2003).
Witkowski et al., Conversion of b-ketoacyl synthase to a Malonyl Decarboxylase by replacement of the active cysteine with glutamine. Biochemistry, 1999, vol. 38: 11643-11650. (Year: 1999).
Young et al., Optimizing pentose utilization in yeast: the need for novel tools and appraoches. Biotechnol. Biofuels., 2010, vol. 3:24, pp. 1-12. (Year: 2010).

* cited by examiner

PROCESS FOR PRODUCING AT LEAST ONE METABOLITE OF INTEREST BY CONVERSION OF A PENTOSE IN A MICROORGANISM

CROSS-REFERENCE TO RELATED APPLICATIONS

This application is a continuation of U.S. Ser. No. 15/526,444 filed May 12, 2017, now U.S. Pat. No. 10,570,423 issued Feb. 25, 2020, which was a national stage application, filed under 35 U.S.C. § 371, of International Patent Application No. PCT/FR2015/053138 filed 2015 Nov. 19, which claims priority to FR application No. 1461183 filed 2014 Nov. 19. Each of the previously noted applications is hereby incorporated by reference in their entirety.

FIELD OF THE INVENTION

The present invention relates to a process for producing at least one metabolite of interest in a microorganism. It provides more particularly a biosynthesis process of ethylene glycol and/or glycolic acid in a microorganism expressing an artificial/synthetic metabolic pathway for assimilation of pentoses derived advantageously from a renewable carbon source.

STATE OF THE ART

Ethylene glycol (EG) and glycolic acid (GA) are compounds used in a wide range of industrial applications in the petrochemical industry, as polymer precursors based on EG, such as polyethylene terephthalate (PET), or based on GA, such as some thermoplastic resins, but also as a coolant in motor vehicle antifreezes for the EG, and for the GA, in textile industry, in oil and gas industry as well as in a large number of cosmetics. These compounds are still widely produced in a petrochemical manner. However, metabolic engineering is a highly developing sector for over 15 years. This process comprises the design of artificial biosynthetic pathways and/or the optimization of natural pathways in a host organism and involves the transfer, the expression and the functional coupling of multiple enzymatic steps within said organism in order to allow the production of molecules of interest. The design of totally artificial biosynthetic pathways in the host microorganism enables more particularly to form an autonomous metabolic set of production of molecules of interest. These production methods have the advantage of using, as a substrate, a renewable carbon source, and henceforth represent a real alternative to fossil energy sources. In this regard, various metabolic pathways were described for EG bioproduction. In particular, they involve glycolysis intermediates. The Genomatica Company especially described in its patent applications WO2011130378 and WO2012177983 metabolic pathways, mainly anaerobic, of EG synthesis from serine, 3-phosphohydroxypyruvate, 3-phosphoglycerate or glyoxylate. Techniques for the GA bioproduction were also described. Thus, Mitsui Chemicals Inc. described a method using a microorganism for producing hydroxycarboxylic acids from an aliphatic polyhydric alcohol having a hydroxyl group at its end (EP 2 025 759 and EP 2 025 760). It is a bioconversion method, such as that is described by Michihiko Kataoka in an article concerning the GA production, using ethylene oxidizing microorganisms (Biosci. Biotechnol. Biochem., 2001). The GA may also be produced by bioconversion from glycolonitrile by using mutant nitrilases having an increased nitrilase activity, as described by Dupont de Nemours in the applications WO2006/069110 and U.S. Pat. No. 7,445,917.

The lignocellulosic biomass is a sustainable carbon source and a possible alternative to the fossil carbon sources. It generates a growing interest for the biosynthesis of metabolites of industrial interest. In these carbon materials, the D-xylose represents the second most abundant sugar after the glucose. However, the microorganisms do not use preferentially pentoses and when they do so, the yields are extremely low. The development of metabolic pathways assimilating this sugar is therefore a major focus of research for the industry.

The main sources of pentose use for the production of EG and GA by microorganisms are currently based on the use of natural pathways, optimized for the production of molecules of interest and/or on the addition of enzymes to use the products of these natural pathways.

Thus, a GA biological production method optimizing the pentose assimilation natural pathways is described in the applications WO2007140816 and WO2007141336 filed by Metabolic Explorer. These applications describe organisms genetically engineered at different levels to increase the flow of the glyoxylate pathway, increase the conversion of glyoxylate into glycolate and/or reduce the metabolism of the glycolate and its intermediate, glyoxylate. A subsequent application of Metabolic Explorer (WO2010108909) describes the opportunity to act, additionally, for optimizing GA production, on the lactate production pathways (by attenuating the methylglyoxal synthase and D-lactate dehydrogenase coding genes), on the aerobic/anaerobic metabolism transition by attenuating the ArcA gene regulating aerobic respiratory pathway control and/or by attenuating the genes encoding glycolate importing proteins.

More recently, EG synthesis metabolic pathways based on synthetic metabolic pathways for pentose assimilation were developed. Thus, Liu H et al. (Appl. Microbiol. Biotechnol, 2012, PMID:23233208) described *E. coli* strains expressing an ethylene glycol synthesis metabolic pathway from D-xylose and involving the enzymes (D)-xylose-dehydrogenase, (D)-xylonic-dehydratase, 2-dehydro-3-deoxy-D-pentonate aldolase and glycolaldehyde reductase. Nevertheless, the EG yields obtained by this method, of about 275 mg per gram of xylose, can be improved.

The Massachusetts Institute of Technology (MIT) also described in the application WO2013126721 an artificial metabolic pathway for producing EG from pentose. This pathway involves the phosphorylation in position 1 of the (D)-Ribulose or (L)-xylulose cycle. However, such a pathway requires, for the assimilation of the most abundant pentoses such as (D)-Xylose and (L)-Arabinose, the expression of several isomerases and epimerases which allow the conversion of D-Xylose into (D)-Xylulose and then into (D)-Ribulose and the conversion of (L)-Arabinose into (L)-Ribulose and then into (L)-Xylulose.

There is therefore a need in the state of the art for new efficient processes for producing metabolites of interest by transforming pentoses, including EG and/or GA, advantageously from renewable carbon sources and more particularly, based on the direct assimilation of the most abundant pentoses in these natural resources, such as (D)-Xylose and (L)-Arabinose.

SUMMARY OF THE INVENTION

The invention described in the present application meets the above mentioned technical objectives. It relates to a process for transforming at least one pentose in a microorganism for the production of at least one metabolite of interest, by assimilating said at least one pentose in a microorganism. It provides more particularly a simple and cost-efficient biosynthetic process for autonomously producing, in a microorganism, a metabolite of interest, including ethylene glycol and/or glycolic acid, from renewable carbon source such as for example, lignocellulose and in particular hemicellulose.

Using such a renewable carbon substrate provides a sustainable alternative to the production of metabolites of interest (such as ethylene glycol and glycolic acid), which are high value-added compounds for the petrochemical industry, and continue to this day to be widely produced by petrochemical pathway.

The new pentose assimilation pathway described in the invention constitutes a pathway which is parallel to the natural pentose assimilation pathways and does not exist naturally. It is thus largely independent of the controlling constraints on the host cell natural pathways. Thus, it makes it possible to circumvent natural pathways and their controls to produce metabolites of interest, such as ethylene glycol and/or glycolic acid.

Such a property allows its portability in a simplified manner to a broad spectrum of host microorganisms because their endogenous metabolism does not interfere with the synthetic pathway of the invention.

In addition, calculations on the theoretical yields of the synthetic pathway for pentose assimilation described in the present application for the production of ethylene glycol and glycolic acid estimate a significant improvement in the yields in relation to the biosynthetic processes based on the natural pathway optimization and/or an implementation and production simplification.

The process of the invention is thus characterized in that it comprises the following steps:
  (i) an operation of culturing a recombinant microorganism expressing a synthetic pathway for pentose assimilation which comprises at least the following reaction steps:
    a) phosphorylation in position 1 of a pentose selected from (D)-Xylulose and/or (L)-Ribulose,
    b) cleavage of the pentose-1-phosphate obtained at the end of step a) in order to obtain glycolaldehyde and dihydroxyacetone phosphate (DHAP), and
  (ii) an operation of recovering at least one metabolite of interest obtained at the end of the culturing operation (i).

Preferably, the step a) of the synthetic pathway for pentose assimilation can be catalyzed by a recombinantly expressed enzyme selected from the group consisting of ketohexokinase C (Khk-C), rhamnulose kinase (rhaB) and fuculose kinase (fucK).

Also preferably, the step b) is catalyzed by an aldolase, preferably, of class I. An aldolase of class I according to the invention is typically selected from the group consisting of aldolase B (Aldo-B) and Fructose-1,6 bisPphosphate aldolase (fructose 1,6 bP aldolase or FbaB).

According to an embodiment, the production process is characterized in that:
  the step a) is catalyzed by KhkC, and
  the step b) is catalyzed by aldolase B (Aldo-B) and/or fructose 1,6 bP aldolase (FbaB).

A particular embodiment of the process according to the invention provides ethylene glycol (EG) and/or glycolic acid (GA).

In such a process, the synthetic pathway for pentose assimilation further comprises the following steps:

c) reduction of the glycolaldehyde obtained at the end of step b) to ethylene glycol, and/or
c') oxidation of the glycolaldehyde obtained at the end of step b) to glycolic acid.

The embodiments described hereinafter can be combined with each other, unless otherwise specified in the process of the invention.

The step c) can be catalyzed by a glycolaldehyde reductase especially selected from the group consisting of: aldehyde reductase (YqhD), glycerol dehydrogenase (GldA) and propane-1,2-diol oxidoreductase (FucO).

The step c') can be catalyzed by a glycolaldehyde dehydrogenase, in particular the lactaldehyde dehydrogenase (AldA).

In a process of the invention, the microorganism is preferentially cultured on a carbon medium containing (D)-Xylose and/or (L)-Arabinose.

In a preferred embodiment of the process of the invention, the culture medium comprises a biomass hydrolysate comprising hemicellulose.

Typically, the synthetic pathway for pentose assimilation of the process according to the invention comprises, prior to step a), at least one of the following steps:
  a step of transporting (D)-xylose and/or (L)-arabinose in the microorganism;
  a step of converting (D)-Xylose into (D)-Xylulose, and/or
  a step of converting (L)-Arabinose into (L)-Ribulose.

The conversion of (D)-Xylose into (D)-Xylulose can be catalyzed by a (D)-Xylose isomerase and/or by the action of a (D)-xylose reductase and a xylitol dehydrogenase.

The conversion of (L)-Arabinose into (L)-Ribulose can be catalyzed by a (L)-arabinose isomerase and/or by the action of a (L)-arabinose reductase and an arabitol dehydrogenase.

According to the production process of the invention, the recombinant microorganism may be a bacterium, preferably selected from the group consisting of Enterobacteriaceae, Clostridiaceae, Bacillaceae, Streptomycetaceae, Streptococcaceae, Methylobacteriacae, and Corynebacteriaceae, preferably *Escherichia coli, Bacillus subtilis, Corynebacterium glutamicum, Clostridium acetobutylicum, Methylobacterium extorquens,* or *Lactococcus lactis*. The microorganism may also be a yeast, preferably selected from Saccharomycetaceae, Pichiaceae, and Schizosaccharomycetaceae, preferably *Saccharomyces cerevisiae, Schizosaccharomyces pombe, Kluyveromyces lactis, Kluyveromyces marxianus, Pichia jadinii, Scheffersomyces stipitis,* or *Pichia pastoris*. The microorganism of the invention may also be a fungus, preferably selected from the group consisting of *Penicillium, Aspergillus, Chrysosporium* or *Trichoderma*.

Preferably, the (D)-Xylulose-5 kinase and/or (L)-Ribulose-5 kinase activities of the microorganism used in the process of the invention were suppressed.

The invention also relates to a recombinant microorganism which expresses a synthetic pathway for pentose assimilation comprising at least the nucleic acids encoding the following enzymes:
  i) an enzyme adapted to phosphorylate in position 1 the pentoses selected from (D)-Xylulose and/or (L)-Ribulose,
  ii) an enzyme adapted to cleave said pentose phosphorylated in position 1 into glycolaldehyde and DHAP.

Advantageously, the natural pathways for pentose assimilation of such an organism were suppressed.

Generally, a microorganism expressing the synthetic assimilation pathway of the invention is further characterized in that the (D)-xylulose-5 kinase and/or (L)-ribulose-5 kinase activities were suppressed, and/or in that it carries at least one of the following modifications:

overexpression of a gene encoding a glyoxylate reductase;
overexpression of a gene encoding an isocitrate lyase;
deletion of the genes encoding malate synthases;
deletion of the genes encoding glyoxylate carboligases;
deletion of the genes encoding glycolate oxidases and/or glycolate dehydrogenases;
deletion of the genes encoding 2-keto-4-hydroxyglutarate aldolases, including Entner-Doudouroff Aldolase and/or phosphogluconate dehydratases;
deletion of a repressor gene of the aerobic response, including the arcA gene;
attenuation and especially, deletion of the isocitrate dehydrogenase expression;
deletion of the genes encoding glycolic acid internalization systems;
attenuation of the metabolic pathways which lead to the production of byproducts such as acetate, lactate or ethanol;
overexpression of at least one gene encoding a sugar carrier.

Preferably, the recombinant microorganism comprises:
at least an exogenous nucleic acid encoding the ketohexokinase C and
at least an exogenous nucleic acid encoding aldolase B.

Advantageously, said microorganism may comprise the following modifications:
overexpression of a gene encoding the main glycolaldehyde reductase;
deletion of the gene encoding the glycolaldehyde dehydrogenase.

Alternatively, the microorganism may comprise at least one of the following modifications to optimize the glycolic acid production:
overexpression of the gene encoding the glycolaldehyde dehydrogenase;
deletion of at least one of the genes encoding at least one of the glycolate oxidase subunits.

Typically, a microorganism suited for optimizing the glycolic acid production comprises the following modifications:
overexpression of a gene encoding a glyoxylate reductase;
overexpression of a gene encoding an isocitrate lyase, with or without the deletion of its transcriptional repressor;
deletion of the genes encoding malate synthases;
deletion of the genes encoding glyoxylate carboligases;
deletion of the genes encoding glycolate oxidases and/or glycolate dehydrogenases
deletion of the genes encoding 2-keto-4-hydroxyglutarate aldolases, including Entner-Doudouroff Aldolase and/or phosphogluconate dehydratases;
deletion of a gene encoding a repressor of the genes involved in the respiratory metabolism, including the arcA gene;
attenuation and in particular, deletion of the isocitrate dehydrogenase expression;
optionally, overexpression of a gene encoding a sugar carrier.

More preferably, especially in the case where the recombinant microorganism for the production of glycolic acid is *Escherichia coli*, the microorganism comprises the following modifications:
overexpression of aldA gene encoding a glycolaldehyde dehydrogenase;
overexpression of ghrA gene;
overexpression of aceA gene optionally along with the deletion of iclR gene encoding a transcriptional repressor of the glyoxylate pathway;
deletion of aceB and glcB genes;
deletion of at least one of the glcDEFG genes;
deletion of glc gene;
deletion of edd-eda genes;
deletion of arcA gene;
deletion of icd gene;
overexpression of galP gene.

FIGURES

FIG. 1. Natural pathways and synthetic pathways for (D)-xylose and (L)-arabinose assimilation. The reactions catalyzed by natural enzymes are represented as dashed lines. The reactions catalyzed by synthetic enzymes are represented as solid lines. (1) (D)-xylose isomerase, (2) (D)-xylulose-1 kinase, (3) (D)-xylulose-1-phosphate aldolase, (4) glycolaldehyde dehydrogenase, (5) glycolaldehyde reductase, (6) (L)-arabinose isomerase, (7) (L)-ribulose-1 kinase, (8) (L)-ribulose-1-phosphate aldolase. The gene names under the reactions correspond to the *Escherichia coli* genes encoding the enzyme with the corresponding activity.

Figure 2:
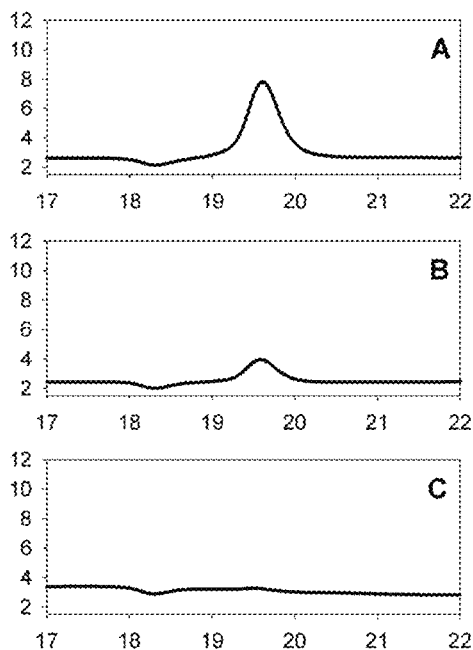

FIG. 2. Ethylene glycol in vitro synthesis by the synthetic pathway for (D)-xylose assimilation. HPLC chromatograms of (A) a 10 mM ethylene glycol solution and in (B) of a reaction mixture comprised of a (D)-xylulose-1 kinase (Khk-C, 0.005 Unit/mL), (D)-xylulose-1-phosphate aldolase (AldoB, 1 Unit/ml (Sigma-Aldrich-A6338)) and a glycolaldehyde reductase (GldA, 1 Unit/ml (Sigma-Aldrich G3512-250U)) or in (C) of a (D)-xylulose-1 kinase (Khk-C, 0.005 Unit/ml)) and a glycolaldehyde reductase (GldA, 1 Unit/ml (Sigma-Aldrich G3512-250U)). The enzymes were incubated for 3 h at 37° C. in a Hepes reaction buffer containing 100 mM Hepes; 85 mM KCl; 7.5 mM $MgCl_2$ at pH=7; 2 mM ATP; 5 mM $ZnCl_2$; 0.4 mM NADH. The reactions were initiated by adding 5 mM (D)-xylulose.

Legend: Intensity (ordinate) as a function of time in minutes (abscissa)

Figure 3:
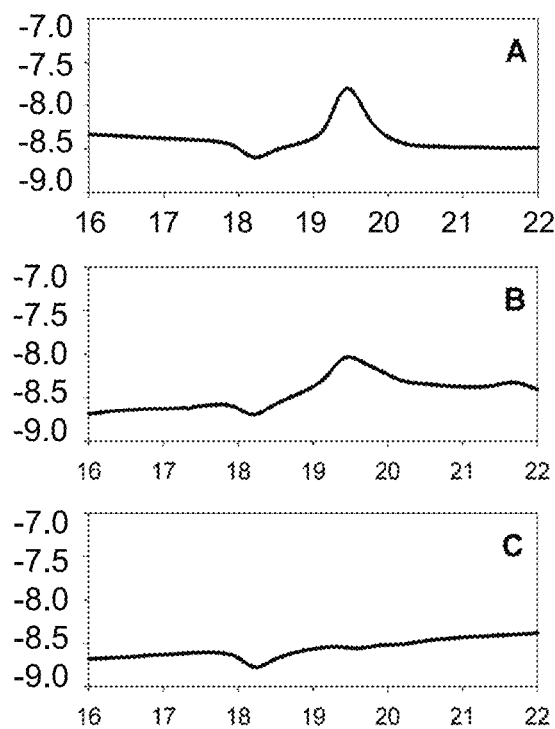

FIG. 3. Ethylene glycol in vitro synthesis by the synthetic pathway for (L)-arabinose assimilation. HPLC chromatograms of (A) a 1 mM ethylene glycol solution and in (B) of a reaction mixture comprised of a (L)-ribulose-1 kinase, (L)-ribulose-1-phosphate aldolase and a glycolaldehyde reductase. The enzymes were incubated for 3 h at 37° C. in a Hepes reaction buffer containing 55 mM Hepes; 45 mM KCl; 4 mM $MgCl_2$ at pH=7; 4 mM ATP; 0.4 mM NADH. The reactions were initiated by adding 20 mM (L)-ribulose.

Legend: Intensity (ordinate) as a function of time in minutes (abscissa)

Figure 4:
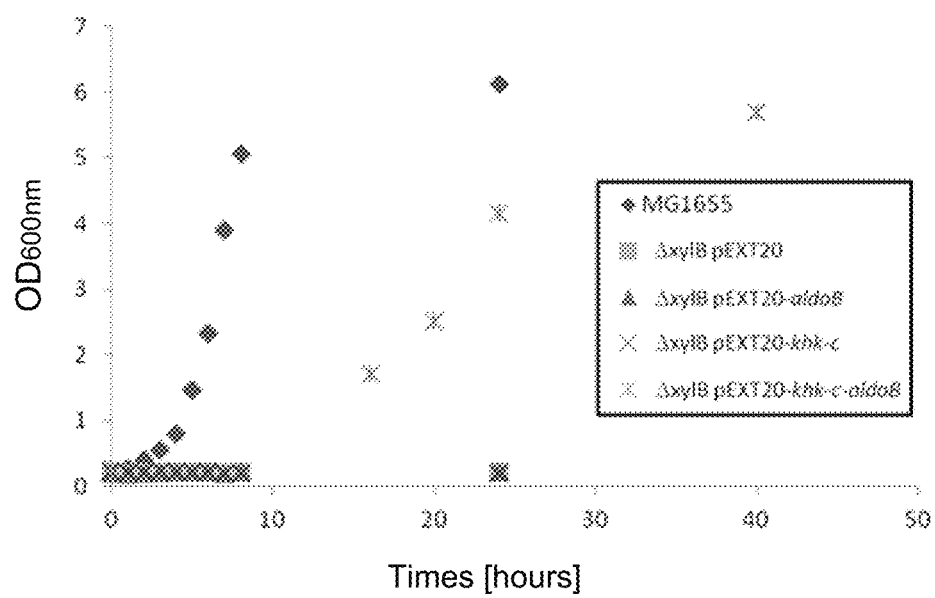

FIG. 4. Growth of *E. coli* strains in minimal medium containing (D)-xylose Legend: OD at 600 nm (ordinate) as a function of time in minutes (abscissa)

Figure 5:
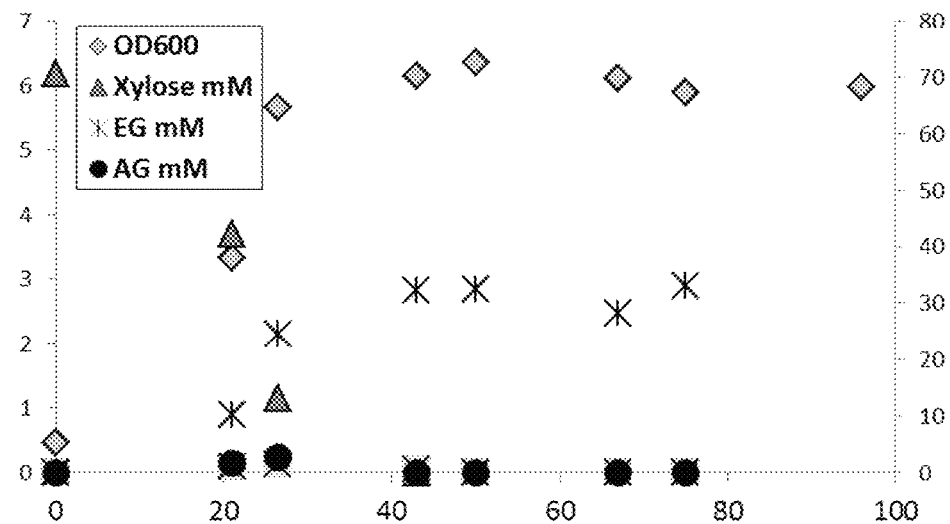

FIG. 5. Growth and metabolite production monitoring on xylose of an *E. coli* strain MG1655 ΔxylB pEXT20 khk-C-aldoB.

Legend: OD at 600 nm (ordinate on the left) and xylose in mM, ethylene glycol in mM and glycolic acid in mM (ordinate on the right) as a function of time in minutes (abscissa)

Figure 6:
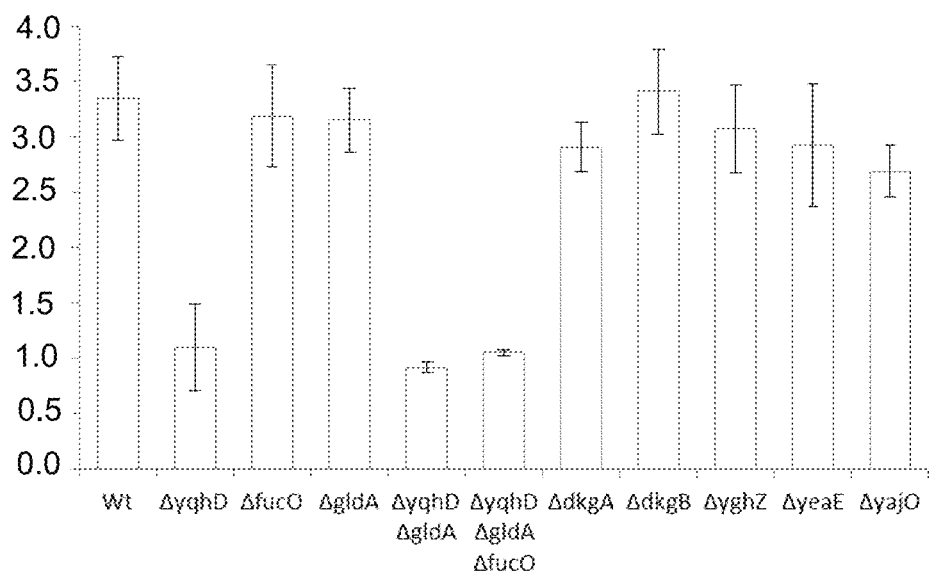

FIG. 6. Production of ethylene glycol (in mM as the ordinate) by candidate glycolaldehyde reductase mutants after incubation for 12 h in the presence of 10 mM glycolaldehyde.

Figure 7:
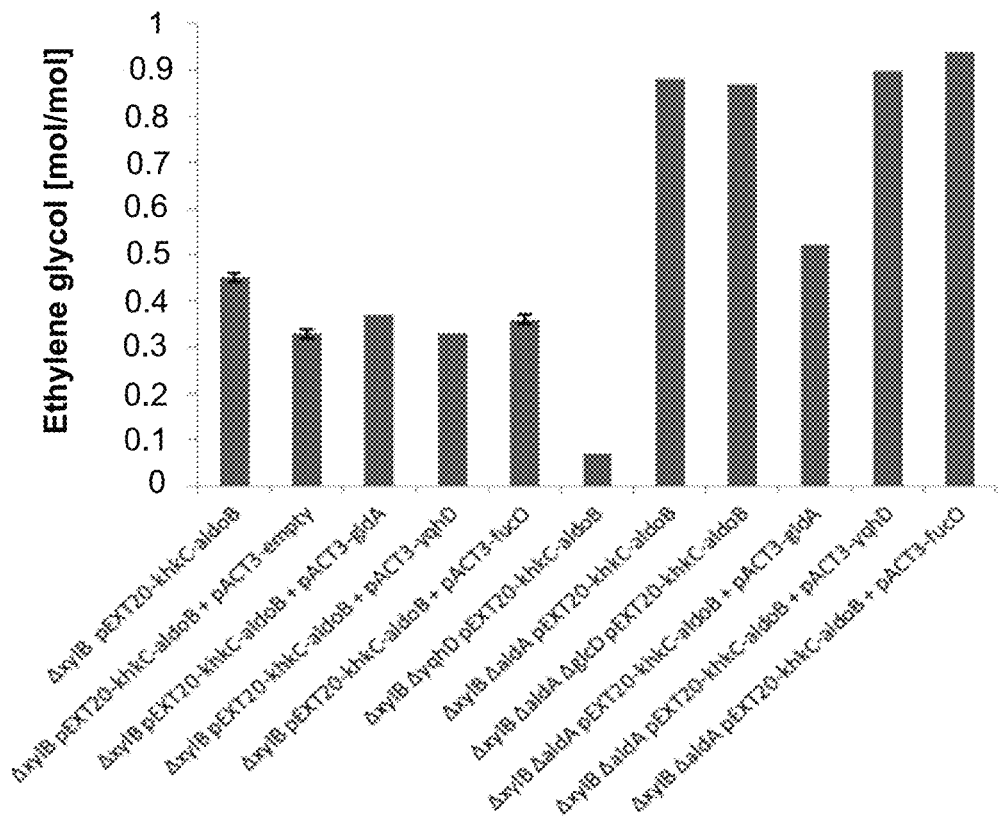

FIG. 7. Optimization of the ethylene glycol production in different mutants expressed as a yield in mol/mol of xylose (as the ordinate) via the synthetic metabolic pathway for (D)-xylose assimilation.

Figure 8:
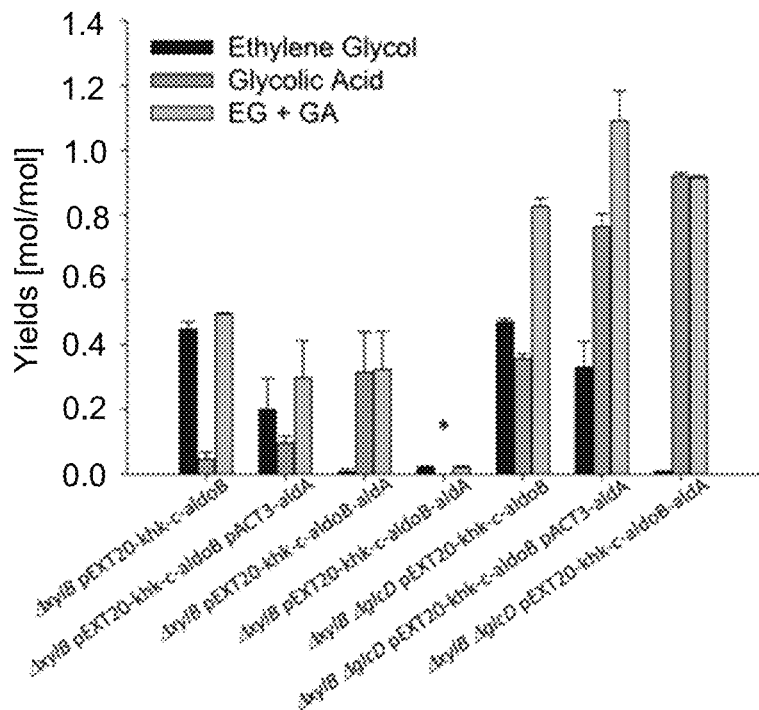

FIG. 8. Optimization of the glycolic acid production in different mutants according to the invention expressed as a yield in mol/mol of xylose (as the ordinate) via the synthetic metabolic pathway for (D)-xylose assimilation.

Figure 9:
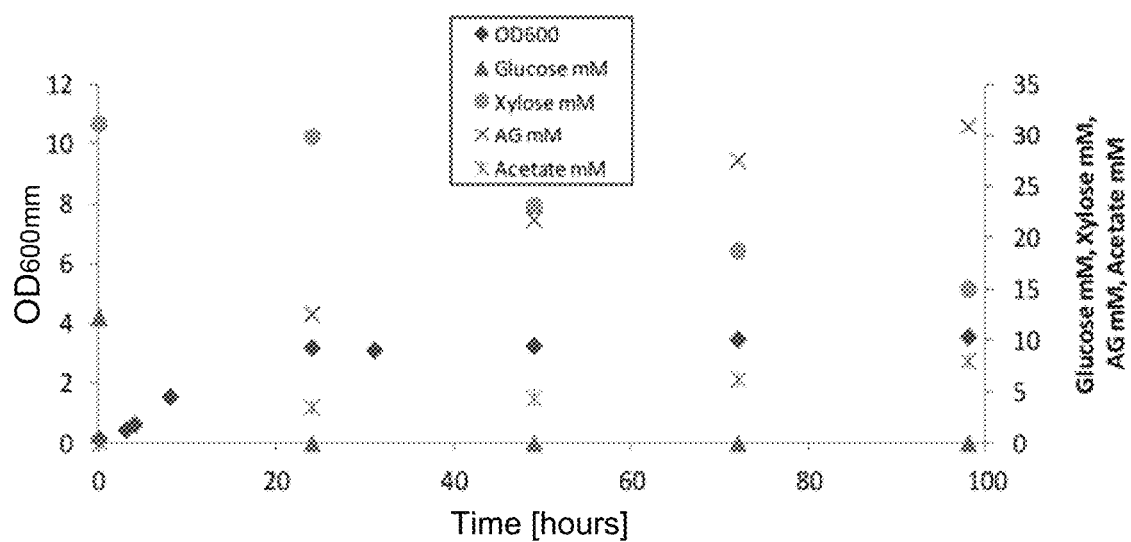

FIG. 9. Growth of the strain 905 in mineral medium in the presence of glucose and (D)-xylose. Legend: OD at 600 nm (ordinate on the left) and glucose, xylose, glycolic acid and acetate in mM (ordinate on the right) as a function of time in hours (abscissa).

Figure 10:
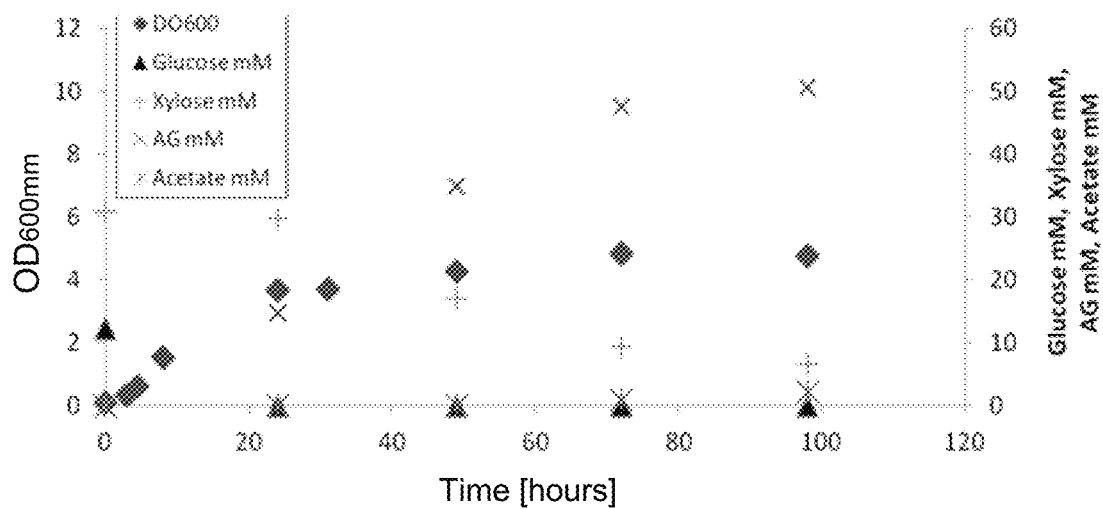

FIG. 10. Growth of the strain 979 in mineral medium in the presence of glucose and (D)-xylose. Legend: OD at 600 nm (ordinate on the left) and glucose, xylose, glycolic acid and acetate in mM (ordinate on the right) as a function of time in hours (abscissa).

Figure 11:
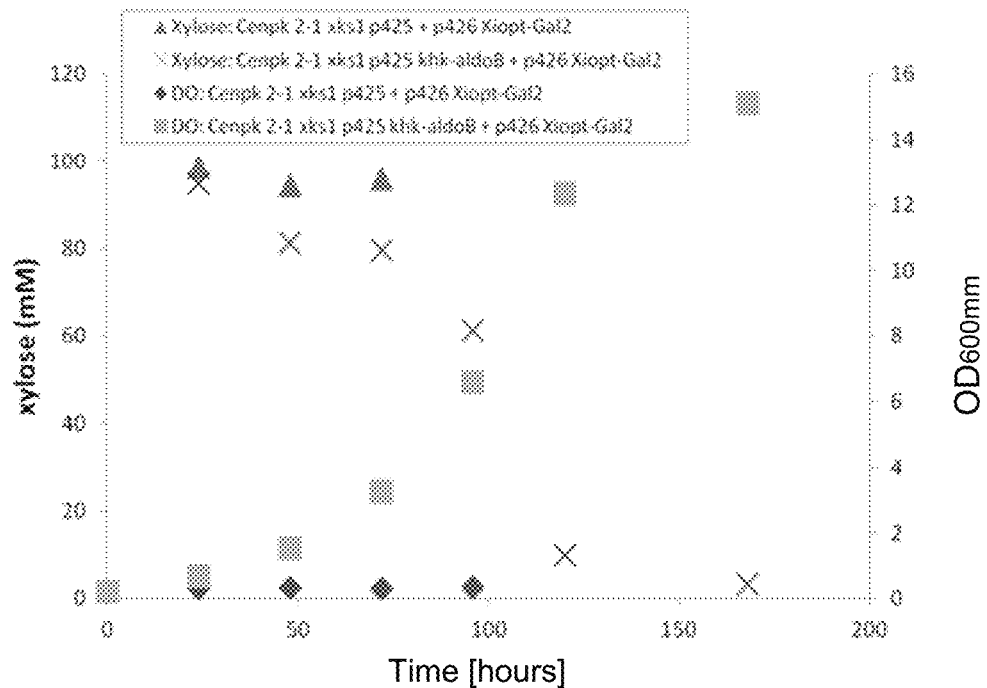

FIG. 11. Growth in mineral medium in the presence of xylose as a sole carbon source of CEN.PK-2-1 strains. Legend: OD at 600 nm (ordinate on the right) and xylose in mM (ordinate on the left) as a function of time in hours (abscissa).

Figure 12:
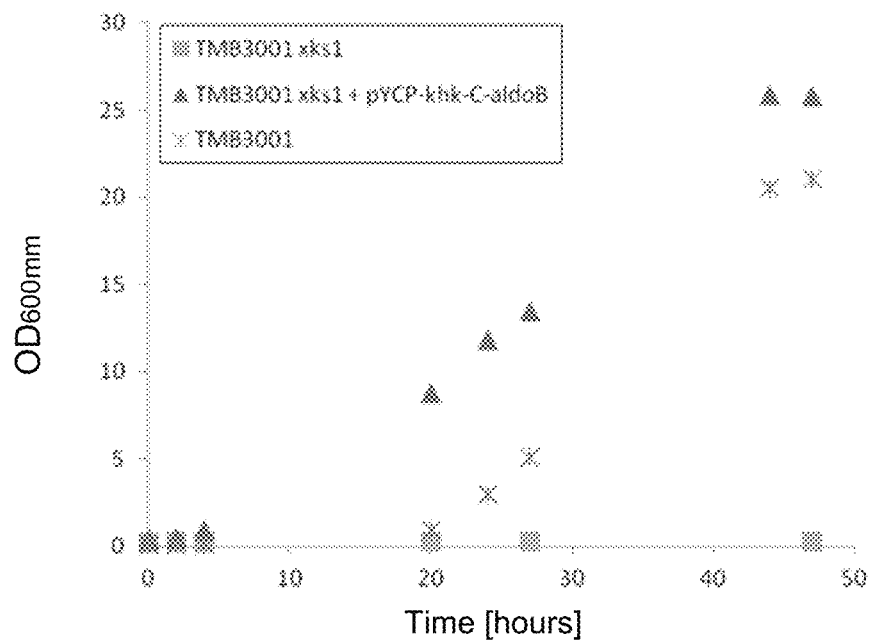

FIG. 12. Growth in mineral medium and xylose as a sole carbon source of TMB3001 strains. Legend: OD at 600 nm as a function of time in hours.

Figure 13:
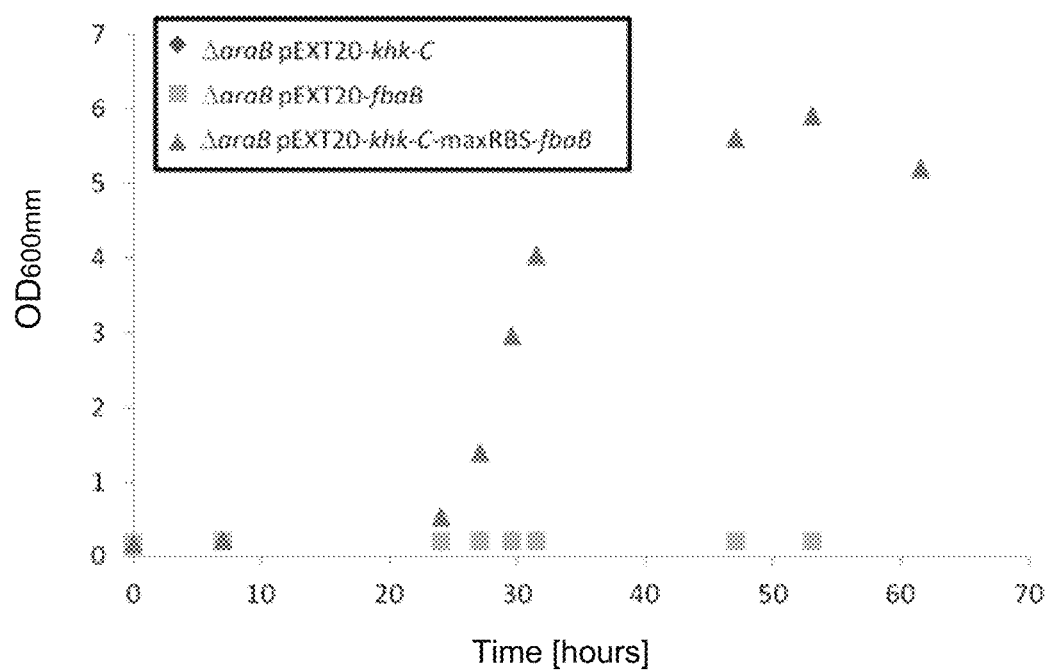

FIG. 13. Growth in mineral medium M9 and (L)-arabinose of AaraB strains with or without synthetic pathway. Legend: OD at 600 nm as a function of time in hours.

DEFINITIONS

Unless noted, the technical and scientific terms used in the present application have the usual meaning understood by a person skilled in the art able to implement the invention.

Unless also otherwise stated, the different embodiments described hereinafter can be combined with each other in the implementation of the invention.

By "pathway for pentose assimilation", it is meant in accordance with the invention, a metabolic pathway, namely a set of chemical reactions occurring in the microorganism, catalyzed by a series of enzymes acting sequentially, using pentoses as an initial substrate and resulting to their conversion for the formation of metabolites of interest.

By natural pathway for pentose assimilation, it is meant pentose assimilation involving their phosphorylation in position 5, and then their use in the so-called pentose phosphate metabolic pathway that is naturally occurring in most of the eukaryotic and prokaryotic cells. Typically, the (L)-arabinose is isomerized into (L)-ribulose which is then phosphorylated in position 5. The resulting (L)-ribulose-5-phosphate is epimerized on the carbon C3 to produce (D)-xylulose-5-phosphate, a substrate of the pentose phosphate pathway.

The expression "synthetic pathway" or "synthetic metabolic pathway" means in accordance with the invention that said metabolic pathway is not naturally implemented by the microorganism. This condition is typically met when at least one of the enzymes of said microorganism catalyzing at least one of the steps a) or b) of the metabolic pathway of the invention is not naturally expressed or when said at least one enzyme when it is expressed does not catalyze said at least one step a) or b).

As examples, (i) the metabolic pathway involving the phosphorylation in position 1 of a pentose selected from (D)-xylulose and (L)-Ribulose, by the Khk-C of human origin in a non-human cell and typically in a microorganism, (ii) the metabolic pathway involving the phosphorylation in position 1 of a pentose selected from (D)-xylulose and (L)-Ribulose, by the rhamnulose kinase RhaB in a microorganism and (iii) the metabolic pathway involving the phosphorylation in position 1 of a pentose selected from (D)-xylulose and (L)-Ribulose, by the fuculose kinase fucK in a microorganism, are synthetic pathways according to the invention.

The expression of the enzymes RhaB and fucK in *E. coli* depends on the presence of their natural substrate: (L)-rhamnulose and (L)-fucose, respectively. In the absence of their natural substrate (or when it is in a too low concentration), the expression of these enzymes in a microorganism and particularly in *E coli* can be recombinantly obtained under the control of a promoter in an inducible or constitutive manner.

The term "transformation" or "transfection" refers to the acquisition of new functional genes in a cell after the incorporation of exogenous nucleic acids.

The term "modification" or "modify" with regard to the protein or enzymatic activity level produced by a host cell refers to the control of the protein or enzymatic activity levels produced during the culture, such that these levels are increased or decreased as desired.

The term "modified" with regard to a nucleic acid or a polynucleotide means that the nucleic acid was modified in relation to the wild version contained in the host cell, including by a substitution, insertion, deletion-type mutation of part or all of said nucleic acid, or that said nucleic acid was operably linked to a transcription control region.

By "gene", it is meant in accordance with the invention, a DNA segment involved in the coding of ribosomal RNAs, regulatory RNAs, transfer RNAs, regulatory sequences (comprising typically a promoter region) operably linked to the expression of a peptide, polypeptide or protein, including coding (transcribed into messenger RNA) and non-coding regions preceding or terminating the coding region as well as introns (non-coding regions separating the coding regions or exons).

The term "operably linked" refers to a juxtaposition of elements in such a way that their arrangement allows them to be operably linked. A regulatory sequence containing typically a promoter region is operably linked to a coding region when it controls the transcription of the coding region, and a ribosome binding site is operably linked to a coding region when it is positioned so as to allow the translation of the mRNA.

The term "inactivation" or "suppression" or "attenuation" refers to the diminished or reduced or significantly reduced expression of a gene or to the diminished or reduced activity of a protein, or of the gene product, typically of an enzyme. For this purpose, different methods known to those skilled in the art can be used, such as:
  introducing a mutation in the gene, resulting in a reduced expression of the gene or expression of a protein whose activity is reduced,
  replacing the natural promoter by a promoter with low activity, resulting in a low expression of the gene,
  using mRNA-destabilizing element corresponding to the protein, or
  deleting the gene.

Typically, the attenuation of a gene or a protein is defined by an activity of the protein expressed by said gene decreased by at least 50%, preferably at least 60%.

The inactivation or deletion or suppression of a gene or a protein is defined by a residual activity of the protein product of said gene of less than 20%, in particular, less than 10%, especially less than 5%.

The term "expression" corresponds to the transcription and the translation of a gene into a protein, product of said gene.

The term "overexpression" corresponds to an expression increased in relation to the natural expression of said gene in the same host cell. Typically, the overexpression of a protein is defined by an activity of at least 200% of said protein as compared to its natural expression in the host cell.

The overexpression of a protein may be obtained by a variety of techniques known to those skilled in the art, such as:

mutation of a protein for obtaining form that is a more active or resistant to inhibition, increasing the expression of the gene encoding said protein (for example by introducing a specific promoter controlling the gene expression), adding multiple copies of the gene in the host cell, etc.

Host cells compatible with the invention can express an endogenous copy of one or more genes encoding a protein of interest according to the invention, as well as optionally a recombinant copy of said gene.

A nucleic acid encoding an enzyme associated with the present invention can be introduced in a host cell by any standard technique known to those skilled in the art. For example, nucleic acids can be introduced by transformation (chemical or electroporation), transfection, infection, transduction, etc.

The genes encoding proteins associated with the invention can be extrachromosomally-expressed in a recombinant expression vector or can be integrated within chromosomes.

By "vector", it is meant in accordance with the invention, a nucleic acid within which is inserted a sequence of interest, by restriction and ligation so that it is operably linked to regulation sequences for the expression as an mRNA transcript in a host cell. Vectors are consisting of RNA or preferably DNA and include, but are not limited to, plasmids, phagemids, viral genomes, bacteriophages and bacterial chromosomes.

A vector according to the invention may comprise one or more marker sequences for identifying cells transformed with said vector. Such markers include for example genes encoding proteins that increase or decrease the resistance or the sensitivity to antibiotic compounds, genes encoding enzymes whose activity is detectable by standard assays (for example, luciferase, galactosidase, alkaline phosphatase, etc.) or genes modifying the transformed cell phenotype (for example, encoding GFP, i.e.: Green Fluorescent Protein).

The regulatory sequences (promoters) used in the expression of the recombinant proteins of the invention may be endogenous (i.e. the native promoter of the gene to which it is associated) or exogenous regulatory sequences. The promoter can be inducible or constitutive.

By "host cell" or "host" microorganism, it is meant any type of cell capable of undergoing a transformation, transfection, transduction, etc., with a nucleic acid construction or an expression vector comprising one or more polynucleotides, in particular, one or more polynucleotides encoding enzymes described in the application.

Kinases are enzymes of the transferase group catalyzing phosphorylation reactions by adding a phosphate ion to a target molecule.

Oxidoreductases are enzymes catalyzing redox reactions by transferring $H^+$ ions and electrons. They are associated with redox coenzymes (NAD, FAD, FMN, etc.).

A dehydrogenase is an enzyme which oxides a substrate by transferring one or more ions ($H^+$) to an acceptor, generally a coenzyme of $NAD^+/NADP^+$ type or flavin as FAD or FMN.

An aldehyde dehydrogenase is an enzyme of the dehydrogenase type which catalyzes aldehyde oxidation.

When the enzymes mentioned in the present application are identified by their specific activity, such a definition includes all the polypeptides having the same specific activity and which are present in different cells and especially different microorganisms. Therefore, the invention also relates to the homologous proteins of the reference proteins mentioned in the present application having the same activity as the reference proteins, as well as genes encoding said homologous proteins.

In the absence of specification, the genes and proteins mentioned in the present application are identified in reference to *E. coli* (in particular the MG1655 strain). Khk-C and aldolase B are identified in reference to *H. sapiens*. However, proteins and thus genes homologous to the proteins (and to the genes encoding them) identified in the present application can be found in various microorganisms.

A protein homologous to a reference protein according to the invention has the same function, i.e. as the case may be for an enzyme, catalyzes the same reaction as the reference enzyme. A gene homologous to a gene encoding a reference protein according to the present invention encodes a homologous protein as defines above.

Typically, from the name of the protein and its sequence, a person skilled in the art is able to identify in other organisms equivalents of the proteins mentioned in the present application. This routine work is commonly performed using consensus sequences identified by sequence alignments with other proteins derived from different organisms.

Also preferably, a protein homologous to a reference protein corresponds to an enzyme having at least 30% sequence identity, preferably 40%, 50%, 55%, 60%, 65%, 70%, 75%, 80%, 85%, 90% or 95% identity with the sequence of the reference protein.

In order to determine the identity percentage of two amino acid sequences for the purpose of the invention, the sequences are aligned for optimum comparison. Gaps can be introduced in either of the sequences to be aligned in order to allow optimal alignment, and non-homologous sequences can be ignored for the comparison.

The percentage of identity of the two compared amino acid sequences can be obtained as described in the book of D. Voet and J. G. Voet, Biochimie ($2^{nd}$ Edition, De Boeck & Larcier, 2005, section 7.4, paragraph B). The alignments are carried out using the CLUSTAL W software (version 1.82) with the following parameters: (1) CPU MODE=ClustalW mp; (2) ALIGNMENT=<<full>>; (3) OUTPUT FORMAT=<<aln w/numbers>>; (4) OUTPUT ORDER=<<aligned>>; (5) COLOR ALIGNMENT=<<no>>; (6) KTUP (word size)=<<default>>; (7) WINDOW LENGTH=<<default>>; (8) SCORE TYPE=<<percent>>; (9) TOPDIAG=<<default>>; (10) PAIRGAP=<<default>>; (11) PHYLOGENETIC TREE/TREE TYPE=<<none>>; (12) MATRIX=<<default>>; (13) GAP OPEN=<<default>>; (14) END GAPS=<<default>>; (15) GAP EXTENSION=<<default; (16) GAP DISTANCES=<<default>>; (17) TREE TYPE=<<cladogram>> et (18) TREE GRAP DISTANCES=<<hide>>.

The lignocellulose is consisting of lignins, hemicelluloses and cellulose in varying proportions. Hemicelluloses are one of the three main components of the lignocellulosic biomass, and represent about 20-40% by weight of said biomass.

By "hemicellulose", it is meant according to the invention, a complex polysaccharide group which are characterized by their solubility in alkaline solutions (for example KOH 1M) and their insolubility in water. Hemicelluloses are structurally defined as polysaccharides whose backbone is consisting of (β-(1,4)-D-pyranose residues, wherein the O4 is in equatorial position. Short side chains are attached on the backbone. The hemicelluloses comprise xylans, arabinoxylans, xyloglucans, glucuronoxylans, and glucomannans. Their hydrolysis, for example carried out by contacting a lignocellulosic material with diluted sulfuric acid at high pressures and temperatures, results in the formation of monomeric sugars. Depending on the nature of the raw material and the hydrolysis conditions, the percentages of xylose, glucose and arabinose range from 60 to 80%, from 10 to 30% and from 10 to 30% by weight, respectively, based on the total weight of the lignocellulose hydrolysate.

Lignocelluloses obtained from hardwoods (typically deciduous trees), corncobs, grasses, leaves and newspapers are particularly rich in hemicellulosic sugars (Jorgensen H et al., Enzymatic conversion of lignocellulose into fermentable sugars: Challenges and opportunities. *Biofuels, Bioprod. Bioref* 2007, 1, 119-134). They represent the preferred raw material sources for the implementation of the modified microorganisms according to the invention. By "primer", it is meant a short DNA sequence complementary to the start of a template, which served as the starting point of the synthesis of the complementary strand of said template by a DNA polymerase.

DETAILED DESCRIPTION

Synthetic Pathway for Pentose Assimilation

The present invention relates to a process for converting a pentose in a recombinant microorganism expressing a synthetic pathway for pentose assimilation, for the production of at least one metabolite of interest.

This process according to the invention comprises:
(i) an operation of culturing a recombinant microorganism expressing a synthetic pathway for pentose assimilation, generally illustrated in FIG. 1, which comprises at least the following steps:
  a) phosphorylation in position 1 of a pentose selected from (D)-Xylulose and/or (L)-Ribulose in order to obtain (D)-Xylulose-1P and/or (L)-Ribulose-1P, respectively,
  b) cleavage of the pentose-1-phosphate obtained at the end of step a) ((D)-Xylulose-1P and/or (L)-Ribulose-1P), in order to obtain glycolaldehyde and dihydroxyacetone phosphate (DHAP), said pathway allowing at least one metabolite of interest to be obtained, and
(ii) an operation of recovering said at least one metabolite of interest obtained at the end of the culturing operation (i).

By "phosphorylation", it is meant advantageously adding a phosphate group, in the present case a phosphoryl $PO_3^{2-}$.

By "metabolite of interest", it is particularly meant glycolaldehyde and DHAP, but also their derivatives obtainable by oxidation or reduction reactions of these compounds, in particular ethylene glycol (EG), glycolic acid (AG) and their derivatives.

By "glycolic acid derivatives", it is particularly meant:
glycolate esters, such as ethyl ester glycolate or methyl ester glycolate, as well as:
glycolate containing polymers such as polyglycolic acid, as well as the glyoxylic acid derived from a glycolic acid oxidation.

It should be noted that in the present application, the terms "glycolic acid" and "glycolate" as well as the terms "glyoxylic acid" and "glyoxylate" are used as synonyms.

Preferably, the synthetic pathway for pentose assimilation expressed by the microorganism further comprises therefore advantageously the following steps:
  c) reduction of the glycolaldehyde obtained at the end of step b) into ethylene glycol, or
  c') oxidation of the glycolaldehyde obtained at the end of step b) into glycolic acid.

In such embodiments, the metabolites of interest obtained at the end of the synthetic pathway for pentose assimilation according to the invention are ethylene glycol and/or glycolic acid, and their derivatives.

Enzymes of the Invention:

The synthetic pathway for pentose assimilation, as shown in FIG. 1, is catalyzed by a set of enzymes.

The recombinant enzyme catalyzing the phosphorylation step a) of the synthetic pathway for pentose assimilation according to the invention is a kinase phosphorylating the (D)-Xylulose or the (L)-Arabinose in position 1.

Such an enzyme is for example selected from the group consisting of:
  ketohexokinase, preferably isoform C of ketohexokinase (KhK-C),
  rhamnulose kinase (RhaB) and
  fuculose kinase (FucK).

The ketohexokinase C is encoded by khk gene typically found in *H. sapiens*. In a preferred embodiment, the *H. sapiens* gene encoding Khk-C of sequence SEQ ID NO:1 is used.

The rhamnulose kinase as well as the fuculose kinase of the invention are respectively encoded by rhaB and fucK genes typically found in *E. coli*. Thus, in some embodiments, the *E. coli* rhaB gene encoding the rhamnulose kinase B (RhaB) of sequence SEQ ID NO:6 or the *E. coli* fucK gene encoding the fuculose kinase (FucK) of sequence SEQ ID NO:5 is used.

The enzyme catalyzing the cleavage step b) is an aldolase cleaving the (D)-xylulose-1P or (L)-ribulose-1P into glycolaldehyde and DHAP.

An aldolase according to the invention can be selected from aldolase B, encoded by the aldoB gene typically found in *Homo sapiens*, and fructose-1,6 bisphosphate aldolase B of *E. coli*, encoded by the fbaB gene typically found in *E. coli*.

Thus, in some particular embodiments, the *H. sapiens* gene aldoB encoding aldolase B, of sequence SEQ ID NO:2 or the *E. coli* gene fbaB encoding fructose-1,6 bisphosphate aldolase B, of sequence SEQ ID NO:9 is used. The enzyme catalyzing the reduction step c) is a glycolaldehyde reductase.

A glycolaldehyde (or aldehyde) reductase suitable for the invention can be for example selected from the aldehyde reductase encoded by:
  the yqhD gene, typically found in *E. coli*, encoding the aldehyde reductase YqhD of sequence SEQ ID NO:4,
  the glycerol dehydrogenase encoded by the gldA gene typically found in *E. coli*, encoding the glycerol dehydrogenase GldA and of sequence SEQ ID NO:51 and the L-1,2-propanediol oxidoreductase encoded by the FucO gene typically found in *E. coli*, encoding the L-1,2-propanediol oxidoreductase FucO and of sequence SEQ ID NO:52.

The enzyme catalyzing the oxidation step c') is a glycolaldehyde dehydrogenase.

A glycolaldehyde dehydrogenase suitable for the invention is for example the glycolaldehyde dehydrogenase encoded by the aldA gene, typically found in *E. coli* encoding the lactaldehyde dehydrogenase AldA, of sequence SEQ ID NO:3

The enzymes catalyze respectively the reduction and oxidation steps, advantageously in the presence of the reduced or oxidized form, respectively, of nicotinamide adenine dinucleotide (phosphate) (NAD(P)H), a redox coenzyme.

In some embodiments, the microorganism used in the present invention advantageously expresses, natively or recombinantly, at least one of the following enzymes:
  a xylose isomerase converting the (D)-Xylose into (D)-Xylulose, such as for example the enzyme encoded by the xylA gene of *E. coli*,
  a xylose reductase and a xylitol dehydrogenase, such as for example the enzymes encoded by the XYL1 and XYL2 genes of the yeast *Scheffersomyces stipitis*,
  a L-Arabinose isomerase, converting the (L)-Arabinose into (L)-Ribulose, such as for example the enzyme encoded by the araA gene of *E. coli*, and/or
  an arabinose reductase and an arabitol dehydrogenase.

Even preferably, the microorganism of the invention expresses, natively or recombinantly, at least one protein transporting pentoses into the cell, and including:
  proteins transporting (L)-Arabinose, such as for example the enzymes encoded by the araE, araF, araG or araH genes of *E. coli*; and/or
  proteins transporting (D)-xylose, such as for example the proteins encoded by the xylE, xylF, xylG or xylH genes of *E. coli* or the galP gene encoding a permease of the sugars, or the gal-2a gene of *S. cerevisiae*.

Recombinant Microorganism:

By "microorganism", it is meant in accordance with the invention a host cell selected from the prokaryotic cells, including archaebacteria, bacteria or prokaryotic microalgae, and eukaryotic cells, including fungi, yeasts and plant cells and eukaryotic microalgae.

By "recombinant microorganism", or "genetically modified microorganism", or "modified microorganism", it is meant in accordance with the invention, a host cell that has been modified in its genome, for example by adding an exogenous (or recombinant) nucleic acid, or by modifying an endogenous nucleic acid.

Bacteria suitable for the invention can be for example selected from the Enterobacteriaceae, Clostridiaceae, Bacillaceae, Streptomycetaceae, Streptococcaceae, Methylobacteriacae, and Corynebacteriaceae families.

Bacteria particularly suitable for the invention can be typically selected from the group consisting of *Escherichia coli, Bacillus subtilis, Corynebacterium glutamicum, Clostridium acetobutylicum, Methylobacterium extorquens*, and *Lactococcus lactis*.

Yeasts which are suitable for the invention can be for example selected from the Saccharomycetaceae, Pichiaceae, and Schizosaccharomycetaceae families.

Yeasts which are particularly suitable for the invention can be typically selected from the group consisting of *Saccharomyces cerevisiae, Schizosaccharomyces pombe, Kluyveromyces lactis, Kluyveromyces marxianus, Pichia jadinii, Scheffersomyces stipitis*, and *Pichia pastoris*.

Fungus genera suitable for the invention can be typically selected from the group consisting of *Penicillium, Aspergillus, Chrysosporium* and *Trichoderma*.

In a preferred embodiment of the invention, *Escherichia coli, Scheffersomyces stipitis* or *Saccharomyces cerevisiae* is used as a host microorganism.

Advantageously, a microorganism naturally able to assimilate (D)-xylose and/or (L)-arabinose is used.

Preferably, the synthetic pathway for pentose assimilation according to the invention involves that at least one enzyme catalyzing one of the phosphorylation a), cleavage b), reduction c) or oxidation c') steps is recombinantly expressed by the microorganism.

Typically, at least the enzyme catalyzing the phosphorylation step a) and/or at least the enzyme catalyzing the cleavage step b) of the process of the invention is recombinantly expressed.

In a particular embodiment, enzymes catalyzing the phosphorylation a), cleavage b), and reduction c) and/or oxidation c') steps are recombinant enzymes.

In some embodiments, at least one of said recombinant enzymes is an enzyme encoded by a heterologous gene (i.e. not naturally expressed in the reference host organism), in particular at least one of the enzymes catalyzing a) and b) steps is encoded by a heterologous gene.

Preferably, the microorganism expresses at least the KhkC.

More preferably, the microorganism recombinantly expresses:
  the KhkC (in particular KhkC, *H. sapiens* encoded by the khkC gene of sequence SEQ ID NO:1) catalyzing the step a) of the pentose assimilation pathway, and
  the aldolase B, encoded by the aldo-B gene (in particular by the aldoB gene of sequence SEQ ID NO:2) or the fructose-1,6 bisphosphate aldolase, encoded by the fbaB gene (in particular the fbaB gene of sequence SEQ ID NO:9).

In a particular embodiment, the glycolaldehyde reductase and/or glycolaldehyde dehydrogenase catalyzing respectively steps c) and c') of the synthetic pathway for pentose assimilation of the invention are endogenous enzymes naturally expressed by the microorganism.

In some embodiments, the endogenous enzymes of the assimilation synthetic pathway of the invention can be overexpressed, especially the enzymes encoding the steps of reduction c) or oxidation c'). In particular, the glycolaldehyde dehydrogenase can be overexpressed in order to stimulate the oxidation step c'). For example, in *E. coli*, the aldA gene encoding a glycolaldehyde dehydrogenase can be overexpressed.

In some embodiments of the invention, the enzymes converting (D)-xylose or (L)-Arabinose into (D)-xylulose or (L)-ribulose, respectively, namely isomerases or epimerases such as described previously, or the proteins importing (D)-Xylose or (L)-Arabinose in the cell, are overexpressed in the microorganism.

In an embodiment of the invention, the nucleic acids encoding the enzymes catalyzing steps a) and b) are cloned into operon in an expression vector under the control of the same promoter. In some embodiments, the nucleic acids encoding the enzymes catalyzing steps a), b), and c) and/or c') are cloned into operon.

The recombinant protein expression is controlled by an inducible, or preferably, constitutive promoter.

Optimization of the Synthetic Pathway for Pentose Assimilation:

In some embodiments, the activity of one or more endogenous enzymes of the host cell can also be modified so as to optimize ethylene glycol and/or glycolic acid production.

Some modifications that could be made to a microorganism of the invention are described below.

A) Preferably, the microorganism used is genetically modified so as to attenuate or suppress the activity of endogenous enzymes involved in the natural pathways for pentose phosphate assimilation, and in particular enzyme(s) catalyzing the phosphorylation in position 5 of the pentose cycle, and more particularly (L)-ribulose-5-kinase and/or (D)-xylulose-5-kinase.

By way of example, araB and/or xylB genes, encoding the ribulose-5-kinase and xylulose-5-kinase, respectively, typically found in *E. coli*, can be attenuated or preferably inactivated.

Such a modification is provided for directing the carbon flow preferentially to the synthetic pathway for pentose assimilation of the invention, and optimizing the ethylene glycol and/or glycolic acid production by said synthetic pathway.

In an embodiment of the invention, a microorganism in which the xylB gene, and in particular the xylB gene encoding the xylulose kinase of sequence SEQ ID NO:53 is deleted, is used.

B) The activity of the glycolaldehyde reductase and/or glycolaldehyde dehydrogenase type enzymes can also be modified in order to direct the assimilation synthetic pathway of the invention to the glycolic acid or ethylene glycol production.

By way of example, the enzymes encoded by the aldA genes, encoding a glycolaldehyde dehydrogenase, as well as the gldA, fucO and/or yqhD genes encoding a glycolaldehyde reductase, can be notably overexpressed to promote the production of ethylene glycol, or attenuated or inactivated, to promote the production of glycolic acid.

Advantageously, the ethylene glycol production is optimized by using a microorganism in which at least one (and preferably both) of the following modifications are further made regarding the endogenous enzyme expression:
  overexpression of the gene encoding at least one glycolaldehyde reductase, preferably the main glycolaldehyde reductase, expressed by the microorganism;
  inactivation or deletion of the gene encoding a glycolaldehyde dehydrogenase catalyzing step c', for example aldA gene.

Advantageously, the glycolic acid production can be optimized by using a microorganism in which at least one of the following modifications (and preferably at least the first two) are made regarding the endogenous enzyme expression:
  overexpression of the gene encoding the glycolaldehyde dehydrogenase, for example, the glycolaldehyde dehydrogenase encoded by the aldA gene;
  reduction of the glycolic acid degradation, notably by attenuating or inactivating glycolate oxidase, for example by inactivating at least one of the glcDEFG genes encoding at least one of the glycolate oxidase subunits;
  optionally inactivation of the gene(s) encoding a glycolaldehyde reductase.

Preferably, a microorganism according to the invention further comprises the modifications unique to the expression of the synthetic pathway for pentose assimilation of the invention, and notably unique to the catalysis of the phosphorylation a) and cleavage b) steps of this pathway, at least one of the additional modifications described in above points A) and B).

More preferably, the microorganism comprises at least the modifications described in point A). According to the embodiments, this modification can be combined with the modifications in point B) for optimizing the ethylene glycol or glycolic acid production.

The above mentioned modifications can be combined.

In particular:
  to optimize the ethylene glycol production, the inactivation of the enzymes catalyzing the pentose phosphorylation in position 5, including (L)-ribulose-5-kinase and/or (D)-xylulose-5-kinase (such as xylB or araB genes), can be combined with the inactivation of the glycolic acid synthesis pathway (notably by inactivating the gene(s) encoding a glycolaldehyde dehydrogenase, for example aldA gene). These inactivations can be combined with an overexpression of the gene encoding the glycolaldehyde reductase catalyzing the step c) of the process of the invention;
  to optimize the glycolic acid production, the inactivation of the enzymes catalyzing the pentose phosphorylation in position 5, including (L)-ribulose-5-kinase and/or (D)-xylulose-5-kinase (notably coded by the xylB or araB genes) can be combined with the inactivation of the glycolate oxidase by inactivating at least one of the glcDEGF genes encoding its subunits and/or with the overexpression of the glycolaldehyde dehydrogenase encoded by the aldA gene. Optionally, the gene encoding the glycolaldehyde reductase catalyzing step c) of the process of the invention is also inactivated.

For example, a microorganism modified to optimize the ethylene glycol production expresses at least the phosphorylation, cleavage and reduction activities corresponding to the previously described steps a), b) and c), preferably the enzymes KhkC, aldolase B (notably encoded by the aldoB gene) as well as a glycolaldehyde reductase (as the aldehyde reductase YqhD or the glycerol dehydrogenase GldA or even the enzyme encoded by the fucO gene) and comprises the following modifications:
  the deletion of the gene encoding aldehyde dehydrogenase, including the aldA gene;
  the deletion of the genes encoding the enzyme(s) catalyzing the phosphorylation in position 5 of the (D)-xylulose and/or (L)-ribulose, and more particularly the (D)-xylulose-5-kinase and/or (L)-ribulose-5-kinase, including the araB and/or xylB genes.

C) It is also possible to use a genetically modified microorganism in order to promote, in addition to the synthetic pathway of the invention, the glycolic acid production by natural pathways.

Indeed, the inventors further found that the glycolic acid production may also be further increased by combining the assimilation synthetic pathway functioning according to the invention with genetic modifications leading in parallel to the glycolic acid production by the so-called glyoxylate pathway.

A microorganism according to the invention can therefore have for example modifications promoting the glycolic acid production from glyoxylate, as described in the application WO2010/108909.

Thus, the dihydroxyacetone phosphate (DHAP or glycerone phosphate), especially obtained at the end of the cleavage step b), could include the natural pathways of the glycolysis, the tricarboxylic acid cycle (CAT) and the glyoxylate pathway, a CAT shunt (see for review Neidhardt, F.

C. (Ed. in Chief), R. Curtiss III, J. L. Ingraham, E. C. C. Lin, K. B. Low, B. Magasanik, W. S. Reznikoff, M. Riley, M. Schaechter, and H. E. Umbarger (eds). 1996. *Escherichia coli and Salmonella: Cellular and Molecular Biology.* American Society for Microbiology).

The optimization of the glyoxylate pathway may therefore be obtained by at least one, preferably, by a combination of the following modifications:
i) overexpression of a gene encoding a glyoxylate reductase;
ii) overexpression of a gene encoding an isocitrate lyase, optionally along with the deletion of the gene encoding its transcriptional repressor;
iii) deletion of the genes encoding malate synthases;
iv) deletion of the genes encoding glyoxylate carboligases;
v) deletion of the genes encoding genes encoding glycolate oxidases or glycolate dehydrogenases;
vi) deletion of the genes encoding 2-keto-4-hydroxyglutarate aldolases, including the Entner-Doudouroff Aldolase and/or phosphogluconate dehydratases;
vii) deletion of an aerobic response repressor gene (i.e. a gene encoding a repressor of the genes involved in the respiratory metabolism), in particular the arcA gene;
viii) attenuation and especially deletion of the isocitrate dehydrogenase expression;
ix) optionally, deletion of the genes encoding glycolic acid internalization systems; and
x) optionally, attenuation of the metabolic pathways leading to the by-product production such as acetate, lactate or ethanol.

In case the recombinant microorganism for producing glycolic acid is *Escherichia coli*, the above described modifications correspond to
i) the overexpression of the ghrA gene and/or ycdW gene;
ii) the overexpression of the aceA gene along with or without the deletion of its transcriptional repressor, iclR;
iii) the deletion of the aceB and glcB genes;
iv) the deletion of the gcl gene;
v) the deletion of at least one gene selected from glcD, glcE, glcF or glcG;
vi) the deletion of the edd-eda genes;
vii) the deletion of the arcA gene;
viii) the attenuation and preferably the deletion of the expression of icd gene;
ix) the deletion of the glcA, lldP, and/or yjcG genes;
x) the deletion of the ackA-pta, poxB, ldhA and/or adhE genes.

Advantageously, the following modifications are made to optimize the glycolic acid production in a microorganism according to the present invention, for example in *E. coli*:
i) the overexpression of the ghrA gene;
ii) the overexpression of the aceA gene optionally along with the deletion of iclR gene;
iii) the deletion of the aceB and glcB genes;
iv) the deletion of the gcl gene;
v) the deletion of at least one gene selected from glcD, glcE, glcF or glcG;
vi) the deletion of the edd-eda genes;
vii) the deletion of the arcA gene;
viii) the deletion of the icd gene.

In an embodiment, the microorganism carrying the above modifications does not express enzyme catalyzing the phosphorylation in position 5 of (L)-ribulose and/or (D)-xylulose, and more particularly (L)-ribulose-5-kinase and/or (D)-xylulose-5-kinase. Thus, in some embodiments, a microorganism in which xylB and/or araB genes are deleted, is used.

Alternatively, the microorganism (advantageously *E. coli*) expresses one or more enzymes catalyzing the phosphorylation in position 5 of (L)-ribulose and/or (D)-xylulose, and more particularly (L)-ribulose-5-kinase and/or (D)-xylulose-5-kinase. Typically, the microorganism expresses the xylB and/or araB gene. Such a microorganism provides an excellent glycolic acid yield when it is cultured on a glucose containing medium, in particular, containing at least glucose and xylose or xylulose. Preferably, the medium mostly contains glucose.

D) It is finally possible, for increasing the ethylene glycol or glycolic acid production, to use a microorganism in which at least one gene encoding a sugar carrier (for example galP gene encoding a sugar permease and/or gal-2a gene of *S. cerevisiae*) is overexpressed. Advantageously, such a gene is constitutively expressed.

In a most preferred embodiment of the invention, for producing glycolic acid, a microorganism combining the modifications described in the above paragraphs A) to D) is used. In particular, a microorganism combining the modifications reported in the above paragraphs B), C) and D) for the production of glycolic acid is used.

Advantageously, such a microorganism expresses KhkC and aldolase B and comprises the following modifications:
overexpression of the gene encoding glycolaldehyde dehydrogenase, for example the glycolaldehyde dehydrogenase encoded by the aldA gene;
overexpression of the ghrA gene;
overexpression of the aceA gene optionally along with the deletion of the iclR gene;
deletion of the aceB and glcB genes;
deletion of the gcl gene;
deletion of at least one gene selected from glcD, glcE, glcF or glcG;
deletion of the edd-eda genes;
deletion of the arcA gene;
deletion of the icd gene;
overexpression of the galP gene.

Depending on the selected culture substrate, such a microorganism may also carry or not a deletion of the xylB gene and/or araB gene. Preferably, the expression of xylB gene and/or arab gene is maintained when the microorganism is cultured on a substrate comprising glucose.

Similarly, depending on the culture substrate, a microorganism expressing, recombinantly or not, enzymes converting (D)-xylose or (L)-Arabinose into (D)-xylulose or (L)-ribulose, respectively, namely (D)-xylulose isomerases or (L)-arabinose isomerases, or (D)-xylose reductases/(D)-xylitol dehydrogenases, or (L)-arabinose reductases/(L)-arabitol dehydrogenases, as previously described, is used.

Generally, but not limited to, the ethylene glycol theoretical yield of the process of the invention is about 1 mol of ethylene glycol per mol of xylose or arabinose.

The glycolic acid theoretical yield of the process of the invention is about 1 mol of glycolic acid per mol of xylose or arabinose, without activating the glyoxylate cycle. When operating the synthetic pathway and the glyoxylate cycle in parallel, the theoretical yield is about 2 mol of glycolic acid per mol of xylose or arabinose.

Culture of the microorganism:

The culture conditions of the microorganism according to the invention may be adapted in accordance with the conventional techniques known to those skilled in the art.

Typically, the bacteria used as host cells in the present invention can be cultured in media of all types and composition.

The culture media are typically carbon media comprising, or supplemented with, various compounds including especially different sources of carbon, and in particular, of pentoses, such as (D)-glucose, (D)-xylose, (L)-arabinose, and/or lignocellulosic biomass hydrolysates, in particular hemicellulose, starch and the derivatives thereof.

In some embodiments, the culture medium comprises less than 5%, in particular less than 4%, less than 3%, less than 2% or less than 1% of rhamnulose.

By "biomass hydrolysate", it is meant in particular lignocellulosic hydrolysates, in particular hydrolysates comprising at least 20% of xylose and/or at least 5%, especially at least 10% of arabinose, by weight based on the total weight of the hydrolysate. In a preferred embodiment, lignocellulosic hydrolysates of hardwoods, corncobs, and paper are thus used.

Other parameters relating to the culture conditions can be optimized by routine experiments, such as pH or temperature.

In some embodiments, the culture temperature ranges from 25 to 43° C. and depends essentially on the host cell and culture medium type. By way of example, when the host cell is E. coli, the optimum culture temperature ranges generally from 30 to 38° C.

The culture duration also depends on the above mentioned culture parameters. Typically, cells can be cultured between 6 and 300 hours.

Preferably, the metabolite(s) of interest obtained at the end of the microorganism cultivation according to the invention are recovered from the culture medium.

The present application also relates to a recombinant microorganism as described in the present application.

In particular, the present invention relates to a microorganism expressing a synthetic pathway for pentose assimilation according to the invention.

According to different embodiments, the natural pathways for pentose assimilation are maintained or inactivated (for example by deleting genes encoding the xylulose-5-kinase and/or ribulose-5-kinase).

A microorganism according to the invention expresses at least:
 a nucleic acid encoding an enzyme able to phosphorylate in position 1 a pentose selected from (D)-xylulose and/or (L)-ribulose, and
 a nucleic acid encoding an enzyme of aldolase type able to cleave the (D)-xylulose-1-phosphate and/or (L)-ribulose-1-phosphate into glycolaldehyde and DHAP, as previously described.

Preferably, at least one of these enzymes is recombinantly expressed.

In some embodiments, at least one of these enzymes is coded by an exogenous nucleic acid and preferably, the microorganism expresses at least:
 a nucleic acid encoding the isoform C of ketohexokinase (typically found in H. sapiens) and
 at least a nucleic acid encoding aldolase B.

In some embodiments, the microorganism is further modified as described in the above points A) to E).

For example, a microorganism suitable for the production of glycolic acid may advantageously comprise the following modifications:
 overexpression of the gene encoding the glycolaldehyde dehydrogenase, for example the glycolaldehyde dehydrogenase encoded by the aldA gene;
 overexpression of the ghrA gene;
 overexpression of the aceA gene;
 optionally deletion of the iclR gene;
 deletion of the gcl gene;
 deletion of at least one gene selected from the glcD, glcE, glcF or glcG genes;
 deletion of the aceB and glcB genes;
 deletion of the edd-eda genes;
 deletion of the arcA gene;
 deletion of the icd gene;
 optionally deletion of the xylB and/or araB genes.

EXAMPLES

Medium Composition
Luria-Bertani (LB) Medium

For one liter of medium: 10 g of tryptone, 5 g of yeast extract, 5 g of sodium chloride in one liter of purified water. The medium is autoclaved before use. For use in solid medium, 2% of agar is added to the medium before autoclaving.

Minimal Medium M9

For one liter of medium: 18 g $Na_2HPO_4*12\ H_2O$; 3 g $KH_2PO_4$; 0.5 g NaCl; 2 g $NH_4Cl$; 0.5 g $MgSO_4*7\ H_2O$; 0.015 g $CaCl_2*2\ H_2O$; 1 ml of a trace element solution (containing per liter 0.04 g $NaEDTA*2H_2O$, 0.18 g $CoCl_2*6\ H_2O$; $ZnCl_2SO_4*7\ H_2O$; 0.04 g $Na_2MoO_4*2\ H_2O$, 0.01 g $H_3BO_3$, 0.12 g $MnSO_4*H_2O$, 0.12 g $CuCl_2*H_2O$); amounts of (D)-glucose, (D)-xylose, and (L)-arabinose specified in the text. The medium is adjusted at pH 7 and filtered.

The YPD medium is used as a rich medium for S. cerevisiae growth. For one liter, 10 g of yeast extracts, 20 g of bacto-peptone. The medium is autoclaved before use and 20 g of filtered glucose are added. For use in solid medium, 2% agar is added to the medium before autoclaving.

Minimal Medium SCD for Saccharomyces cerevisiae

For one liter, 1.7 g of Yeast Nitrogen Base without amino acids, 5 g of ammonium sulfate without amino acids, drop-out of 0.940 g essential amino acids except those used to demonstrate an auxotrophy, 900 ml of water, and then the whole is autoclaved. When used in solid medium, 20 g of bacto-agar are added. 100 ml of a 20% sugar solution are added.

Growth Test in M9 Medium+Xylose

All the cultures are carried out in 250 ml Erlenmeyer flasks containing 50 ml of culture medium and by stirring the cultures at 200 RPM.

The cells to be tested are cultured overnight at 37° C. in LB medium. This preculture is subsequently used to inoculate to $OD_{600\ nm}$~0.2 M9 medium+10 g/l of glucose. In an exponential growth phase (OD between 0.6 and 1), IPTG is added at 1 mM and the cultures are thus incubated for 16 to 18 hours. After this incubation period, the cells are washed two times with sterile water and reseeded to $OD_{600\ nm}$~0.2 in M9 medium+1 mM IPTG+glucose and/or xylose and/or arabinose in amounts specified in the text. The $OD_{600\ nm}$ is monitored and aliquots are taken, centrifuged and injected in HPLC for metabolite analysis.

Strain Construction Methods
Bacterial Transformation

The bacterial transformations are made on commercial chemo-competent cells or laboratory prepared cells. Cells made chemo-competent are prepared according to the calcium chloride protocol (Dagert and Ehrlich, 1979). The transformation is then performed by leaving during 20 mM the plasmid DNA to be transformed in contact with competent bacteria on ice, and then 45 seconds thermal shock at 42° C. is carried out. The cells are replaced 5 minutes on ice, and then 1 ml of LB medium is added before incubating them for 1 h at 37° C. The cells are subsequently spread on solid LB dish supplemented with the corresponding selection marker.

Generally, in addition to the plasmids developed in the context of the present invention, the following plasmids were used: pACT3 (Dykxhoorn et al., 1996), pEXT20 (Dykxhoorn et al., 1997), pGEM-T (Promega), pET28a (Novagen), pCP20 (Cherepanov & Wackernagel, 1995), peX-A-aldoB (Eurofins) and pET11-KHK-C (Asipu et al., 2003).

Gene Deletion by Transduction of a Kanamycine Cassette from a KEIO Strain

To transfer a gene deletion carried by an *E. coli* KEIO strain to a given receptor strain of *E. coli* MG1655, a transduction is performed.

From a Keio strain cultured in LB+50 µM kanamycine at 37° C. overnight, a phage lysate is generated. On a 10 ml preculture of LB inoculated in the morning from 200 µl of the overnight culture in the presence of 2 g/L of glucose and 5 mM $CaCl_2$, 200 µl of phage P1 are added. The culture is allowed to proceed over 2 h long enough for the cell lysis due to the phage. The reaction is stopped with 200 µl of chloroform. The whole is centrifuged for 10 mM at 4500×g and 9 ml of the phage containing supernatant recovered and stored with 200 µl of chloroform at 4° C. The receptor strain is precultured overnight. From this culture, 1.5 ml is recovered and centrifuged. The pellet is taken up in 600 µl of 10 mM $MgSO_4$+5 mM $CaCl_2$. The transduction is carried out by bringing together 100 µl of cells and 100 µl of the phage lysate. The whole is incubated for 30 minutes at 30° C. without stirring. Subsequently, 100 µl of 1M sodium citrate are added as well as 1 ml of LB. The phenotypic expression of the strains having integrated the kanamycine cassette occurs by allowing the cells to grow during 1 h at 37° C. under stirring. The cells are then spread on a LB medium dish containing the selection marker and allowed to grow overnight. The following day, the colonies formed are tested by PCR for the presence of the selection cassette and for the absence of the deleted gene.

Excision Protocol of Selection Cassette Flanked by FRT Sequence

The cassette is excised from the chromosome by using the FLP recombinase carried by the plasmid pCP20 (Cherepanov & Wackernagel, 1995) which leaves a scar region containing a FRT site. pCP20 is a plasmid carrying ampicillin and chloramphenicol resistance which presents a heat-sensitive replication and a heat-induced FLP recombinase expression. The marker-resistant mutants containing therefore the cassette are transformed with pCP20 and the ampicillin-resistant transformants carrying the plasmid resistance are selected at 30° C. Thereafter, they are cultured at 37° C. on solid LB and then tested for the ampicillin-resistance loss. The excision of the selection cassette is subsequently verified by PCR with the primers used for amplifying it with the Taq polymerase (NEB). The multiple deletions are obtained by repeating the operation.

Gene Cloning on Plasmid in *S. cerevisiae*

The gene cloning in *S. cerevisiae* utilizes the yeast genetic recombination capacities. The gene to be cloned is associated with a promoter sequence and a terminator sequence giving three fragments to be ligated in a plasmid previously linearized. To this end, 40 nucleotide homologous regions are designated on the primers. These 40 nucleotides of homology allow the recombination systems of the yeast to ligate all of the fragments after transformation. Each fragment is amplified by PCR using the polymerase Phusion™. All of the fragments and the linearized host vector are transformed in a *S. cerevisiae* competent strain according to the method described by Gietz and Woods (2002). After transformant growth, the plasmids are extracted according to the method described by Zeugin and Hartley (1985). The plasmids are then used to transform an *E. coli* DH10B strain. The plasmids are extracted from *E. coli*, verified by sequencing and used to transform the *S. cerevisiae* receptor strain.

Extraction of Plasmids in *S. cerevisiae*

After transformation, the resulting colonies are resuspended in water and then centrifuged for plasmid extraction. The cell pellet is resuspended in 400 µl of a buffer at 4° C. containing 50 mM glucose, 10 mM EDTA, 25 mM Tris-HCl pH 8 and supplemented with RnaseA 0.1 mg/ml. 400 µl of a solution containing 0.2 M NaOH and 1% SDS are used to lyse the cells. Glass beads are then added in an amount of one-third of the total volume and cells are vortexed at 4° C. for 10 minutes. This step is followed by a centrifugation at 13,000 RPM for 60 seconds. 700 µl of the supernatant are taken and put in a new tube of 2 ml. 325 µl of a 3M KAc solution at 4° C., pH 5.5, is added. The mixture is incubated for 10 mM on ice before being centrifuged for 10 mM at 13,000 RPM at 4° C. 700 µl of the supernatant are taken and placed in a new tube. 700 µl of isopropanol are added and the whole is strongly stirred before being incubated for 10 mM at room temperature. A centrifugation is then carried out at room temperature during 30 mM at 13,000 RPM. Thereafter, the supernatant is removed and the pellet is resuspended in 500 µl of 70% ethanol at −20° C. and then centrifuged for 5 min. The supernatant is removed. This step is repeated once again and then the pellet is dried until the ethanol has disappeared. The pellet is then taken up in 30 µl $H_2O$.

Generally, the primers used for the expression of the pathway in *E. coli* are listed in table 3, and the primers used for the expression of the pathway in *S. cerevisiae* are listed in table 4.

Expression and Purification of Proteins from a Plasmid pET28a

The pET28a containing *E. coli* strain BL21(DE3) carrying the gene of interest is cultured overnight at 37° C. in 100 ml of LB medium in a 500 ml Erlenmeyer under stirring at 200 RPM.

The following day, 10 to 50 ml of this pET28a containing *E. coli* BL21(DE3) preculture carrying the gene of interest are cultured in LB medium supplemented with 50 µg/ml of kanamycine at 37° C.

The protein expression is triggered by adding 1 mM IPTG to the cultures which reach an $OD_{600\ nm}$~0.7. After 3 h of incubation at 37° C., the cells are centrifuged and the pellets obtained are frozen at −80° C. For the purification of the protein thus expressed, cells are taken up in 1 ml of lysis buffer (50 mmol/l Hepes [pH 7.5], 3 mol/L NaCl, 0.25 mmol/l) and kept on ice for one hour.

Cells are then sonicated and debris removed by centrifugation at 13,000 RPM for 10 minutes at 4° C. Thereafter, a resin Talon™ is prepared with 0.3 mL of resin in 3 mL of lysis buffer. The whole suspension is then loaded on the resin and incubated at room temperature for 20 minutes before being centrifuged at 2500 RPM for 5 minutes at 4° C. The pellet is washed with 10 times the volume of resin with lysis buffer and incubated for 10 minutes at room temperature. The procedure is repeated with the lysis buffer which contains 15 mM imidazole. Then, the pellet is washed with 500 µl of 200 mM imidazole. The whole is recentrifuged at 2500 RPM during 5 minutes at 4° C. The supernatant is recovered, yielding the eluate 1. The procedure is repeated, yielding the eluate 2. The purified proteins are found in the different eluates which will be tested.

Analytical Methods

In order to determine the amount of the synthetic pathway products from the culture supernatants, a HPLC (Ultimate 3000, Dionex) fitted with an autosampler and an oven (Shimadzu CTO-20A) and coupled to the detector RID-10A (Shimadzu) and UV SPD-20A (Shimadzu) was used. The compounds were separated on a column Aminex HPX-87H (300 mm×7.8 mm) fitted with a pre-column (Aminex). Assays were performed at a temperature of 35° C. with a flow rate of 0.5 ml/min of 1.25 mM $H_2SO_4$. 20 μl samples were injected in the apparatus.

Example 1: Demonstration of the (D)-xylulose-1-kinase and (L)-ribulose-1-kinase Activities Cloning of the Candidate Xylulokinases: khkC, rhaB and fucK in pET28a The cloning of the khkC (SEQ ID No 1), rhaB (SEQ ID No 6) and fucK (SEQ ID No 5) genes in pET28a was carried out as indicated hereafter. The khk-C gene was digested from the pET11a-khk-C (Asipu et al., 2003) by NdeI/EcoRI. It was inserted by ligation thanks to the ligase T4 (Biolabs) following the tag-histidine of pET28a previously digested with the same enzymes. The rhaB and fucK cloning was carried out by amplifying rhaB and fucK by PCR from E. coli genomic DNA with the following primers, P1/P2, P3/P4, respectively, listed in table 3. The fragments were then cloned in the vector pGEM-T (Invitrogen). They were then digested by NcoI and BamHI and then ligated in the plasmid pET28a at the MCS previously digested with the same enzymes. The ligation product is transformed in an E. coli strain BL21(DE3). The vectors pET28-khk-C, pET28-rhaB, and pET28-fucK thus obtained were verified by sequencing whether they contain the genes with the correct sequences.

Determination of the Candidate (D)-Xylulokinase and (L)-Ribulokinase Kinetic Parameters The proteins were expressed and purified as previously described and the kinetic parameters of the enzymes were determined by the pyruvate kinase/lactate dehydrogenase coupling reaction based on the following principle (the given example corresponds to the dosing of a (D)-xylulose-1P aldolase activity):

Xylulose kinase: (D)-Xylulose+ATP→(D)-xylulose-1P+ADP

Pyruvate kinase: phosphoenolpyruvate+ADP→pyruvate+ATP

Lactate dehydrogenase: pyruvate+NADH→lactate+NAD

The reaction was performed in the following mixture: 0.4 mM NADH (Sigma), 2 mM PEP (Sigma), 4 mM ATP (Sigma) in a Hepes buffer (90 mM Hepes, 77 mM KCl, 12 mM $MgCl_2$, adjusted to pH 7 with a KOH solution). A 1.25 μl volume in pyruvate kinase/lactate dehydrogenase enzyme mixture (Sigma) is added in a total reaction mixture of 250 The reaction starts with the addition of 100 μl (D)-xylulose (Carbosynth) or 10 mM (L)-ribulose (Sigma). The NADH consumption was monitored by spectrofluorometer at 340 nm.

TABLE 1A

Kinetic parameters of the kinases on their natural substrate and on (D)-xylulose. The natural substrates of Khk-C, RhaB and FucK are fructose, rhamnulose and fuculose, respectively.

| | Natural substrate | | (D)-xylulose | |
|---|---|---|---|---|
| Candidate enzyme | Vmax [U/mg] | Km [mM] | Vmax [U/mg] | Km [mM] |
| Ketohexokinase Khk-C, H. sapiens | 6 | 0.72 | 3.1 | 0.6 |
| (L)-rhamnulose kinase RhaB, E. coli | nd | nd | 18.7 | ns |
| L-fuculokinase FucK, E. coli | 20 | 0.06 | 0.1 | ns |

These results show that kinases having the ability to phosphorylate the (D)-xylulose in position 1 can be identified.

The same approach was used to characterize these parameters on (L)-ribulose:

TABLE 1B

Kinetic parameters of the kinases on their natural substrate and on (L)-ribulose.

| | Natural substrate | | (L)-ribulose | |
|---|---|---|---|---|
| Candidate enzyme | Vmax [U/mg] | Km [mM] | Vmax [U/mg] | Km [mM] |
| Ketohexokinase, Khk-C, H. sapiens | 6.59 ± 1.4 | 0.31 ± 0.1 | 3.5 | 0.55 |

The Lhk-C is functional both on (D)-xylose and (L)-ribulose and has characteristics suitable for use in the synthetic pathway.

Example 2: Demonstration of the (D)-xylulose-1P-aldolase and (L)-ribulose-1P-aldolase Activities Cloning of the Genes Encoding the Candidate Aldolases AldoB, FbaB and AgaY The cloning of the candidate aldolases was done by amplifying aldoB, fbaB and agaY by PCR (using, respectively, the primer pairs P5/P6, P7/P8 and P11/P12 listed in table 3). This amplification was performed from the plasmid peX-A-aldoB carrying aldoB with codon optimization (Eurofins) or from the E. coli genomic DNA for fbaB and agaY, respectively. The fragments were then cloned in pGEM (Invitrogen). They were then digested by BamHI and HindIII (for aldoB) or NdeI and BamHI (for fbaB and agaY) and then ligated in the plasmid pET28a at MCS previously digested by BamHI and HindIII or NdeI and BamHI to clone aldoB (SEQ ID No 2) or fbaB (SEQ ID No 9) and agaY (SEQ ID No 8), respectively. The ligation product is transformed in the E. coli strain BL21(DE3). The vectors pET28-aldoB, pET28-fbaB, and pET28-agaY thus obtained were verified by sequencing whether they contain the genes with the correct sequences.

Determination of the Candidate (D)-xylulose-1-phosphate aldolase and (L)-ribulo-1-phosphate aldolase Kinetic Parameters The proteins were expressed and purified as previously described and the kinetic parameters of the enzymes were determined on (D)-fructose-1,6bP, (D)-xylulose-1P and (L)-ribulose-1P based on the following principle (the given example corresponds to the dosing of a (L)-ribulose-1P aldolase activity). (L)-ribulose-1 kinase: (L)-ribulose+ATP→(L)-ribulose-1P+ADP (L)-ribulose-1P aldolase: (L)-ribulose-1P→DHAP+glycolaldehyde Glycerol-3P dehydrogenase: DHAP+NADH→Glycerol-3P+NAD The reaction was performed in the following mixture: 0.4 mM NADH, 2 mM PEP, 4 mM ATP (all from Sigma) in a Hepes buffer (90 mM Hepes, 77 mM KCl, 6.8 mM MgCl$_2$, adjusted to pH 7 with a KOH solution). The purified Khk-C enzymes and GldA (Glycerol dehydrogenase from Cellulomonas sp. Sigma) are added in an amount of 15 µl of Khk-C (0.005 U) and 4 µl of 84 U/mg concentrated solution of GldA for a total reaction mixture of 250 The reaction was started by adding 100 µl of D-xylulose or 20 mM (L)-ribulose (Sigma). The NADH consumption was monitored by spectrofluorometer at 340 nm.

TABLE 2A

Kinetic parameters of aldolases on (D)-fructose-1,6 bisphosphate and on (D)-xylulose-1-phosphate.

| Candidate enzyme | (D)-Fructose-1,6bP | | (D)-Xylulose-1P | |
| --- | --- | --- | --- | --- |
|  | Vmax [U/mg] | Km [mM] | Vmax [U/mg] | Km [mM] |
| Fructose-16bP aldolase, Aldo-B, *H. sapiens* | 0.46 ± 0.05 | 0.03 ± 0.01 | 0.81 ± 0.2 | nd |
| Fructose-16bP aldolase, FbaB, *E. coli* | 0.52 ± 0.1 | 0.33 ± 0.07 | 0.18 ± 0.04 | nd |

TABLEAU 2B

Kinetic parameters of aldolases on (D)-fructose-1,6 bisphosphate and on (L)-ribulose-1-phosphate.

| Candidate enzyme | (D)-Fructose-1,6bP | | (L)-Ribulose-1P | |
| --- | --- | --- | --- | --- |
|  | Vmax [U/mg] | Km [mM] | Vmax [U/mg] | Km [mM] |
| Fructose-16bP aldolase Aldo-B, *H. sapiens* | 0.46 ± 0.05 | 0.03 ± 0.01 | 0.00 | nd |
| Fructose-16bP aldolase FbaB, *E. coli* | 0.52 ± 0.1 | 0.33 ± 0.07 | 0.06 ± 0.01 | nd |

AldoB has an activity on (D)-xylulose-1-P and can thus be used in the synthetic pathway for xylose assimilation. FbaB has an activity on (D)-xylulose-1P and (L)-ribulose-1P and can thus be used to construct a synthetic pathway for (D)-xylose or (L)-arabinose assimilation.

Example 3: In Vitro Functioning of the Synthetic Metabolic Pathway for Pentose Assimilation In Vitro Functioning of the Synthetic Metabolic Pathway for (D)-Xylose Assimilation The metabolic pathway for (D)-xylose assimilation has been reconstituted in vitro using purified enzymes (commercial and expressed and then purified from *E. coli*) from (D)-xylulose to demonstrate its functioning by producing ethylene glycol (FIG. 1).

The enzymes used for implementing the synthetic metabolic pathway were the following:
  Khk-C (Ketohexokinase/*H. sapiens*), encoded by the khkC gene of sequence SEQ ID NO:1 or KHK-A (Prospecbio);
  Aldolase B (AldoB/*H. sapiens*), encoded by the aldoB gene of sequence SEQ ID NO:2 or rabbit aldolase (Sigma-Aldrich-A2714);
  Glycerol dehydrogenase Cellulomonas sp. (Sigma-aldrich/G3512-250U).

The reaction medium comprised the Hepes buffer (90 mM Hepes; 77 mM KCl; 6.8 mM MgCl$_2$) at pH=7; 4 mM ATP; 0.4 mM NADH; 0.005 Unit/ml Khk-A (Prospecbio) or Khk-C (purified from pET28a); 1 Unit/ml aldolase (AldoB, Sigma A6338), and 1 Unit/ml GldA (Sigma-G3512-250U). The reaction was started by adding 5 mM D-xylulose (Cabosynth). After an incubation time of 3 h, the ethylene glycol produced during the reaction was quantified by HPLC (FIG. 2).

The appearance of ethylene glycol in the reaction which contains the (D)-xylulose-1-kinase, the (D)-xylulose-1P aldolase and the glycolaldehyde reductase demonstrates the synthetic pathway functioning.

In Vitro Functioning of the Metabolic Pathway for (L)-Arabinose Assimilation

The metabolic pathway for (L)-arabinose assimilation has been reconstituted in vitro using purified enzymes (commercial and expressed and then purified from *E. coli*) from (L)-ribulose.

The pathway functioning was verified by HPLC measurement of the ethylene glycol produced.

The enzymes used for implementing the synthetic metabolic pathway were the following:
  Khk-C (Ketohexokinase/*H. sapiens*), encoded by the khkC gene of sequence SEQ ID NO:1;
  FbaB (Fructose 1,6-bisphosphate aldolase, *E. coli*) encoded by the fbaB gene of sequence SEQ ID NO:9;
  GldA (Glycerol dehydrogenase Cellulomonas sp. (Sigma-aldrich/G3512-250U).

Enzymes were incubated in the reaction medium containing: 0.4 mM NADH, 4 mM ATP, Hepes buffer pH 7 (55 mM Hepes, 45 mM KCl, 4 mM MgCl$_2$ adjusted to pH 7 with KOH) for a final volume of 500 Khk-C was added at 0.005 Unit/ml while FbaB at 100 µg/ml. GldA was added at 1 U/ml. The reaction was started by adding 20 mM L-ribulose (Sigma-Aldrich). After an incubation time of 3 h, the ethylene glycol produced during the reaction was quantified by HPLC. The results are presented in FIG. 3.

The appearance of ethylene glycol in the reaction which contains the (L)-ribulose-1-kinase, the (L)-ribulose-1P aldolase and the glycolaldehyde reductase demonstrates the synthetic pathway functioning.

Example 4: In Vivo Functioning of the Synthetic Metabolic Pathway for (D)-Xylose Assimilation Gene Cloning of the Synthetic Pathway into Operon The *H. sapiens* genes khk-C encoding the C isoform of the ketohexokinase enzyme (Khk) of sequence SEQ ID NO:1, and aldoB encoding the B isoform of the fructose-1,6 aldolase of sequence SEQ ID NO:2 were cloned into operon on a plasmid pEXT20 (Dykxhoorn, (1996)) under the control of an IPTG-inducible promoter constructed as follows. The human khk-C gene was provided by Dr. Asipu (Asipu et al., 2003) and amplified with the primers P13 and P14 (Table 3). The aldolase was synthesized with codon optimization for *E. coli* by Eurofins™ and amplified by PCR with the primers P15 and P16 (Table 3). The primers for the amplification of the two genes were designed to give PCR fragments that can be used with the Clonetech In-Fusion kit by adding a tail having 17 nt of homology with the adjacent fragment. A canonic RBS (AGGAGG) was added to the khk-C and aldoB sequences. The plasmid pEXT20 was digested with the BamHI and SacI restriction enzymes. The Clonetech In-Fusion kit was used to ligate the two PCR fragments by recombination and the pEXT20 linearized, giving the plasmid pEXT20-khk-C-aldoB. The pEXT20-khk-C-aldoB vector thus obtained was verified by sequencing whether it contains the genes with the correct sequences. This plasmid was transformed in a ΔxylB strain of *E. coli* MG1655, in which xylB, of sequence SEQ ID NO:53, encoding the xylulose-5-kinase was deleted. The two genes khk-c and aldoB were also individually cloned on pEXT20 by first being amplified by P60 and P61, and P62 and P63, respectively, and then ligated in pEXT20 by restriction with BamHI and SalI enzymes, giving the plasmids pEXT20-khk-C and pEXT20-aldoB.

Synthetic Pathway Test by Monitoring the Growth of a ΔxylB Strain on (D)-Xylose

Bacterial growth as well as ethylene glycol production was tested in liquid medium M9 comprising 120 mM (D)-xylose as the sole carbon source, in the presence of IPTG.

To control the ability of strains not having the natural assimilation pathway of (D)-xylose to grow in the presence of (D)-xylose, the strains MG1655, MG1655 ΔxylB and MG1655 ΔxylB carrying pEXT20-khk-C, pEXT20-aldoB or pEXT20-khk-C-aldoB were tested.

Without the synthetic pathway, only the wild strain grows in these conditions. The loss of XylB does not allow the growth on xylose. In addition, neither the presence of Khk-C nor the presence of AldoB restores a growth by using the natural pathway for xylose assimilation (FIG. 4). In contrast, the MG1655 ΔxylB strain, carrying the plasmid pEXT20-khkC-aldoB, was able to grow on xylose.

By monitoring the metabolite production by HPLC during the growth, ethylene glycol was identified as a main product of xylose fermentation via the synthetic pathway with a yield of 0.45 mol per mol xylose (0.19 g EG per g xylose) (FIG. 5).

The synthetic pathway for (D)-xylose assimilation is therefore operational in vivo and restores the growth of a mutant ΔxylB in this sugar.

Example 5: Identification of the Main Glycolaldehyde Reductase

Ethylene glycol production optimization depends on the identification and overexpression of the glycolaldehyde reductase responsible of the conversion of glycolaldehyde into ethylene glycol. Several oxidoreductases with an activity on glycolaldehyde naturally occurring in *E. coli*, GldA, YqhD, FucO, DkgA, DkgB, YghZ, YeaE, YajO were identified (Lee et al., 2013). Mutants of these genes were recovered from the KEIO collection to determine whether one of these genes encodes the main glycolaldehyde reductase. For this purpose, the ability of these mutants to generate ethylene glycol from glycolaldehyde is tested. These Strains were grown in M9 medium in the presence of 133 mM xylose and when the $OD_{600\ nm}$ reaches 1, cells were exposed to 10 mM glycolaldehyde.

The amount of ethylene glycol was then measured by HPLC after 12 h of culture.

The absence of YqhD drastically diminishes the production of ethylene glycol from glycolaldehyde (FIG. 6) suggesting that it is the main glycolaldehyde reductase in *E. coli* in our culture conditions.

Example 6: Optimization of the Strain for the Production of Ethylene Glycol by the Synthetic Pathway of the Invention To improve ethylene glycol production, the main glycolaldehyde reductase is overexpressed on a plasmid pACT3.

To this end, yqhD (SEQ ID NO:4) was amplified with P11 and P12 and then cloned by In-Fusion in pACT3 previously digested with PstI and HindIII. The insertion of yqhD in linearized pACT3 was carried out by recombination using the In-Fusion kit (Clonetech), yielding the plasmid pACT3-yqhD. The vector pACT3-yqhD thus obtained was checked by sequencing. The ligation product was then transformed in the MG1655 strains of interest. Similarly, gldA (SEQ ID 51) and fucO (SEQ ID 52) (amplified by P24 and P25; and P26 and P27, respectively), were cloned by In-Fusion in pACT3 previously digested with PstI and HindIII in order to test their effect.

In our culture conditions, the main reductase of glycolaldehyde is YqhD but neither its overexpression nor that of the other reductases GldA and FucO increases ethylene glycol production. Indeed, the yield is only 0.45 mol/mol of xylose (0.19 g EG per g xylose), a yield comparable to that of the MG1655 ΔxylB strain which expresses the plasmid pEXT20-khkC-aldoB (FIG. 7).

To increase ethylene glycol production, the oxidation pathway of the glycolaldehyde into glycolic acid must be blocked. To this end, the impact of the deletion of the aldehyde dehydrogenase gene AldA (SEQ ID NO:3) was tested. To quantify the residual production of glycolic acid, the re-consumption of this acid was blocked by inactivating the glycolate dehydrogenase (see example 7) by the deletion of its GlcD subunit (encoded by the gene of sequence SEQ ID NO:7). The deletions of aldA and/or glcD in a ΔxylB strain were therefore undertaken by transduction from a KEIO strain. These constructions provide the MG1655 ΔxylB ΔaldA and MG1655 ΔxylB ΔaldA ΔglcD strains which are then transformed by pEXT20-khkC-aldoB.

Through the deletion of aldA, the EG yield greatly increases. Indeed, the MG1655 ΔxylB ΔaldA strain carrying the plasmid pEXT20-khkC-aldoB produces ethylene glycol to a yield of 0.88 mol per mol xylose (0.36 g EG per g xylose) (FIG. 7). The overexpression of YqhD and FucO in these conditions provides a yield of 0.9 and 0.94 mol/mol, respectively (0.38 and 0.39 g EG per g xylose, respectively). This is very close to the expected maximum theoretical yield which is 1 mol/mol.

Example 7: Optimization of the Strain for the Production of Glycolic Acid by the Synthetic Pathway for D-Xylose Assimilation To increase glycolic acid production via the synthetic pathway for pentose assimilation, *E. coli* glycolaldehyde dehydrogenase AldA was overexpressed. To this end, aldA was amplified from the genomic DNA of *E. coli* MG1655 by using the primer pair (P17 and P18, Table 3) and the fragment obtained was ligated in pGEM-T (Promega) according to the manufacturer's instructions. The fragment was then digested with KpnI and HindIII enzymes and then ligated in pACT3 itself linearized by the same enzymes. The pACT3-aldA vector thus obtained was verified by sequencing whether it contains the gene with the correct sequence. Thereafter, pACT3-aldA was transformed in the MG1655 ΔxylB pEXT20-khk-C-aldoB strain yielding the ΔxylB pEXT20-khk-C-aldoB pACT3-aldA strain. When culturing this strain on M9 medium+10 g/xylose, the ethylene glycol production significantly decreased (yield of 0.2 mol/mol) but the production of glycolic acid only increased transiently indicating the re-consumption of the glycolic acid produced (FIG. 8).

To prevent the re-consumption of glycolic acid, the glycolate oxidase encoded by glcDEF was attenuated. To this end, the MG1655 ΔxylB ΔglcD strain was constructed by deleting glcD (SEQ ID NO:7) via transduction of the mutation from a strain of the KEIO collection. The MG1655 ΔxylB ΔglcD strain was transformed with pEXT20-khkC-aldoB, or pEXT20-aldA-khkC-aldoB plasmids. This plasmid was constructed from pEXT20-khkC-aldoB cleaved with the EcoRI and SmaI restriction enzymes to which was cloned, by the In-Fusion method, aldA gene with an upstream RBS. This gene was itself amplified by PCR using the P24 and P25 primers. When culturing this strain containing pEXT20-khkC-aldoB on a medium M9-xylose (10 g/l), the glycolic acid production significantly increased and reached a yield of 0.35 mol/mol (0.19 g AG per g xylose) (FIG. 8). When aldA is overexpressed from pEXT20, the yield reaches 0.92 mol/mol of xylose (0.47 g AG per g xylose).

glcD deletion allows an accumulation of glycolic acid due to the overexpression of aldA by using 92% of the carbon flow derived from the C2 part of the xylose.

Example 8: Optimization of the Strain for the Production of Glycolic Acid Via the Glyoxylate Cycle The glycolic acid production can be further increased by combining the functioning of the optimized synthetic pathway as described above with genetic interventions leading to the production of glycolic acid via the glyoxylate pathway as described in the patents: US20090155867 (Soucaille, 2009) and US20120315682 (Dischert et al., 2012). Based on these published data, the aceB and glcB genes, encoding malate synthases, the glc gene encoding the glyoxylate carboligase, the arcA gene encoding a repressor of the aerobic response and the icd gene encoding an isocitrate dehydrogenase were deleted by the P1 phage transduction protocol in the MG1655 strain. The glcDEFG operon encoding a glycolate oxidase, edd-eda encoding a phosphogluconate dehydratase and the Entner-Doudoroff Aldolase, respectively, as well as iclR encoding the transcriptional repressor of the glyoxylate pathway, were deleted through the Datsenko's deletion method (Datsenko et al., 2000) by using the P52 and P53 and P54 and P55 and 64 and 65 primers, respectively. Plasmids for the parallel overexpression of the isocitrate lyase, encoded by aceA, and the glyoxylate reductase, encoded by ghrA (or ycdW) were constructed to improve the production of glycolic acid via the Krebs and the glyoxylate cycles. To this end, a pACT3 plasmid was digested with BamHI and HindIII enzymes. The ghrA gene was amplified by PCR as previously described, using the primer pair P40 and P41 while the aceA gene was amplified by the primer pair P21 and P22. The two amplified fragments and the linearized plasmid were ligated together by using the In-Fusion kit (Clonetech). This construction yielded the plasmid pACT3-ghrA-aceA.

This plasmid is then transformed in the strain carrying the ΔaceB ΔglcDEFGB Δgcl Δedd-eda ΔiclR ΔarcA Δicd deletions. The resulting strain is the strain 1054. When this strain is cultured on M9+glucose, 1.17 mol/mol of glycolic acid (0.49 g AG per g glucose) are produced without acetate production (Table 6).

TABLE 6

Production of glycolic acid and acetate of ΔaceB ΔglcDEFGB Δgcl Δedd-eda ΔiclR E. coli strains with additional mutations in M9 medium + 1% glucose

| Strain | Additional mutations | Plasmids | AG [mol/mol] | AG [g/g] | Acetate mol/mol |
|---|---|---|---|---|---|
| 1052 | — | pACT3-ghrA aceA | 0.15 ± 0.03 | 0.06 ± 0.01 | 0.02 |
| 1053 | ΔarcA | pACT3-ghrA aceA | 0.15 ± 0.02 | 0.06 ± 0.01 | 0.00 |
| 1054 | ΔarcA Δicd | pACT3-ghrA aceA | 1.17 | 0.49 | 0.00 |

Example 9: Optimization of the Strain for the Production of Glycolic Acid Via the Co-Utilization of Glyoxylate Cycle and Synthetic Pathway for (D)-Xylose Assimilation on Glucose and D-Xylose For applying the synthetic pathway for xylose assimilation described in this document, it is preferred to carry out the glycolic acid production on cellulosic or hemicellulosic hydrolysates which typically contain glucose and xylose in different percentages. To demonstrate that the yield of glycolic acid on a substrate containing both the glucose and xylose sugars may be increased through the simultaneous production of glycolic acid via the synthetic pathway and via the glyoxylate cycle, a strain which co-expresses simultaneously the two pathways was constructed. The E. coli ΔxylB ΔaceB ΔglcDEFGB Δgcl Δedd-eda ΔiclR ΔarcA Δicd strain is co-transformed by the plasmids pACT3-ghrA-aceA and pEXT20-khk-c-aldoB-aldA. The strain thus obtained is the strain 905. The glycolic acid production monitoring by HPLC was carried out during the growth of this strain on mineral medium M9+0.1% yeast extracts+0.2% tryptone and in the presence of 0.25% glucose and 0.5% xylose (FIG. 9).

TABLE 7

Glycolic acid production of E. coli strains in M9 medium + 2.5 g/l glucose + 5 g/l (D)-xylose + 1 g/l yeast extract + 2 g/l tryptone. proD:galP-galP overexpressed with the constitutive promoter proD (Davis et al., 2011)(**) Yield calculated based on the total sugar consumed.

| Strain | Genotype | Plasmids | AG** [g/g] |
|---|---|---|---|
| 1054 | ΔaceB ΔglcDEFGB Δgcl Δedd-eda ΔiclR ΔarcA Δicd | pACT3-aceA ghrA | 0.4 |
| 1044 | ΔaceB ΔglcDEFGB Δgcl Δedd-eda ΔiclR ΔarcA Δicd | pACT3-aceA ghrA pEXT20-khkC-aldoB-aldA | 0.43 |
| 905 | ΔxylB ΔaceB ΔglcDEFGB Δgcl Δedd-eda ΔiclR ΔarcA Δicd | pACT3-aceA ghrA pEXT20-khkC-aldoB-aldA | 0.51 |
| 979 | ΔxylB ΔaceB ΔglcDEFGB Δgcl Δedd-eda ΔiclR ΔarcA Δicd proD:galP | pACT3-aceA ghrA pEXT20-khkC-aldoB-aldA | 0.66 |

The strain first consumes the glucose and then the xylose despite the absence of XylB showing that the synthetic pathway is active even in these conditions. After 100 h of culture, 2.35 g/L of glycolic acid are produced by the strain with a yield on the total sugar used of 0.51 g/g (table 7). This yield is higher than that obtained with a quasi-isogenic strain that did not have the synthetic pathway for (D)-xylose assimilation (table 7, strain 1054), or did not carry the deletion of the xylB gene which encodes the enzyme that catalyzes the entry into the natural pathway for (D)-xylose assimilation (table 7, strain 1044).

The xylose assimilation rate after the total consuming of the glucose remained relatively low with a value of about 0.19 mmol/(1 h). To accelerate the xylose assimilation, the expression of the sugar permease galP was made constitutive by using the following method: a DNA fragment encoding the constitutive promoter proD described by Davis (Davis et al., 2011) and synthesized by Eurofins (SEQ ID 90) was amplified with P56 and P57 primers. Expression cassette of the kan gene was amplified using the P58 and P59 primers and the plasmid pKD4 (SEQ ID 95) as a template. The two PCR fragments were fused by an overlap extension PCR using the P59 and P57 primers. The PCR product thus obtained was transformed in the strain 905 with the method of Datsenko and Wanner (Datsenko et al., 2000). Kanamycine-resistant clones were recovered and verified as containing the synthetic and constitutive promoter before galP.

The new strain thus obtained is co-transformed by pACT3 aceA-ghrA and pEXT20-khk-C-aldoB-aldA yielding the strain 979. Its growth and the production monitoring of glycolic acid by HPLC were performed on a mineral medium M9+0.1% yeast extract+0.2% tryptone and in the presence of 0.25% glucose and 0.5% xylose (FIG. 10).

The strain builds up 3.84 g/L glycolic acid in a yield of 0.66 g/g on total sugar. The xylose assimilation rate after the total consuming of the glucose was increased through the overexpression of GalP and reaches a value of 0.32 mmol/1 (1 h).

Example 10: Expression of the Synthetic Pathway for Xylose Assimilation in *Saccharomyces cerevisiae*

To test the portability of the synthetic pathway for xylose assimilation, we tested its expression in another microorganism of interest, the *Saccharomyces cerevisiae* yeast.

*S. cerevisiae* does not have natural enzymatic system to convert (D)-xylose into (D)-xylulose and therefore, is not able to grow on this sugar. Two metabolic pathways are typically expressed heterologously in this yeast to achieve the conversion of (D)-xylose into (D)-xylulose and to enhance its growth on xylose. The xylose isomerase (XI) catalyzes the conversion of xylose into xylulose directly and in a redox-neutral way. Alternatively, the sequential action of the xylose reductase (XR) and the xylitol dehydrogenase (XDH) also enables a conversion of xylose into xylulose by using NADPH and NAD cofactors, respectively. To show the functioning of the synthetic pathway for xylose assimilation in yeast, this synthetic pathway was complemented either by a xylose isomerase or by the XR/XDH system.

To complement the synthetic pathway for xylose assimilation with a XI, the XI of *Clostridium phytofermentans*, codon-optimized for *S. cerevisiae*, designed by the team of Eckhard Boles (Brat et al., 2009), was used. khk-C was expressed under the control of the triose phosphate isomerase Tpi promoter (Ptpi: SEQ ID NO:15) and used the Trk1 terminator (SEQ ID NO:12).

The aldolase AldB gene was placed under the control of the *S. cerevisiae* natural aldolase promoter (pFab: SEQ ID NO:14) and a terminator Tlk1 (SEQ ID NO:13) was also used.

These genes were cloned by recombination in the yeast in the plasmid p425 linearized with KpnI and HindIII yielding p425-khk-aldoB by using the following primers (see also table 4): P1' and P2' for Ptpi, P3' and P4' for khk-C, P5' and P6' for Trk1, P7' and P8' for pFab, P'9 and P'10 for aldoB and P'11 and P'12 for tlk1.

The plasmid p425-khk-aldoB was then used in a competent strain unable to grow on xylose because it was mutated for its natural xylulose kinase, Xks1 (SEQ ID 89).

A co-transformation with a plasmid constructed by the team of Eckhard Boles containing both the xylulose isomerase and a transporter xylose Gal-2 was thus carried out in the strain CEN.PK-2 xks1-.

The ability of the strain to grow in a minimum medium containing only xylose was tested (FIG. 11).

In this case, while the mutant xks1 is unable to grow on D-xylose, the mutant xks1 carrying the synthetic pathway has restored his growth indicating that the pathway is operational in the yeast.

The use of a XI is not the only possible way to assimilate xylose by converting it into xylulose. Indeed, as a result of a reduction reaction catalyzed by a xylose reductase (XR) and of a dehydrogenation of the xylitol thus obtained catalyzed by a xylitol dehydrogenase (XDH), xylulose is obtained. We used therefore the TMB3001 strain (Eliasson et al., 2000) expressing the XR/XDH system to test if the synthetic pathway is capable of being used in these conditions to assimilate the xylose. A mutant xks1⁻ was constructed in the TMB3001 strain by transforming a PCR fragment containing flaking edges homologous to the non-coding ends of xks1 to generate a deletion by homologous recombination. The PCR fragment is amplified from the BY strain of the Yeast collection knockout (YKO) (Winzeler et al. 1999) with the primers P26' and P27' and contains a kanMX cassette for recombinant selection. The synthetic pathway is expressed in the plasmid pYCP-khk-C-aldoB constructed as follows. The plasmid pYCP-TPS1 (SEQ ID NO:80) was digested with AgeI and XbaI to extract therefrom the TPS1 cassette. Fw pTpi and rev Tlk1 primers are designed to have a floating tail of 40 nucleotides homologous to the plasmid pYCP linearized with AgeI and XbaI in order to recombine together in the plasmid. Then, we expressed khk-C codon optimized for the yeast (SEQ ID NO:83) amplified by P15' and P16' under the control of the promoter of triose phosphate isomerase Tpi (amplified by P13' and P14') and the terminator Trk1 (amplified by P17' and P18'), and expressed aldolase aldoB codon optimized for the yeast (SEQ ID NO:84) amplified by P21' and P22' under the control of the promoter of the *S. cerevisiae* natural aldolase pFbaB1 (amplified by P19' and P20') and the terminator Tlk1 (amplified by P23' and P24'). These constructions were cloned by recombination in yeast in the plasmid pYCP yielding pYCP-khk-C-aldoB. This plasmid was subsequently used in the TMB3001 xks1⁻ strain unable to grow on xylose because it was mutated for the xylulose kinase, Xks1.

While a mutant TMB3001 xks1⁻ lost its ability to grow on xylose unlike the TMB3001 strain, the TMB3001 xks1⁻ strain carrying pYCP-khk-C-aldoB restores its growth on xylose (FIG. 12). This suggests that the synthetic pathway is also operational in a strain assimilating the xylose via the XR/XDH system.

Example 11: In Vivo Functioning of the Synthetic Metabolic Pathway for (L)-Arabinose Assimilation Gene Cloning of the Synthetic Pathway into Operon The *H. sapiens* genes khk-C, encoding the C isoform of the ketohexokinase enzyme (Khk) of sequence SEQ ID NO:1, and fbaB encoding the *E. coli* fructose-1,6-bisphosphate aldolase B isoform of sequence SEQ ID NO:9 were cloned into operon on a plasmid pEXT20 (Dykxhoorn et al., 1996) under the control of a IPTG-inducible promoter constructed as follows. The human khk-C gene was provided by Dr. Asipu (Asipu et al., 2003) and amplified with the primers P13 and P14 (Table 3). The aldolase was amplified from E. coli genomic DNA of the MG1655 strain with the primers P28 and P29 (Table 3).

The primers for amplifying these two genes were designed to provide PCR fragments that can be used with the Clonetech In-Fusion kit by adding a tail having 17 nucleotides homology with the adjacent fragment. RBS were selected using the software RBS calculator (Salis et al., 2011). The fbaB gene is therefore preceded by a RBS of sequence (TTAGGAGGTATACT) predicted to provide maximum expression and khk-C is preceded by a RBS of sequence (ACAGCTTTTAATTATACACTT-TAAGGAGGACAGAC) predicted to minimize expression. The primers for amplifying the two genes with the new RBS (P30 and P22 for khk-C and P31 and P32 for fbaB) were designed to provide PCR fragments that can be used with the fusion kit by adding a tail having 15 nucleotides homology with the adjacent fragment. The plasmid pEXT20 was digested with the restriction enzymes BamHI and SalI. The Clonetech In-Fusion kit was used to ligate by recombination the two PCR fragments and the pEXT20 linearized to provide the plasmid pEXT20-khk-C-RBSmax-fbaB. The plasmid pEXT20-khk-C-RBSmax-fbaB is transformed in MG1655 ΔaraB. The vector pEXT20-khk-C-RBSmax-fbaB thus obtained was checked by sequencing. Similarly, the plasmids pEXT20-khk-C and pEXT20-fbaB were constructed using the primers 83/84 and 33/34 (Table 3) by In-Fusion. These plasmids were transformed in an E. coli MG1655 ΔaraB strain, wherein araB, of sequence SEQ ID 88, encoding the ribulo-5-kinase is deleted.

Synthetic Pathway Test by a ΔaraB Strain Growth Monitoring on (L)-Arabinose

The bacterial growth was tested in M9 liquid medium comprising 60 mM (L)-arabinose as a sole carbon source, in the presence of IPTG. To control the ability of strains lacking the natural pathway for arabinose assimilation to grow in the presence of (L)-arabinose in M9 medium, the following strains: MG1655 ΔaraB and MG1655 ΔaraB carrying the plasmids pEXT20-khk-C, pEXT20-fbaB, or pEXT20-khk-C-RBSmax-fbaB were tested. A preculture overnight in LB+100 µM IPTG+2% L-arabinose was carried out and then cells were transferred on M9 medium+2% glucose+2% arabinose+100 µM IPTG at $OD_{600\ nm}$=0.2 and then at $OD_{600\ nm}$=1, cells were transferred in M9 medium+ 2% L-arabinose+100 µM IPTG at $OD_{600\ nm}$=0.2. Only the strain expressing simultaneously KhkC and FbaB enzymes, having (L)-ribulose-1 kinase and (L)-ribulose-1P aldolase activities, respectively, grows in these conditions (FIG. 13). These results demonstrate the functioning of the synthetic metabolic pathway for (L)-arabinose assimilation.

TABLE 3

Primers used for the pathway expression in E. coli

| AA | Primers | SEQ ID |
|---|---|---|
| P1 | YC-49 rhaB fw-ndeI | 16 |
| P2 | YC-50 rhaB rev-BamHI | 17 |
| P3 | FucokinasefwNcoI | 18 |
| P4 | FucokinaserevBamHISalI | 19 |
| P5 | AldoB_BamHI_Fw | 20 |
| P6 | AldoB_Hind3_Rv | 21 |

TABLE 3-continued

Primers used for the pathway expression in E. coli

| AA | Primers | SEQ ID |
|---|---|---|
| P7 | fbaB-NdeI-fw | 22 |
| P8 | fbaB-BamHI-rev | 23 |
| P9 | agaY-NdeI-fw | 24 |
| P10 | agaY-BamHI-rev | 25 |
| P11 | YC73-Fw YqhD | 26 |
| P12 | YC74-Rev YqhD | 27 |
| P13 | YC52-fwkhkfu | 28 |
| P14 | YC53-revkhkfu | 29 |
| P15 | YC-76 fw AldoB | 30 |
| P16 | YC-75 fw AldoB | 31 |
| P17 | aldA_KpnI_Fw | 32 |
| P18 | aldA_Hind3_Rv | 33 |
| P19 | pACT ycdW-Fw | 34 |
| P20 | pACT ycdW-Rev | 35 |
| P21 | Operon aceA-Fw | 36 |
| P22 | pACT aceA-Rev | 37 |
| P23 | Operon ycdW-Rev | 38 |
| P24 | gldA_rbs_f | 54 |
| P25 | gldA_rbs_r | 55 |
| P26 | fucO_fw_inf | 56 |
| P27 | fucO_rev_inf | 57 |
| P28 | FbaB_oper_BamHI_F | 58 |
| P29 | FbaB_oper_SalI_R | 59 |
| P30 | khkrbsweak fw | 60 |
| P31 | fbabrbsmax fw | 61 |
| P32 | fbabrbsmax rev | 62 |
| P33 | FbaB inf BamHI F | 63 |
| P34 | FbaB inf Hind R | 64 |
| P40 | pACTaceA-Rev | 65 |
| P41 | Op aceA ghrA-Fw | 66 |
| P42 | pACT3 ghrA_XbaI-Rev | 67 |
| P51 | pACTghrA_XbaI-Rev | 68 |
| P52 | glcDEFGB_fw | 69 |
| P53 | glcDEFGB_rev | 70 |
| P54 | edd eda_fw | 71 |
| P55 | edd eda_rev | 72 |
| P56 | prom galP* fw | 73 |
| P57 | prom galP* rev | 74 |
| P58 | disruption k7 fw | 75 |
| P59 | disruption k7 rev | 76 |
| P60 | KHK-Cfw | 77 |
| P61 | KHK-Crev | 78 |
| P62 | AldoB_RBS_BaHI_F | 79 |
| P63 | RevAldoB | 80 |
| P64 | iclR-fw3 | 81 |
| P65 | iclR-rev2 | 82 |

TABLE 4

Primers used for the pathway expression in S. cerevisiae

| AA | Primers | SEQ ID |
|---|---|---|
| P1' | YC1_pTPI fw | 39 |
| P2' | YC2_pTPI Rev | 40 |
| P3' | YC3_khk-C fw | 41 |
| P4' | YC4_khk-C rev | 42 |
| P5' | YC5_ter trki fw | 43 |
| P6' | YC6_ter trki rev | 44 |
| P7' | YC7_pFBA1 fw | 45 |
| P8' | YC8_pFBA1 rev | 46 |
| P9' | YC9_aldoB fw | 47 |
| P10' | YC10_aldoB fw | 48 |
| P11' | YC11_Tlk1 terminator fw | 49 |
| P12' | YC12_Tlk1 terminator rev | 50 |
| P13' | fw tpi ycp | 83 |
| P14' | Rev tpi | 84 |
| P15' | Fw khk-C opt | 85 |
| P16' | Rev khk-C opt | 86 |
| P17' | Trk1 fw | 87 |
| P18' | Term-trk1 rev | 88 |
| P19' | pFba1 fw | 89 |

TABLE 4-continued

Primers used for the pathway expression in S. cerevisiae

| AA | Primers | SEQ ID |
|---|---|---|
| P20' | pfab1 rev | 90 |
| P21' | aldoB opt fw | 91 |
| P22' | aldoB opt rev | 92 |
| P23' | tlk1 fw | 93 |
| P24' | rev tlk1 ycp | 94 |
| P25' | fw deletion xks1 | 95 |
| P26' | rev deletion xks1 | 96 |

TABLE 5

Gene sequence listing

| Species | Gene | SEQ ID N° |
|---|---|---|
| H. sapiens | khkC | 1 |
| H. sapiens | aldoB | 2 |
| E. coli | aldA | 3 |
| E. coli | yqhD | 4 |
| E. coli | fucK | 5 |
| E. coli | rhaB | 6 |
| E. coli | glcD | 7 |
| E. coli | agaY | 8 |
| E. coli | fbaB | 9 |
| E. coli | ghrA | 10 |
| E. coli | aceA | 11 |
| S. cerevisiae | trk1 | 12 |
| S. cerevisiae | tlk1 | 13 |
| S. cerevisiae | pFab | 14 |
| S. cerevisiae | pTpi | 15 |
| E. coli | gldA | 51 |
| E. coli | fucO | 52 |
| E. coli | xylB | 53 |
| S. cerevisiae | Khk-C codon-optimized | 97 |
| S. cerevisiae | AldoB codon-optimized | 98 |
|  | YCP-Tps1 | 99 |
| E. coli | araB | 100 |
| S. cerevisiae | xks1 | 101 |
| E. coli | proD | 102 |

REFERENCES

Asipu, A., B. E. Hayward, J. O'Reilly, and D. T. Bonthron. 2003. "Properties of normal and mutant recombinant human ketohexokinases and implications for the pathogenesis of essential fructosuria." Diabetes 52 (9):2426-32.

Baba, T., T. Ara, M. Hasegawa, Y. Takai, Y. Okumura, M. Baba, K. A. Datsenko, M. Tomita, B. L. Wanner, and H. Mori. 2006. "Construction of Escherichia coli K-12 in-frame, single-gene knockout mutants: the Keio collection." Mol Syst Biol 2:2006.0008. doi: 10.1038/msb4100050.

Bais, R., H. M. James, A. M. Rofe, and R. A. Conyers. 1985. "The purification and properties of human liver ketohexokinase. A role for ketohexokinase and fructose-bisphosphate aldolase in the metabolic production of oxalate from xylitol." Biochem J 230 (1):53-60.

Brat, D., E. Boles, and B. Wiedemann 2009. "Functional expression of a bacterial xylose isomerase in Saccharomyces cerevisiae." Appl Environ Microbiol 75 (8):2304-11. doi: 10.1128/aem.02522-08.

Cherepanov, P. P., and W. Wackernagel. 1995. "Gene disruption in Escherichia coli: TcR and KmR cassettes with the option of Flp-catalyzed excision of the antibiotic-resistance determinant." Gene 158 (1):9-14.

Dagert, M., and S. D. Ehrlich. 1979. "Prolonged incubation in calcium chloride improves the competence of Escherichia coli cells." Gene 6 (1):23-8.

Datsenko, K. A., and B. L. Wanner. 2000. "One-step inactivation of chromosomal genes in Escherichia coli K-12 using PCR products." Proc Natl Acad Sci USA 97 (12): 6640-5. doi: 10.1073/pnas.120163297.

Davis, J. H., A. J. Rubin, and R. T. Sauer. 2011. "Design, construction and characterization of a set of insulated bacterial promoters." Nucleic Acids Res 39 (3):1131-41. doi: 10.1093/nar/gkq810.

Dischert, W., and P. Soucaille. 2012a. Method for producing high amount of glycolic acid by fermentation. Google patents.

Dischert, W., and P. Soucaille. 2012b. Method for producing high amount of glycolic acid by fermentation. Google patents.

Dykxhoorn, D. M., R. St Pierre, and T. Linn. 1996. "A set of compatible tac promoter expression vectors." Gene 177 (1-2):133-6.

Eliasson, A., C. Christensson, C. F. Wahlbom, and B. Hahn-Hägerdal. 2000. "Anaerobic xylose fermentation by recombinant Saccharomyces cerevisiae carrying XYL1, XYL2, and XKS1 in mineral medium chemostat cultures." Appl Environ Microbiol 66 (8):3381-6.

Gietz, R. D., and R. A. Woods. 2002. "Transformation of yeast by lithium acetate/single-stranded carrier DNA/polyethylene glycol method." Methods Enzymol 350:87-96.

Klamt, S., J. Saez-Rodriguez, J. A. Lindquist, L. Simeoni, and E. D. Gilles. 2006. "A methodology for the structural and functional analysis of signaling and regulatory networks." BMC Bioinformatics 7:56. doi: 10.1186/1471-2105-7-56.

Lee, C., I. Kim, and C. Park. 2013. "Glyoxal detoxification in Escherichia coli K-12 by NADPH dependent aldo-keto reductases." J Microbiol 51 (4):527-30. doi: 10.1007/s12275-013-3087-8.

Liu, H., K. R. Ramos, K. N. Valdehuesa, G. M. Nisola, W. K. Lee, and W. J. Chung. 2013. "Biosynthesis of ethylene glycol in Escherichia ca." Appl Microbiol Biotechnol 97 (8):3409-17. doi: 10.1007/s00253-012-4618-7.

Salis, H. M. 2011. "The ribosome binding site calculator." Methods Enzymol 498:19-42. doi: 10.1016/B978-0-12-385120-8.00002-4.

Soucaille, P. 2009. Glycolic Acid Production by Fermentation from Renewable Resources. Google patents.

Stephanopoulos, Gregory (4 Russet Lane, Winchester, Mass., 01890, US), Pereira, Brian (11 Everett Street, Apt. Ng4 Cambridge, Mass., 02138, US), DE MEY, Marjan (Ursulinen Straat 4/1, Gent, Gent, BE), Dugar, Deepak (69 Chestnut Street, Cambridge, Mass., 02139, US), Avalos, Jose, Luis (65 Walnut Street, Arlington, Mass., 02476, US). 2013. Engineering microbes and metabolic pathways for the production of ethylene glycol. Massachusetts Institute of Technology (77 Massachusetts Avenue, Cambridge, Mass., 02139, US Winzeler, E. A., D. D. Shoemaker, A. Astromoff, H. Liang, K. Anderson, B. Andre, R. Bangham, R. Benito, J. D. Boeke, H. Bussey, A. M. Chu, C. Connelly, K. Davis, F. Dietrich, S. W. Dow, M. El Bakkoury, F. Foury, S. H. Friend, E. Gentalen, G. Giaever, J. H. Hegemann, T. Jones, M. Laub, H. Liao, N. Liebundguth, D. J. Lockhart, A. Lucau-Danila, M. Lussier, N. M'Rabet, P. Menard, M. Mittmann, C. Pai, C. Rebischung, J. L. Revuelta, L. Riles, C. J. Roberts, P. Ross-MacDonald, B. Scherens, M. Snyder, S. Sookhai-Mahadeo, R. K. Storms, S. Véronneau, M. Voet, G. Volckaert, T. R. Ward, R. Wysocki, G. S. Yen, K. Yu, K. Zimmermann, P. Philippsen, M. Johnston, and R. W. Davis. 1999. "Functional characterization of the S. cerevisiae genome by gene deletion and parallel analysis." Science 285 (5429):901-6.

The invention claimed is:

1. Process for producing at least one of ethylene glycol and glycolic acid by converting pentose in a microorganism, said process comprising:

(i) an operation of culturing a recombinant microorganism expressing a synthetic pathway for pentose assimilation, the operation comprising at least the following steps:

a) phosphorylation in position 1 of a pentose comprising at least one of (D)-Xylulose, and (L)-Ribulose, wherein the phosphorylation is catalyzed by a recombinantly expressed kinase from said synthetic pathway, capable to phosphorylate in position 1 a pentose selected from (D)-Xylulose and/or (L)-Ribulose, b) cleavage of the pentose-1-phosphate obtained at the end of step a) in order to obtain glycolaldehyde and dihydroxyacetone phosphate (DHAP), wherein the cleavage is catalyzed by a recombinantly expressed aldolase from said synthetic pathway, capable to cleavage the pentose-1-phosphate in order to obtain glycolaldehyde and dihydroxyacetone phosphate (DHAP), and at least one of the following steps:

c) reduction of the glycolaldehyde obtained at the end of step b) to ethylene glycol, wherein the reduction is catalyzed by a recombinantly expressed glycolaldehyde reductase from said synthetic pathway, capable to catalyze reduction of the glycolaldehyde obtained at the end of step b) to ethylene glycol, and c') oxidation of the glycolaldehyde obtained at the end of step b) to glycolic acid, wherein the oxidation step c') is catalyzed by a recombinantly expressed glycolaldehyde dehydrogenase from said synthetic pathway, capable to catalyze an oxidation of the glycolaldehyde obtained at the end of step b) to glycolic acid, (ii) an operation of recovering said at least on of ethylene glycol and glycolic acid obtained at the end of the culturing operation (i).

* * * * *

SEQUENCE LISTING

<160> NUMBER OF SEQ ID NOS: 102

<210> SEQ ID NO 1
<211> LENGTH: 897
<212> TYPE: DNA
<213> ORGANISM: Homo sapiens

<400> SEQUENCE: 1

| | | |
|---|---|---|
| atggaagaga agcagatcct gtgcgtgggg ctagtggtgc tggacgtcat cagcctggtg | 60 |
| gacaagtacc ctaaggagga ctcggagata aggtgtttgt cccagagatg gcagcgcgga | 120 |
| ggcaacgcgt ccaactcctg caccgttctc tccctgctcg gagcccctg tgccttcatg | 180 |
| ggctcaatgg ctcctggcca tgttgctgac ttcctggtgg ccgacttcag gcggcgggc | 240 |
| gtggacgtgt ctcaggtggc ctggcagagc aaggggaca cccccagctc ctgctgcatc | 300 |
| atcaacaact ccaatggcaa ccgtaccatt gtgctccatg acacgagcct gccagatgtg | 360 |
| tctgctacag actttgagaa ggttgatctg acccagttca agtggatcca cattgagggc | 420 |
| cggaacgcat cggagcaggt gaagatgctg cagcggatag acgcacacaa caccaggcag | 480 |
| cctccagagc agaagatccg ggtgtccgtg gaggtggaga agccacgaga ggagctcttc | 540 |
| cagctgtttg gctacggaga cgtggtgttt gtcagcaaag atgtggccaa gcacttgggg | 600 |
| ttccagtcag cagaggaagc cttgagggc ttgtatggtc gtgtgaggaa aggggctgtg | 660 |
| cttgtctgtg cctgggctga ggagggcgcc gacgccctgg gccctgatgg caaattgctc | 720 |
| cactcggatg ctttcccgcc accccgcgtg gtggatacac tgggagctgg agacaccttc | 780 |
| aatgcctccg tcatcttcag cctctcccag gggaggagcg tgcaggaagc actgagattc | 840 |
| gggtgccagg tggccggcaa gaagtgtggc ctgcagggct tgatggcat cgtgtga | 897 |

<210> SEQ ID NO 2
<211> LENGTH: 1095
<212> TYPE: DNA
<213> ORGANISM: Homo sapiens

<400> SEQUENCE: 2

| | | |
|---|---|---|
| atggcacatc gctttccggc tctgacgcaa gaacagaaga agaattgtc agagattgcg | 60 |
| cagtccatcg tggcgaatgg caaaggtatt ctggccgcag atgagagcgt gggaaccatg | 120 |
| ggtaatcggc ttcaacgcat caaagtggag acaccgaag aaaatcggcg tcagtttcgc | 180 |
| gaaatcctct ttagcgtcga cagtagcatc aatcagtcca ttggcggggt gattctgttt | 240 |
| cacgaaacgc tgtaccagaa agactcgcaa gggaaactgt tccgcaacat tctgaaagag | 300 |
| aaaggcattg tggtgggcat caaactggat cagggtggcg cacccttagc tggcactaat | 360 |
| aaggagacaa cgattcaagg cctcgatggg ctttctgaac gttgtgccca gtataagaag | 420 |
| gatggtgttg actttggcaa atggcgcgcg gtactgcgta tcgctgatca gtgccctagc | 480 |
| agtctggcca ttcaggaaaa cgcgaatgcg ttagcacgct atgcgagcat tgccaacag | 540 |
| aacggcctgg ttcccattgt cgagccgaa gtaatcccgg atggcgatca tgacctggaa | 600 |
| cactgccagt atgtcaccga gaaagttctg gcggcggtgt ataaagccct gaatgaccat | 660 |
| cacgtgtact tggaaggtac cctcttgaaa ccgaacatgg taactgccgg acatgcctgc | 720 |
| accaagaaat acacccctga acaagtcgcc atggcaacag ttacggcttt acaccgcact | 780 |
| gttccagcgg cggttccggg tatttgcttc ctgtcaggtg gcatgtcgga agaagatgcc | 840 |
| accctcaacc tgaatgcgat caacttgtgt ccactgccga agccgtggaa actgtcattc | 900 |
| tcctatggac gtgcccttca ggccagtgcg ttagcggcat ggggtgggaa agcggcaaac | 960 |

```
aaagaagcta cccaggaagc cttcatgaaa cgtgcaatgg cgaactgtca agctgcgaaa    1020
ggccagtacg tccataccgg ttctagcggt gctgcatcga cacaatctct gtttacggcc    1080
tgttacacgt attaa                                                     1095
```

<210> SEQ ID NO 3
<211> LENGTH: 1440
<212> TYPE: DNA
<213> ORGANISM: Escherichia coli

<400> SEQUENCE: 3

```
atgtcagtac ccgttcaaca tcctatgtat atcgatggac agtttgttac ctggcgtgga     60
gacgcatgga ttgatgtggt aaaccctgct acagaggctg tcatttcccg catacccgat    120
ggtcaggccg aggatgcccg taaggcaatc gatgcagcag aacgtgcaca accagaatgg    180
gaagcgttgc ctgctattga acgcgccagt tggttgcgca aaatctccgc cgggatccgc    240
gaacgcgcca gtgaaatcag tgcgctgatt gttgaagaag ggggcaagat ccagcagctg    300
gctgaagtcg aagtggcttt tactgccgac tatatcgatt acatggcgga gtgggcacgg    360
cgttacgagg cgagattat tcaaagcgat cgtccaggaa aaatattct tttgtttaaa     420 cgtgcgcttg gtgtgactac cggcattctg ccgtggaact cccgttcttc ctcattgcc    480 cgcaaaatgg ctcccgctct tttgaccggt aataccatcg tcattaaacc tagtgaattt    540
acgccaaaca atgcgattgc attcgccaaa atcgtcgatg aaataggcct tccgcgcggc    600
gtgtttaacc ttgtactggg cgtggtgaa accgttgggc aagaactggc gggtaaccca    660
aaggtcgcaa tggtcagtat gacaggcagc gtctctgcag gtgagaagat catggcgact    720
gcggcgaaaa acatcaccaa agtgtgtctg gaattggggg gtaaagcacc agctatcgta    780
atggacgatg ccgatcttga actggcagtc aaagccatcg ttgattcacg cgtcattaat    840
agtgggcaag tgtgtaactg tgcagaacgt gtttatgtac agaaaggcat ttatgatcag    900
ttcgtcaatc ggctgggtga agcgatgcag gcggttcaat tggtaacccc cgctgaacgc    960
aacgacattg cgatggggcc gttgattaac gccgcggcgc tggaaagggt cgagcaaaaa    1020
gtggcgcgcg cagtagaaga aggggcgaga gtggcgttcg gtggcaaagc ggtagagggg    1080
aaaggatatt attatccgcc gacattgctg ctggatgttc gccaggaaat gtcgattatg    1140
catgaggaaa ccttggccc ggtgctgcca gttgtcgcat tgacacgct ggaagatgct     1200 atctcaatgg ctaatgacag tgattacggc ctgacctcat caatctatac ccaaaatctg    1260
aacgtcgcga tgaaagccat taagggctg aagtttggtg aaacttacat caaccgtgaa    1320
aacttcgaag ctatgcaagg cttccacgcc ggatggcgta atccggtat ggcggcgca    1380 gatggtaaac atggcttgca tgaatatctg cagacccagg tggtttattt acagtcttaa    1440
```

<210> SEQ ID NO 4
<211> LENGTH: 1164
<212> TYPE: DNA
<213> ORGANISM: Escherichia coli

<400> SEQUENCE: 4

```
atgaacaact ttaatctgca cacccccaacc cgcattctgt ttggtaaagg cgcaatcgct     60
ggtttacgcg aacaaattcc tcacgatgct cgcgtattga ttacctacgg cggcggcagc    120
gtgaaaaaaa ccggcgttct cgatcaagtt ctggatgccc tgaaaggcat ggacgtgctg    180
gaatttggcg gtattgagcc aaacccggct tatgaaacgc tgatgaacgc cgtgaaactg    240
```

-continued

| | |
|---|---|
| gttcgcgaac agaaagtgac tttcctgctg gcggttggcg gcggttctgt actggacggc | 300 |
| accaaattta tcgccgcagc ggctaactat ccggaaaata tcgatccgtg gcacattctg | 360 |
| caaacgggcg gtaaagagat taaaagcgcc atcccgatgg gctgtgtgct gacgctgcca | 420 |
| gcaaccggtt cagaatccaa cgcaggcgcg gtgatctccc gtaaaaccac aggcgacaag | 480 |
| caggcgttcc attctgccca tgttcagccg gtatttgccg tgctcgatcc ggtttatacc | 540 |
| tacaccctgc cgccgcgtca ggtggctaac ggcgtagtgg acgcctttgt acacaccgtg | 600 |
| gaacagtatg ttaccaaacc ggttgatgcc aaaattcagg accgtttcgc agaaggcatt | 660 |
| ttgctgacgc taatcgaaga tggtccgaaa gccctgaaag agccagaaaa ctacgatgtg | 720 |
| cgcgccaacg tcatgtgggc ggcgactcag gcgctgaacg gtttgattgg cgctggcgta | 780 |
| ccgcaggact gggcaacgca tatgctgggc acgaactga ctgcgatgca cggtctggat | 840 |
| cacgcgcaaa cactggctat cgtcctgcct gcactgtgga tgaaaaacg cgataccaag | 900 |
| cgcgctaagc tgctgcaata tgctgaacgc gtctggaaca tcactgaagg ttccgatgat | 960 |
| gagcgtattg acgccgcgat tgccgcaacc cgcaatttct ttgagcaatt aggcgtgccg | 1020 |
| acccacctct ccgactacgg tctggacggc agctccatcc cggctttgct gaaaaaactg | 1080 |
| gaagagcacg gcatgaccca actgggcgaa atcatgaca ttacgttgga tgtcagccgc | 1140 |
| cgtatatacg aagccgcccg ctaa | 1164 |

<210> SEQ ID NO 5
<211> LENGTH: 1419
<212> TYPE: DNA
<213> ORGANISM: Escherichia coli

<400> SEQUENCE: 5

| | |
|---|---|
| atgaaacaag aagttatcct ggtactcgac tgtggcgcga ccaatgtcag ggccatcgcg | 60 |
| gttaatcggc agggcaaaat tgttgcccgc gcctcaacgc taatgccag cgatatcgcg | 120 |
| atggaaaaca cacctggca ccagtggtct ttagacgcca ttttgcaacg ctttgctgat | 180 |
| tgctgtcggc aaatcaatag tgaactgact gaatgccaca tccgcggtat cgccgtcacc | 240 |
| accttggtg tggatggcgc tctggtagat aagcaaggca atctgctcta tccgattatt | 300 |
| agctggaaat gtccgcgaac agcagcggtt atggacaata ttgaacggtt aatctccgca | 360 |
| cagcggttgc aggctatttc tggcgtcgga gcctttagtt tcaatacgtt atataagttg | 420 |
| gtgtggttga agaaaaatca tccacaactg ctggaacgcg cgcacgcctg gctctttatt | 480 |
| tcgtcgctga ttaaccaccg tttaaccggc gaattcacta ctgatatcac gatggccgga | 540 |
| accagccaga tgctggatat ccagcaacgc gatttcagtc gcaaattttt acaagccacc | 600 |
| ggtattccac gccgactctt ccctcgtctg gtggaagcgg gtgaacagat tggtacgcta | 660 |
| cagaacagcg ccgcagcaat gctcggctta cccgttggca taccggtgat ttccgcaggt | 720 |
| cacgataccc agttcgccct ttttggcgct ggtgctgaac aaaatgaacc cgtgctctct | 780 |
| tccggtacat gggaaatttt aatggttcgc agcgcccagg ttgatacttc gctgttaagt | 840 |
| cagtacgccg gttccaccct cgaactggat agccaggcag ggttgtataa cccaggtatg | 900 |
| caatggctgg catccggcgt gctggaatgg gtgagaaaac tgttctggac ggctgaaaca | 960 |
| ccctggcaaa tgttgattga agaagctcgt ctgatcgcgc ctggcgcgga tggcgtaaaa | 1020 |
| atgcagtgtg atttattgtc gtgtcagaac gctggctggc aaggagtgac gcttaatacc | 1080 |
| acgcgggggc atttctatcg cgcggcgctg gaagggttaa ctgcgcaatt acagcgcaat | 1140 |
| ctacagatgc tggaaaaaat cgggcacttt aaggcctctg aattattgtt agtcggtgga | 1200 |

```
ggaagtcgca acacattgtg gaatcagatt aaagccaata tgcttgatat tccggtaaaa    1260
gttctcgacg acgccgaaac gaccgtcgca ggagctgcgc tgttcggttg gtatggcgta    1320
ggggaattta acagcccgga agaagcccgc gcacagattc attatcagta ccgttatttc    1380
tacccgcaaa ctgaacctga atttatagag gaagtgtga                           1419

<210> SEQ ID NO 6
<211> LENGTH: 1470
<212> TYPE: DNA
<213> ORGANISM: Escherichia coli

<400> SEQUENCE: 6
atgacctttc gcaattgtgt cgccgtcgat ctcggcgcat ccagtgggcg cgtgatgctg      60
gcgcgttacg agcgtgaatg ccgcagcctg acgctgcgcg aaatccatcg ttttaacaat     120
gggctgcata gtcagaacgg ctatgtcacc tgggatgtgg atagccttga aagtgccatt     180
cgccttggat taaacaaggt gtgcgaggaa gggattcgta tcgatagcat tgggattgat     240
acctggggcg tggactttgt gctgctcgac caacagggtc agcgtgtggg cctgcccgtt     300
gcttatcgcg atagccgcac caatggccta atggcgcagg cacaacaaca actcggcaaa     360
cgcgatattt atcaacgtag cggcatccag tttctgccct tcaatacgct ttatcagttg     420
cgtgcgctga cggagcaaca acctgaactt attccacaca ttgctcacgc tctgctgatg     480
ccggattact tcagttatcg cctgaccggc aagatgaact gggaatatac caacgccacg     540
accacgcaac tggtcaatat caatagcgac gactgggacg agtcgctact ggcgtggagc     600
ggggccaaca aagcctggtt tggtcgcccg acgcatccgg gtaatgtcat aggtcactgg     660
atttgcccgc agggtaatga gattccagtg gtcgccgttg ccagccatga taccgccagc     720
gcggttatcg cctcgccgtt aaacggctca cgtgctgctt atctctcttc tggcacctgg     780
tcattgatgg gcttcgaaag ccagacgcca tttaccaatg cacggcact ggcagccaac     840 atcaccaatg aaggcggggc ggaaggtcgc tatcgggtgc tgaaaaatat tatgggctta     900
tggctgcttc agcgagtgct tcaggagcag caaatcaacg atcttccggc gcttatctcc     960
gcgacacagg cacttccggc ttgccgcttc attatcaatc ccaatgacga tcgctttatt    1020
aatcctgaga cgatgtgcag cgaaattcag gctgcgtgtc gggaaacggc gcaaccgatc    1080
ccggaaagtg atgctgaact ggcgcgctgc attttcgaca gtctggcgct gctgtatgcc    1140
gatgtgttgc atgagctggc gcagctgcgc ggtgaagatt tctcgcaact gcatattgtc    1200
ggcggaggct gccagaacac gctgctcaac cagctatgcg ccgatgcctg cggtattcgg    1260
gtgatcgccg ggcctgttga agcctcgacg ctcggcaata tcggcatcca gttaatgacg    1320
ctggatgaac tcaacaatgt ggatgatttc cgtcaggtcg tcagcaccac cgcgaatctg    1380
accaccttta cccctaatcc tgacagtgaa attgccccact atgtggcgca gattcactct    1440
acacgacaga caaaggagct ttgcgcatga                                      1470

<210> SEQ ID NO 7
<211> LENGTH: 1500
<212> TYPE: DNA
<213> ORGANISM: Escherichia coli

<400> SEQUENCE: 7
atgagcatct tgtacgaaga gcgtcttgat ggcgctttac ccgatgtcga ccgcacatcg      60
gtactgatgg cactgcgtga gcatgtccct ggacttgaga tcctgcatac cgatgaggag     120
```

-continued

```
atcattcctt acgagtgtga cgggttgagc gcgtatcgca cgcgtccatt actggttgtt      180
ctgcctaagc aaatggaaca ggtgacagcg attctggctg tctgccatcg cctgcgtgta      240
ccggtggtga cccgtggtgc aggcaccggg ctttctggtg gcgcgctgcc gctggaaaaa      300
ggtgtgttgt tggtgatggc gcgctttaaa gagatcctcg acattaaccc cgttggtcgc      360
cgcgcgcgcg tgcagccagg cgtgcgtaac ctggcgatct cccaggccgt tgcaccgcat      420
aatctctact acgcaccgga cccttcctca caaatcgcct gttccattgg cggcaatgtg      480
gctgaaaatg ccggcggcgt ccactgcctg aaatatggtc tgaccgtaca taacctgctg      540
aaaattgaag tgcaaacgct ggacggcgag gcactgacgc ttggatcgga cgcgctggat      600
tcacctggtt ttgacctgct ggcgctgttc accggatcgg aaggtatgct cggcgtgacc      660
accgaagtga cggtaaaact gctgccgaag ccgcccgtgg cgcgggttct gttagccagc      720
tttgactcgg tagaaaaagc cggacttgcg gttggtgaca tcatcgccaa tggcattatc      780
cccggcgggc tggagatgat ggataacctg tcgatccgcg cggcggaaga ttttattcat      840
gccggttatc ccgtcgacgc cgaagcgatt ttgttatgcg agctggacgg cgtggagtct      900
gacgtacagg aagactgcga gcgggttaac gacatcttgt tgaaagcggg cgcgactgac      960
gtccgtctgg cacaggacga agcagagcgc gtacgtttct gggccggtcg caaaaatgcg     1020
ttcccggcgg taggacgtat ctccccggat tactactgca tggatggcac catcccgcgt     1080
cgcgccctgc ctggcgtact ggaaggcatt gcccgtttat cgcagcaata tgatttacgt     1140
gttgccaacg tctttcatgc cggagatggc aacatgcacc cgttaatcct tttcgatgcc     1200
aacgaacccg tgaatttgc ccgcgcgaaa gagctgggcg gaagatcct cgaactctgc      1260 gttgaagttg gcggcagcat cagtggcgaa catggcatcg gcgagaaaaa aatcaatcaa     1320
atgtgcgccc agttcaacag cgatgaaatc acgaccttcc atgcggtcaa ggcggcgttt     1380
gaccccgatg gtttgctgaa ccctgggaaa acattcccca cgctacaccg ctgtgctgaa     1440
tttggtgcca tgcatgtgca tcacggtcat ttacctttcc ctgaactgga gcgtttctga     1500
```

<210> SEQ ID NO 8
<211> LENGTH: 861
<212> TYPE: DNA
<213> ORGANISM: Escherichia coli

<400> SEQUENCE: 8

```
atgagcatta tctccactaa atatctgtta caggacgccc aggccaatgg ctacgcggtg       60
cctgctttta acattcataa cgccgagacg atccaagcga tcctcgaagt gtgcagtgaa      120
atgcgatcgc cggtgatcct cgccggaacg ccggggacct taaacacat cgcgctggaa      180 gagatctacg ccctgtgtag cgcctattcc acaacctaca acatgccact ggcgctgcat      240
ctcgaccacc acgaatcgct ggatgatatt cgccgtaaag tccacgcagg tgtgcgcagt      300
gcgatgatcg acggcagcca cttcccgttt gccgagaacg tgaagctggt gaaatcggtt      360
gttgacttct gccactcaca agattgcagc gtggaagcag aactgggccg cctgggcggt      420
gttgaagatg acatgagcgt tgacgccgaa agtgcattcc tgaccgatcc acaagaagct      480
aaacgctttg tcgaactgac tggcgtcgac agcctggcgg tagcgattgg tacggcgcac      540
ggcttataca gcaaaacgcc gaagattgat ttccagcggc tggcggaaat tcgtgaagtg      600
gtggatgttc ctctggtgct gcatggtgcc agcgatgttc cggatgaatt tgtccgtcgc      660
actattgaac ttggcgtcac aaaagtgaac gttgccacag aattaaaaat agccttcgct      720
ggcgcggtta agcctggtt tgcggaaaat ccgcagggta atgatcctcg ttattatatg      780
```

```
cgcgtcggaa tggatgcgat gaaagaagtt gtcagaaata aaattaatgt ctgtggttca    840
gcgaatcgaa tttcagcata a                                              861
```

<210> SEQ ID NO 9
<211> LENGTH: 1053
<212> TYPE: DNA
<213> ORGANISM: Escherichia coli

<400> SEQUENCE: 9

```
atgacagata ttgcgcagtt gcttggcaaa gacgccgaca acctttttaca gcaccgttgt    60 atgacaattc cttctgacca gctttatctc cccggacatg actacgtaga ccgcgtaatg   120
attgacaata atcgcccgcc agcggtgtta cgtaatatgc agacgttgta caacaccggg   180
cgtctggctg gcacaggata tctttctatt ctgccggttg accagggcgt tgagcactct   240
gccggagctt catttgctgc taacccgctc tactttgacc cgaaaaacat tgttgaactg   300
gcgatcgaag cgggctgtaa ctgtgtggcg tcaacttacg gcgtgctggc gtcggtatcg   360
cggcgttatg cgcatcgcat tccattcctc gtcaaactta atcacaacga gacgctaagt   420
tacccgaata cctacgatca aacgctgtat gccagcgtgg agcaggcgtt caacatgggc   480
gcggttgcgg ttggtgcgac tatctatttt ggctcggaag agtcacgtcg ccagattgaa   540
gaaatttctg cggcttttga acgtgcgcac gagctgggta tggtgacagt gctgtgggcc   600
tatttgcgta actccgcctt taagaaagat ggcgttgatt accatgtttc cgccgacctg   660
accggtcagg caaaccatct ggcggcaacc atcggtgcag atatcgtcaa acaaaaaatg   720
gcggaaaata acggcggcta taaagcaatt aattacggtt acaccgacga tcgtgtttac   780
agcaaattga ccagcgaaaa cccgattgat ctggtgcgtt atcagttagc taactgctat   840
atgggtcggg ctgggttgat aaactccggc ggtgctgcgg gcggtgaaac tgacctcagc   900
gatgcagtgc gtactgcggt tatcaacaaa cgcgcaggcg aatggggct gattcttgga   960 cgtaaagcgt tcaagaaatc gatggctgac ggcgtgaaac tgattaacgc cgtgcaggac  1020
gtttatctcg atagcaaaat tactatcgcc tga                                1053
```

<210> SEQ ID NO 10
<211> LENGTH: 939
<212> TYPE: DNA
<213> ORGANISM: Escherichia coli

<400> SEQUENCE: 10

```
atggatatca tcttttatca cccaacgttc gatacccaat ggtggattga ggcactgcgc    60
aaagctattc ctcaggcaag agtcagagca tggaaaagcg gagataatga ctctgctgat   120
tatgctttag tctggcatcc tcctgttgaa atgctggcag gcgcgatct aaagcggtg    180 ttcgcactcg gggccggtgt tgattctatt ttgagcaagc tacaggcaca ccctgaaatg   240 ctgaacccttt ctgttccact ttttcgcctg gaagataccg gtatgggcga gcaaatgcag   300
gaatatgctg tcagtcaggt gctgcattgg tttcgacgtt ttgacgatta tcgcatccag   360
caaaatagtt cgcattggca accgctgcct gaatatcatc gggaagattt taccatcggc   420
attttgggcg caggcgtact gggcagtaaa gttgctcaga gtctgcaaac ctggcgcttt   480
ccgctgcgtt gctggagtcg aacccgtaaa tcgtggcctg gcgtgcaaag ctttgccgga   540
cgggaagaac tgtctgcatt tctgagccaa tgtcgggtat tgattaattt gttaccgaat   600 accctgaaa ccgtcggcat tattaatcaa caattactcg aaaaattacc ggatggcgcg   660
```

```
tatctcctca acctggcgcg tggtgttcat gttgtggaag atgacctgct cgcggcgctg      720
gatagcggca aagttaaagg cgcaatgttg gatgttttta atcgtgaacc cttaccgcct      780
gaaagtccgc tctggcaaca tccacgcgtg acgataacac cacatgtcgc cgcgattacc      840
cgtcccgctg aagctgtgga gtacatttct cgcaccattg cccagctcga aaaaggggag      900
agggtctgcg ggcaagtcga ccgcgcacgc ggctactaa                             939
```

<210> SEQ ID NO 11
<211> LENGTH: 1305
<212> TYPE: DNA
<213> ORGANISM: Escherichia coli

<400> SEQUENCE: 11

```
atgaaaaccc gtacacaaca aattgaagaa ttacagaaag agtggactca accgcgttgg       60
gaaggcatta ctcgcccata cagtgcggaa gatgtggtga aattacgcgg ttcagtcaat      120
cctgaatgca cgctggcgca actgggcgca gcgaaaatgt ggcgtctgct gcacggtgag      180
tcgaaaaaag gctacatcaa cagcctcggc gcactgactg gcggtcaggc gctgcaacag      240
gcgaaagcgg gtattgaagc agtctatctg tcgggatggc aggtagcggc ggacgctaac      300
ctggcggcca gcatgtatcc ggatcagtcg ctctatccgg caaactcggt gccagctgtg      360
gtggagcgga tcaacaacac cttccgtcgt gccgatcaga tccaatggtc cgcgggcatt      420
gagccgggcg atccgcgcta tgtcgattac ttcctgccga tcgttgccga tgcggaagcc      480
ggttttggcg gtgtcctgaa tgcctttgaa ctgatgaaag cgatgattga agccggtgca      540
gcggcagttc acttcgaaga tcagctggcg tcagtgaaga atgcggtca catgggcggc      600 aaagttttag tgccaactca ggaagctatt cagaaactgg tcgcggcgcg tctggcagct      660
gacgtgacgg cgttccaac cctgctggtt gcccgtaccg atgctgatgc ggcggatctg      720
atcacctccg attgcgaccc gtatgacagc gaatttatta ccggcgagcg taccagtgaa      780
ggcttcttcc gtactcatgc gggcattgag caagcgatca gccgtggcct ggcgtatgcg      840
ccatatgctg acctggtctg tgtgaaaacc tccacgccgg atctggaact ggcgcgtcgc      900
tttgcacaag ctatccacgc gaaatatccg ggcaaactgc tggcttataa ctgctcgccg      960
tcgttcaact ggcagaaaaa cctcgacgac aaaactattg ccagcttcca gcagcagctg     1020
tcggatatgg gctacaagtt ccagttcatc accctggcag gtatccacag catgtggttc     1080
aacatgtttg acctggcaaa cgcctatgcc cagggcgagg gtatgaagca ctacgttgag     1140
aaagtgcagc agccggaatt tgccgccgcg aaagatggct ataccttcgt atctcaccag     1200
caggaagtgg gtacaggtta cttcgataaa gtgacgacta ttattcaggg cggcacgtct     1260
tcagtcaccg cgctgaccgg ctccactgaa gaatcgcagt tctaa                     1305
```

<210> SEQ ID NO 12
<211> LENGTH: 323
<212> TYPE: DNA
<213> ORGANISM: Saccharomyces cerevisiae

<400> SEQUENCE: 12

```
tgcagatcaa aggcaaagac agaaaccgta gtaaaggttg acttttcaca acagtgtctc       60 catttttat attgtattat taaagctatt tagttatttg gatactgttt tttttccaga      120
agttttcttt ttagtaaagt acaatccagt aaaaatgaag gatgaacaat cggtgtatgc      180
agattcaaca ccaataaatg caatgtttat ttctttggaa cgtttgtgtt gttcgaaatc      240
caggataatc cttcaacaag accctgtccg gataaggcgt tactaccgat gacacaccaa      300
```

```
gaaccacaca tctatttcct tat                                              323
```

<210> SEQ ID NO 13
<211> LENGTH: 311
<212> TYPE: DNA
<213> ORGANISM: Saccharomyces cerevisiae

<400> SEQUENCE: 13

```
tattctgatc gtagatcatc agatttgata tgatattatt tgtgaaaaaa tgaaataaaa       60
ctttatacaa cttaaataca actttttta taaacgatta agcaaaaaaa tagtttcaaa       120
cttttaacaa tattccaaac actcagtcct tttccttctt atattatagg tgtacgtatt      180
atagaaaaat ttcaatgatt actttttct tcttttcct tgtaccagca catggccgag        240
cttgaatgtt aaacccttcg agagaatcac accattcaag tataaagcca ataagaata      300 taaaaaatta t                                                           311
```

<210> SEQ ID NO 14
<211> LENGTH: 514
<212> TYPE: DNA
<213> ORGANISM: Saccharomyces cerevisiae

<400> SEQUENCE: 14

```
atgggtcatt acgtaaataa tgataggaat gggattcttc tatttttcct ttttccattc       60
tagcagccgt cgggaaaacg tggcatcctc tctttcgggc tcaattggag tcacgctgcc      120
gtgagcatcc tctcttttcca tatctaacaa ctgagcacgt aaccaatgga aaagcatgag    180
cttagcgttg ctccaaaaaa gtattggatg gttaatacca tttgtctgtt ctcttctgac     240
tttgactcct caaaaaaaaa aaatctacaa tcaacagatc gcttcaatta cgccctcaca    300 aaaactttt tccttcttct tcgcccacgt taaatttat ccctcatgtt gtctaacgga      360
tttctgcact tgatttatta taaaaagaca aagacataat acttctctat caatttcagt     420
tattgttctt ccttgcgtta ttcttctgtt cttcttttc ttttgtcata taaccata       480 accaagtaat acatattcaa aagaaacat aaat                                  514
```

<210> SEQ ID NO 15
<211> LENGTH: 391
<212> TYPE: DNA
<213> ORGANISM: Saccharomyces cerevisiae

<400> SEQUENCE: 15

```
tatttaaact gtgaggacct taatacattc agacacttct gcggtatcac cctacttatt       60
cccttcgaga ttatatctag gaacccatca ggttggtgga agattacccg ttctaagact      120
tttcagcttc ctctattgat gttacacctg gacaccctt ttctggcatc cagtttttaa      180
tcttcagtgg catgtgagat tctccgaaat taattaaagc aatcacacaa ttctctcgga     240
taccacctcg gttgaaactg acaggtggtt tgttacgcat gctaatgcaa aggagcctat    300 ataccttgg ctcggctgct gtaacaggga atataaaggg cagcataatt taggagttta    360
gtgaacttgc aacatttact attttcccctt c                                   391
```

<210> SEQ ID NO 16
<211> LENGTH: 23
<212> TYPE: DNA
<213> ORGANISM: Artificial Sequence
<220> FEATURE:
<223> OTHER INFORMATION: Primer YC-49 rhaB fw-ndeI

<400> SEQUENCE: 16
catatgacct tcgcaattg tgt                                     23

<210> SEQ ID NO 17
<211> LENGTH: 26
<212> TYPE: DNA
<213> ORGANISM: Artificial Sequence
<220> FEATURE:
<223> OTHER INFORMATION: Primer YC-50 rhaB rev-BamHI

<400> SEQUENCE: 17
ggatcctcat gcgcaaagct cctttg                                 26

<210> SEQ ID NO 18
<211> LENGTH: 52
<212> TYPE: DNA
<213> ORGANISM: Artificial Sequence
<220> FEATURE:
<223> OTHER INFORMATION: Primer FucokinasefwNcoI

<400> SEQUENCE: 18
ccatggatgc accatcacca tcaccatatg ttatccggct atattgcagg ag     52

<210> SEQ ID NO 19
<211> LENGTH: 38
<212> TYPE: DNA
<213> ORGANISM: Artificial Sequence
<220> FEATURE:
<223> OTHER INFORMATION: Primer FucokinaserevBamHISalI

<400> SEQUENCE: 19
ggatccgtcg acattaacgg cgaaattgtt tcagcatt                    38

<210> SEQ ID NO 20
<211> LENGTH: 40
<212> TYPE: DNA
<213> ORGANISM: Artificial Sequence
<220> FEATURE:
<223> OTHER INFORMATION: Primer AldoB_BamHI_Fw

<400> SEQUENCE: 20
ttggatccag gaggattcat atggcacatc gctttccggc                  40

<210> SEQ ID NO 21
<211> LENGTH: 28
<212> TYPE: DNA
<213> ORGANISM: Artificial Sequence
<220> FEATURE:
<223> OTHER INFORMATION: Primer AldoB_Hind3_Rv

<400> SEQUENCE: 21
ttaagctttt aatacgtgta acaggccg                               28

<210> SEQ ID NO 22
<211> LENGTH: 29
<212> TYPE: DNA
<213> ORGANISM: Artificial Sequence
<220> FEATURE:
<223> OTHER INFORMATION: Primer fbaB-NdeI-fw

<400> SEQUENCE: 22
catatgacag atattgcgca gttgcttgg                              29

<210> SEQ ID NO 23
<211> LENGTH: 29

-continued

<212> TYPE: DNA
<213> ORGANISM: Artificial Sequence
<220> FEATURE:
<223> OTHER INFORMATION: Primer fbaB-BamHI-rev

<400> SEQUENCE: 23
ggatcctcag gcgatagtaa ttttgctat                                   29

<210> SEQ ID NO 24
<211> LENGTH: 29
<212> TYPE: DNA
<213> ORGANISM: Artificial Sequence
<220> FEATURE:
<223> OTHER INFORMATION: Primer agaY-NdeI-fw

<400> SEQUENCE: 24
catatgagca ttatctccac taaatatct                                   29

<210> SEQ ID NO 25
<211> LENGTH: 29
<212> TYPE: DNA
<213> ORGANISM: Artificial Sequence
<220> FEATURE:
<223> OTHER INFORMATION: Primer agaY-BamHI-rev

<400> SEQUENCE: 25
ggatccttat gctgaaattc gattcgctg                                   29

<210> SEQ ID NO 26
<211> LENGTH: 56
<212> TYPE: DNA
<213> ORGANISM: Artificial Sequence
<220> FEATURE:
<223> OTHER INFORMATION: Primer YC73-Fw YqhD

<400> SEQUENCE: 26
cctctagagt cgacctgcag aggaggattc atatgaacaa ctttaatctg cacacc     56

<210> SEQ ID NO 27
<211> LENGTH: 34
<212> TYPE: DNA
<213> ORGANISM: Artificial Sequence
<220> FEATURE:
<223> OTHER INFORMATION: Primer YC74-Rev YqhD

<400> SEQUENCE: 27
gccaaaacag aagcttttag cgggcggctt cgta                             34

<210> SEQ ID NO 28
<211> LENGTH: 42
<212> TYPE: DNA
<213> ORGANISM: Artificial Sequence
<220> FEATURE:
<223> OTHER INFORMATION: Primer YC52-fwkhkfu

<400> SEQUENCE: 28
cggtacccgg ggatcaggag gcacacgatg aagaagcag at                     42

<210> SEQ ID NO 29
<211> LENGTH: 25
<212> TYPE: DNA
<213> ORGANISM: Artificial Sequence
<220> FEATURE:
<223> OTHER INFORMATION: Primer YC53-revkhkfu

<400> SEQUENCE: 29

```
tcacacgatg ccatcaaagc cctgc                                          25
```

<210> SEQ ID NO 30
<211> LENGTH: 54
<212> TYPE: DNA
<213> ORGANISM: Artificial Sequence
<220> FEATURE:
<223> OTHER INFORMATION: Primer YC-76 fw AldoB

<400> SEQUENCE: 30

```
cctctagagt cgacctgcag aggaggattc atatggcaca tcgctttccg gctc          54
```

<210> SEQ ID NO 31
<211> LENGTH: 36
<212> TYPE: DNA
<213> ORGANISM: Artificial Sequence
<220> FEATURE:
<223> OTHER INFORMATION: Primer YC-75 fw AldoB

<400> SEQUENCE: 31

```
gccaaaacag aagcttttaa tacgtgtaac aggccg                              36
```

<210> SEQ ID NO 32
<211> LENGTH: 44
<212> TYPE: DNA
<213> ORGANISM: Artificial Sequence
<220> FEATURE:
<223> OTHER INFORMATION: Primer aldA_KpnI_Fw

<400> SEQUENCE: 32

```
ttggtaccaa gaaggagaat tcatatgtca gtacccgttc aaca                     44
```

<210> SEQ ID NO 33
<211> LENGTH: 28
<212> TYPE: DNA
<213> ORGANISM: Artificial Sequence
<220> FEATURE:
<223> OTHER INFORMATION: Primer aldA_Hind3_Rv

<400> SEQUENCE: 33

```
ttaagctttt aagactgtaa ataaacca                                       28
```

<210> SEQ ID NO 34
<211> LENGTH: 55
<212> TYPE: DNA
<213> ORGANISM: Artificial Sequence
<220> FEATURE:
<223> OTHER INFORMATION: Primer pACT ycdW-Fw

<400> SEQUENCE: 34

```
gagctcggta cccggggatc caggaggcac acgatggata tcatctttta tcacc         55
```

<210> SEQ ID NO 35
<211> LENGTH: 49
<212> TYPE: DNA
<213> ORGANISM: Artificial Sequence
<220> FEATURE:
<223> OTHER INFORMATION: Primer pACT ycdW-Rev

<400> SEQUENCE: 35

```
ctcatccgcc aaaacagaag cttttagtag ccgcgtgcgc ggtcgactt                49
```

<210> SEQ ID NO 36
<211> LENGTH: 52
<212> TYPE: DNA
<213> ORGANISM: Artificial Sequence
<220> FEATURE:
<223> OTHER INFORMATION: Primer Operon aceA-Fw

<400> SEQUENCE: 36
gcacgcggct actaaaggag gaaccgtatg aaaacccgta cacaacaaat tg    52

<210> SEQ ID NO 37
<211> LENGTH: 47
<212> TYPE: DNA
<213> ORGANISM: Artificial Sequence
<220> FEATURE:
<223> OTHER INFORMATION: Primer pACT aceA-Rev

<400> SEQUENCE: 37
ctcatccgcc aaaacagaag cttttagaac tgcgattctt cagtgga    47

<210> SEQ ID NO 38
<211> LENGTH: 42
<212> TYPE: DNA
<213> ORGANISM: Artificial Sequence
<220> FEATURE:
<223> OTHER INFORMATION: Primer Operon ycdW-Rev

<400> SEQUENCE: 38
tcatacggtt cctcctttag tagccgcgtg cgcggtcgac tt    42

<210> SEQ ID NO 39
<211> LENGTH: 65
<212> TYPE: DNA
<213> ORGANISM: Artificial Sequence
<220> FEATURE:
<223> OTHER INFORMATION: Primer YC1_pTPI fw

<400> SEQUENCE: 39
ggaacaaaag ctggagctcg taggaacaat ttcgggcctt aaactgtgag gaccttaata    60
cattc    65

<210> SEQ ID NO 40
<211> LENGTH: 42
<212> TYPE: DNA
<213> ORGANISM: Artificial Sequence
<220> FEATURE:
<223> OTHER INFORMATION: Primer YC2_pTPI Rev

<400> SEQUENCE: 40
atctgcttct cttccatttt tagtttatgt atgtgttttt tg    42

<210> SEQ ID NO 41
<211> LENGTH: 44
<212> TYPE: DNA
<213> ORGANISM: Artificial Sequence
<220> FEATURE:
<223> OTHER INFORMATION: Primer YC3_khk-C fw

<400> SEQUENCE: 41
cacatacata aactaaaaat ggaagagaag cagatcctgt gcgt    44

<210> SEQ ID NO 42
<211> LENGTH: 42
<212> TYPE: DNA
<213> ORGANISM: Artificial Sequence
<220> FEATURE:
<223> OTHER INFORMATION: Primer YC4_khk-C rev

<400> SEQUENCE: 42

```
tgtctttgcc tttgatctgc tcacacgatg ccatcaaagc cc                  42
```

<210> SEQ ID NO 43
<211> LENGTH: 45
<212> TYPE: DNA
<213> ORGANISM: Artificial Sequence
<220> FEATURE:
<223> OTHER INFORMATION: Primer YC5_ter trki fw

<400> SEQUENCE: 43

```
gatggcatcg tgtgagcaga tcaaaggcaa agacagaaac cgtag              45
```

<210> SEQ ID NO 44
<211> LENGTH: 56
<212> TYPE: DNA
<213> ORGANISM: Artificial Sequence
<220> FEATURE:
<223> OTHER INFORMATION: Primer YC6_ter trki rev

<400> SEQUENCE: 44

```
attcctatca ttatttacgt aatgacccat cttggtgtgt catcggtagt aacgcc  56
```

<210> SEQ ID NO 45
<211> LENGTH: 49
<212> TYPE: DNA
<213> ORGANISM: Artificial Sequence
<220> FEATURE:
<223> OTHER INFORMATION: Primer YC7_pFBA1 fw

<400> SEQUENCE: 45

```
ccgatgacac accaagatgg gtcattacgt aaataatgat aggaatggg          49
```

<210> SEQ ID NO 46
<211> LENGTH: 55
<212> TYPE: DNA
<213> ORGANISM: Artificial Sequence
<220> FEATURE:
<223> OTHER INFORMATION: Primer YC8_pFBA1 rev

<400> SEQUENCE: 46

```
tgcgtcagag ccggaaagcg atgtgccatt ttgaatatgt attacttggt tatgg   55
```

<210> SEQ ID NO 47
<211> LENGTH: 44
<212> TYPE: DNA
<213> ORGANISM: Artificial Sequence
<220> FEATURE:
<223> OTHER INFORMATION: Primer YC9_aldoB fw

<400> SEQUENCE: 47

```
ccaagtaata catattcaaa atggcacatc gctttccggc tctg               44
```

<210> SEQ ID NO 48
<211> LENGTH: 46
<212> TYPE: DNA
<213> ORGANISM: Artificial Sequence
<220> FEATURE:
<223> OTHER INFORMATION: Primer YC10_aldoB fw

<400> SEQUENCE: 48

```
ctgatgatct acgatcagaa tttaatacgt gtaacaggcc gtaaac             46
```

<210> SEQ ID NO 49
<211> LENGTH: 45
<212> TYPE: DNA
<213> ORGANISM: Artificial Sequence

```
<220> FEATURE:
<223> OTHER INFORMATION: Primer YC11_Tlk1 terminator fw

<400> SEQUENCE: 49
gttacacgta ttaaattctg atcgtagatc atcagatttg atatg            45

<210> SEQ ID NO 50
<211> LENGTH: 60
<212> TYPE: DNA
<213> ORGANISM: Artificial Sequence
<220> FEATURE:
<223> OTHER INFORMATION: Primer YC12_Tlk1 terminator rev

<400> SEQUENCE: 50
cgcgcgtaat acgactcact atagggcgaa ttggatattc tttattggct ttatacttga   60

<210> SEQ ID NO 51
<211> LENGTH: 1104
<212> TYPE: DNA
<213> ORGANISM: Escherichia coli

<400> SEQUENCE: 51
atggaccgca ttattcaatc accgggtaaa tacatccagg gcgctgatgt gattaatcgt    60
ctgggcgaat acctgaagcc gctggcagaa cgctggttag tggtgggtga caaatttgtt   120
ttaggttttg ctcaatccac tgtcgagaaa agctttaaag atgctggact ggtagtagaa   180
attgcgccgt ttggcggtga atgttcgcaa aatgagatcg accgtctgcg tggcatcgcg   240
gagactgcgc agtgtggcgc aattctcggt atcggtggcg gaaaaaccct cgatactgcc   300
aaagcactgg cacatttcat gggtgttccg gtagcgatcc caccgactat cgcctctacc   360
gatgcaccgt gcagcgcatt gtctgttatc tacaccgatg agggtgagtt tgaccgctat   420
ctgctgttgc aaataaaccc gaatatggtc attgtcgaca ccaaaatcgt cgctggcgca   480
cctgcacgtc tgttagcggc gggtatcggc gatgcgctgg caacctggtt tgaagcgcgt   540
gcctgctctc gtagcggcgc gaccaccatg gcgggcggca agtgcaccca ggctgcgctg   600
gcactggctg aactgtgcta acacccctct ctggaagaag cgaaaaagc gatgcttgct   660 gccgaacagc atgtagtgac tccggcgctg gagcgcgtga ttgaagcgaa cacctatttg   720
agcggtgttg gttttgaaag tggtggtctg gctgcggcgc acgcagtgca taacggcctg   780
accgctatcc cggacgcgca tcactattat cacggtgaaa aagtggcatt cggtacgctg   840
acgcagctgg ttctggaaaa tgcgccggtg gaggaaatcg aaaccgtagc tgcccttagc   900
catgcggtag gtttgccaat aactctcgct caactggata ttaaagaaga tgtcccggcg   960
aaaatgcgaa ttgtggcaga agcggcatgt gcagaaggtg aaaccattca caacatgcct  1020
ggcggcgcga cgccagatca ggtttacgcc gctctgctgg tagccgacca gtacggtcag  1080
cgtttcctgc aagagtggga ataa                                         1104

<210> SEQ ID NO 52
<211> LENGTH: 1149
<212> TYPE: DNA
<213> ORGANISM: Escherichia coli

<400> SEQUENCE: 52
atggctaaca gaatgattct gaacgaaacg gcatggtttg tcggggtgc tgttggggct     60 ttaaccgatg aggtgaaacg ccgtggttat cagaaggcgc tgatcgtcac cgataaaacg    120
ctggtgcaat gcggcgtggt ggcgaaagtg accgataaga tggatgctgc agggctggca    180
```

```
tgggcgattt acgacggcgt agtgcccaac ccaacaatta ctgtcgtcaa agaagggctc      240
ggtgtattcc agaatagcgg cgcggattac ctgatcgcta ttggtggtgg ttctccacag      300
gatacttgta aagcgattgg cattatcagc aacaacccgg agtttgccga tgtgcgtagc      360
ctggaagggc tttccccgac caataaaccc agtgtaccga ttctggcaat tcctaccaca      420
gcaggtactg cggcagaagt gaccattaac tacgtgatca ctgacgaaga gaaacggcgc      480
aagtttgttt gcgttgatcc gcatgatatc ccgcaggtgg cgtttattga cgctgacatg      540
atggatggta tgcctccagc gctgaaagct gcgacgggtg tcgatgcgct cactcatgct      600
attgaggggt atattacccg tggcgcgtgg gcgctaaccg atgcactgca cattaaagcg      660
attgaaatca ttgctggggc gctgcgagga tcggttgctg gtgataagga tgccggagaa      720
gaaatggcgc tcgggcagta tgttgcgggt atgggcttct cgaatgttgg gttagggttg      780
gtgcatggta tggcgcatcc actgggcgcg ttttataaca ctccacacgg tgttgcgaac      840
gccatcctgt taccgcatgt catgcgttat aacgctgact ttaccggtga aagtaccgc       900 gatatcgcgc gcgttatggg cgtgaaagtg aaggtatga gcctggaaga ggcgcgtaat      960
gccgctgttg aagcggtgtt tgctctcaac cgtgatgtcg gtattccgcc acatttgcgt     1020
gatgttggtg tacgcaagga agacattccg gcactggcgc aggcggcact ggatgatgtt     1080
tgtaccggtg gcaacccgcg tgaagcaacg cttgaggata ttgtagagct ttaccatacc     1140
gcctggtaa                                                             1149

<210> SEQ ID NO 53
<211> LENGTH: 1455
<212> TYPE: DNA
<213> ORGANISM: Escherichia coli

<400> SEQUENCE: 53
atgtatatcg ggatagatct tggcacctcg ggcgtaaaag ttattttgct caacgagcag       60
ggtgaggtgt tgctgcgca aacggaaaag ctgaccgttt cgcgcccgca tccactctgg      120
tcggaacaag acccggaaca gtggtggcag gcaactgatc gcgcaatgaa agctctgggc      180
gatcagcatt ctctgcagga cgttaaagca ttgggtattg ccggccagat gcacggagca      240
accttgctgg atgctcagca acgggtgtta cgccctgcca ttttgtggaa cgacgggcgc      300
tgtgcgcaag agtgcacttt gctggaagcg cgagttccgc aatcgcgggt gattaccggc      360
aacctgatga tgcccggatt tactgcgcct aaattgctat gggttcagcg gcatgagccg      420
gagatattcc gtcaaatcga caaagtatta ttaccgaaag attacttgcg tctgcgtatg      480 acggggagt tgccagcga tatgtctgac gcagctggca ccatgtggct ggatgtcgca      540
aagcgtgact ggagtgacgt catgctgcag gcttgcgact tatctcgtga ccagatgccc      600
gcattatacg aaggcagcga aattactggt gctttgttac ctgaagttgc gaaagcgtgg      660
ggtatggcga cggtgccagt tgtcgcaggc ggtggcgaca atgcagctgg tgcagttggt      720
gtgggaatgg ttgatgctaa tcaggcaatg ttatcgctgg ggacgtcggg ggtctatttt      780
gctgtcagcg aagggttctt aagcaagcca gaaagcgccg tacatagctt tgccatgcg       840 ctaccgcaac gttggcattt aatgtctgtg atgctgagtg cagcgtcgtg tctggattgg      900
gccgcgaaat taaccggcct gagcaatgtc ccagctttaa tcgctgcagc tcaacaggct      960
gatgaaagtg ccgagccagt ttggtttctg ccttatcttt ccggcgagcg tacgccacac     1020
aataatcccc aggcgaaggg ggttttcttt ggtttgactc atcaacatgg ccccaatgaa     1080
ctggcgcgag cagtgctgga aggcgtgggt tatgcgctgg cagatggcat ggatgtcgtg     1140
```

```
catgcctgcg gtattaaacc gcaaagtgtt acgttgattg ggggcggggc gcgtagtgag    1200
tactggcgtc agatgctggc ggatatcagc ggtcagcagc tcgattaccg tacgggggg     1260 gatgtggggc cagcactggg cgcagcaagg ctggcgcaga tcgcggcgaa tccagagaaa    1320
tcgctcattg aattgttgcc gcaactaccg ttagaacagt cgcatctacc agatgcgcag    1380
cgttatgccg cttatcagcc acgacgagaa acgttccgtc gcctctatca gcaacttctg    1440
ccattaatgg cgtaa                                                     1455
```

<210> SEQ ID NO 54
<211> LENGTH: 45
<212> TYPE: DNA
<213> ORGANISM: Artificial Sequence
<220> FEATURE:
<223> OTHER INFORMATION: Primer gldA_rbs_f

<400> SEQUENCE: 54

```
cctctagagt cgacctgcag aggaggattc atatggaccg catta                    45
```

<210> SEQ ID NO 55
<211> LENGTH: 35
<212> TYPE: DNA
<213> ORGANISM: artificial sequence
<220> FEATURE:
<223> OTHER INFORMATION: Primer gldA_rbs_r

<400> SEQUENCE: 55

```
gccaaaacag aagcttttat tcccactctt gcagg                               35
```

<210> SEQ ID NO 56
<211> LENGTH: 40
<212> TYPE: DNA
<213> ORGANISM: artificial sequence
<220> FEATURE:
<223> OTHER INFORMATION: Primer fucO_fw_inf

<400> SEQUENCE: 56

```
ttggatccag gaggattcat atggctaaca gaatgattct                          40
```

<210> SEQ ID NO 57
<211> LENGTH: 27
<212> TYPE: DNA
<213> ORGANISM: artificial sequence
<220> FEATURE:
<223> OTHER INFORMATION: Primer fucO_rev_inf

<400> SEQUENCE: 57

```
ttaagctttt accaggcggt atggtaa                                        27
```

<210> SEQ ID NO 58
<211> LENGTH: 52
<212> TYPE: DNA
<213> ORGANISM: artificial sequence
<220> FEATURE:
<223> OTHER INFORMATION: Primer FbaB_oper_BamHI_F

<400> SEQUENCE: 58

```
gatggcatcg tgtgaaggag gaaccgtatg acagatattg cgcagttgct tg            52
```

<210> SEQ ID NO 59
<211> LENGTH: 44
<212> TYPE: DNA
<213> ORGANISM: artificial sequence
<220> FEATURE:

<223> OTHER INFORMATION: Primer-FbaB_oper_SalI_R

<400> SEQUENCE: 59
atgcctgcag gtcgacaatt gtcaggcgat agtaattttg ctat    44

<210> SEQ ID NO 60
<211> LENGTH: 68
<212> TYPE: DNA
<213> ORGANISM: artificial sequence
<220> FEATURE:
<223> OTHER INFORMATION: Primer khkrbsweak fw

<400> SEQUENCE: 60
cggtacccgg ggatcggaaa tactataaac ggttaaataa acaaaccata atggaagaga    60
agcagatc    68

<210> SEQ ID NO 61
<211> LENGTH: 70
<212> TYPE: DNA
<213> ORGANISM: artificial sequence
<220> FEATURE:
<223> OTHER INFORMATION: Primer fbabrbsmax fw

<400> SEQUENCE: 61
gatggcatcg tgtgaacagc ttttaattat acactttaag gaggacagac atgacagata    60
ttgcgcagtt    70

<210> SEQ ID NO 62
<211> LENGTH: 35
<212> TYPE: DNA
<213> ORGANISM: artificial sequence
<220> FEATURE:
<223> OTHER INFORMATION: Primer fbabrbsmax rev

<400> SEQUENCE: 62
atgcctgcag gtcgagcgat agtaattttg ctatc    35

<210> SEQ ID NO 63
<211> LENGTH: 46
<212> TYPE: DNA
<213> ORGANISM: artificial sequence
<220> FEATURE:
<223> OTHER INFORMATION: Primer FbaB inf BamHI F

<400> SEQUENCE: 63
cggtacccgg ggatccagga ggattcatat gacagatatt gcgcag    46

<210> SEQ ID NO 64
<211> LENGTH: 39
<212> TYPE: DNA
<213> ORGANISM: artificial sequence
<220> FEATURE:
<223> OTHER INFORMATION: Primer FbaB inf Hind R

<400> SEQUENCE: 64
tccgccaaaa cagaagcttt caggcgatag taattttgc    39

<210> SEQ ID NO 65
<211> LENGTH: 47
<212> TYPE: DNA
<213> ORGANISM: artificial sequence
<220> FEATURE:
<223> OTHER INFORMATION: Primer pACTaceA-Rev

<400> SEQUENCE: 65
ctcatccgcc aaaacagaag cttttagaac tgcgattctt cagtgga                47

<210> SEQ ID NO 66
<211> LENGTH: 49
<212> TYPE: DNA
<213> ORGANISM: artificial sequence
<220> FEATURE:
<223> OTHER INFORMATION: Primer Op aceA ghrA-Fw

<400> SEQUENCE: 66
gaagaatcgc agttctaaag gaggcacacg atggatatca tcttttatc              49

<210> SEQ ID NO 67
<211> LENGTH: 53
<212> TYPE: DNA
<213> ORGANISM: artificial sequence
<220> FEATURE:
<223> OTHER INFORMATION: Primer pACT3 ghrA_XbaI-Rev

<400> SEQUENCE: 67
catccgccaa aacagaagct ttctagatta gtagccgcgt gcgcggtcga ctt         53

<210> SEQ ID NO 68
<211> LENGTH: 53
<212> TYPE: DNA
<213> ORGANISM: artificial sequence
<220> FEATURE:
<223> OTHER INFORMATION: Primer pACTghrA_XbaI-Rev

<400> SEQUENCE: 68
catccgccaa aacagaagct ttctagatta gtagccgcgt gcgcggtcga ctt         53

<210> SEQ ID NO 69
<211> LENGTH: 102
<212> TYPE: DNA
<213> ORGANISM: artificial sequence
<220> FEATURE:
<223> OTHER INFORMATION: Primer glcDEFGB_fw

<400> SEQUENCE: 69
gcgtcttgat ggcgctttac ccgatgtcga ccgcacatcg gtactgatgg cactgcgtga  60
gcatgtccct ggacttgaga tcgtgtaggc tggagctgct tc                    102

<210> SEQ ID NO 70
<211> LENGTH: 99
<212> TYPE: DNA
<213> ORGANISM: artificial sequence
<220> FEATURE:
<223> OTHER INFORMATION: Primer glcDEFGB_rev

<400> SEQUENCE: 70
cgcgtaaacg ccaggcgtgt aataacggtt cggtatagcc gtttggctgt ttcacgccga  60
ggaagattaa atcgctggcc atatgaatat cctccttag                         99

<210> SEQ ID NO 71
<211> LENGTH: 102
<212> TYPE: DNA
<213> ORGANISM: artificial sequence
<220> FEATURE:
<223> OTHER INFORMATION: Primer edd eda_fw

<400> SEQUENCE: 71
cgcgcgagac tcgctctgct tatctcgccc ggatagaaca agcgaaaact tcgaccgttc  60
atcgttcgca gttggcatgc gggtgtaggc tggagctgct tc                    102

<210> SEQ ID NO 72
<211> LENGTH: 100
<212> TYPE: DNA
<213> ORGANISM: artificial sequence
<220> FEATURE:
<223> OTHER INFORMATION: Primer edd eda_rev

<400> SEQUENCE: 72
gcttagcgcc ttctacagct tcacgcgcca gcttagtaat gcggtcgtaa tcgcccgctt    60
ccagcgcatc tgccggaacc catatgaata tcctccttag                         100

<210> SEQ ID NO 73
<211> LENGTH: 20
<212> TYPE: DNA
<213> ORGANISM: artificial sequence
<220> FEATURE:
<223> OTHER INFORMATION: Primer prom galP* fw

<400> SEQUENCE: 73
cacagctaac accacgtcgt                                               20

<210> SEQ ID NO 74
<211> LENGTH: 82
<212> TYPE: DNA
<213> ORGANISM: artificial sequence
<220> FEATURE:
<223> OTHER INFORMATION: Primer prom galP* rev

<400> SEQUENCE: 74
acgtcattgc cttgtttgac cgcccctgtt ttttagcgtc aggcatataa tacctcctaa    60
agttaaacaa aattatttgt ag                                            82

<210> SEQ ID NO 75
<211> LENGTH: 70
<212> TYPE: DNA
<213> ORGANISM: artificial sequence
<220> FEATURE:
<223> OTHER INFORMATION: Primer disruption k7 fw

<400> SEQUENCE: 75
ccgcccgcac aataacatca ttcttcctga tcacgtttca ccgcagatta gtgtaggctg    60
gagctgcttc                                                          70

<210> SEQ ID NO 76
<211> LENGTH: 47
<212> TYPE: DNA
<213> ORGANISM: artificial sequence
<220> FEATURE:
<223> OTHER INFORMATION: Primer disruption k7 rev

<400> SEQUENCE: 76
gatagggacg acgtggtgtt agctgtgcat atgaatatcc tccttag                 47

<210> SEQ ID NO 77
<211> LENGTH: 47
<212> TYPE: DNA
<213> ORGANISM: artificial sequence
<220> FEATURE:
<223> OTHER INFORMATION: Primer KHK-Cfw

<400> SEQUENCE: 77
ggatccgtcg acaggaggta acatatggaa gagaagcaga tcctgtg                 47

<210> SEQ ID NO 78
<211> LENGTH: 35
<212> TYPE: DNA
<213> ORGANISM: artificial sequence
<220> FEATURE:
<223> OTHER INFORMATION: Primer KHK-Crev

<400> SEQUENCE: 78
ctgcagtcta aagatctca cacgatgcca tcaaa                                35

<210> SEQ ID NO 79
<211> LENGTH: 44
<212> TYPE: DNA
<213> ORGANISM: artificial sequence
<220> FEATURE:
<223> OTHER INFORMATION: Primer AldoB_RBS_BaHI_F

<400> SEQUENCE: 79
ttggatccaa gaaggagaat tcatatggca catcgctttc cggc                     44

<210> SEQ ID NO 80
<211> LENGTH: 21
<212> TYPE: DNA
<213> ORGANISM: artificial sequence
<220> FEATURE:
<223> OTHER INFORMATION: Primer RevAldoB

<400> SEQUENCE: 80
ttaatacgtg taacaggccg t                                              21

<210> SEQ ID NO 81
<211> LENGTH: 101
<212> TYPE: DNA
<213> ORGANISM: artificial sequence
<220> FEATURE:
<223> OTHER INFORMATION: Primer iclR-fw3

<400> SEQUENCE: 81
cgcacccatt cccgcgaaac gcggcagaaa acccgccgtt gccaccgcac cagcgactgg    60
acaggttcag tctttaacgc gtgtaggctg gagctgcttc g                        101

<210> SEQ ID NO 82
<211> LENGTH: 100
<212> TYPE: DNA
<213> ORGANISM: artificial sequence
<220> FEATURE:
<223> OTHER INFORMATION: Primer iclR-rev2

<400> SEQUENCE: 82
gcgcattcca ccgtacgcca gcgtcacttc cttcgccgct taatcacca tcgcgccaaa     60 ctcggtcacg cggtcatcgg catatgaata tcctccttag                          100

<210> SEQ ID NO 83
<211> LENGTH: 63
<212> TYPE: DNA
<213> ORGANISM: artificial sequence
<220> FEATURE:
<223> OTHER INFORMATION: Primer fw tpi ycp

<400> SEQUENCE: 83
gaattgctgg cccgctgcgg cataaaaatt aattggtacc ggttatttaa actgtgagga    60
cct                                                                  63

<210> SEQ ID NO 84
<211> LENGTH: 46
<212> TYPE: DNA
<213> ORGANISM: artificial sequence
<220> FEATURE:
<223> OTHER INFORMATION: Primer Rev tpi

<400> SEQUENCE: 84
gatttgcttt tcttccattt ttagtttatg tatgtgtttt tttgta         46

<210> SEQ ID NO 85
<211> LENGTH: 40
<212> TYPE: DNA
<213> ORGANISM: artificial sequence
<220> FEATURE:
<223> OTHER INFORMATION: Primer Fw khk-C opt

<400> SEQUENCE: 85
cacatacata aactaaaaat ggaagaaaag caaatcttgt               40

<210> SEQ ID NO 86
<211> LENGTH: 45
<212> TYPE: DNA
<213> ORGANISM: artificial sequence
<220> FEATURE:
<223> OTHER INFORMATION: Primer Rev khk-C opt

<400> SEQUENCE: 86
gtttctgtct ttgcctttga tctgcttaaa cgataccgtc gaaac          45

<210> SEQ ID NO 87
<211> LENGTH: 42
<212> TYPE: DNA
<213> ORGANISM: artificial sequence
<220> FEATURE:
<223> OTHER INFORMATION: Primer Trk1 fw

<400> SEQUENCE: 87
ggtatcgttt aagcagatca aaggcaaaga cagaaaccgt ag             42

<210> SEQ ID NO 88
<211> LENGTH: 56
<212> TYPE: DNA
<213> ORGANISM: artificial sequence
<220> FEATURE:
<223> OTHER INFORMATION: Primer Term-trk1 rev

<400> SEQUENCE: 88
attcctatca ttatttacgt aatgacccat cttggtgtgt catcggtagt aacgcc    56

<210> SEQ ID NO 89
<211> LENGTH: 49
<212> TYPE: DNA
<213> ORGANISM: artificial sequence
<220> FEATURE:
<223> OTHER INFORMATION: Primer pFba1 fw

<400> SEQUENCE: 89
ccgatgacac accaagatgg gtcattacgt aaataatgat aggaatggg       49

<210> SEQ ID NO 90
<211> LENGTH: 45
<212> TYPE: DNA
<213> ORGANISM: artificial sequence
<220> FEATURE:
<223> OTHER INFORMATION: Primer pfab1 rev

```
<400> SEQUENCE: 90
gctgggaatc tgtgagccat tttgaatatg tattacttgg ttatg            45

<210> SEQ ID NO 91
<211> LENGTH: 42
<212> TYPE: DNA
<213> ORGANISM: artificial sequence
<220> FEATURE:
<223> OTHER INFORMATION: Primer aldoB opt fw

<400> SEQUENCE: 91
tgatctacga tcagaattta gtaagtgtaa caagcagtga ac               42

<210> SEQ ID NO 92
<211> LENGTH: 42
<212> TYPE: DNA
<213> ORGANISM: artificial sequence
<220> FEATURE:
<223> OTHER INFORMATION: Primer aldoB opt rev

<400> SEQUENCE: 92
gtaatacata ttcaaaatgg ctcacagatt cccagctttg ac               42

<210> SEQ ID NO 93
<211> LENGTH: 49
<212> TYPE: DNA
<213> ORGANISM: artificial sequence
<220> FEATURE:
<223> OTHER INFORMATION: Primer tlk1 fw

<400> SEQUENCE: 93
gcttgttaca cttactaaat tctgatcgta gatcatcaga tttgatatg         49

<210> SEQ ID NO 94
<211> LENGTH: 66
<212> TYPE: DNA
<213> ORGANISM: artificial sequence
<220> FEATURE:
<223> OTHER INFORMATION: Primer rev tlk1 ycp

<400> SEQUENCE: 94
ggtgacccgg cggggacgag gcaagctaaa cagatctcta gaataatttt ttatattctt   60
tattgg                                                              66

<210> SEQ ID NO 95
<211> LENGTH: 25
<212> TYPE: DNA
<213> ORGANISM: artificial sequence
<220> FEATURE:
<223> OTHER INFORMATION: Primer fw deletion xks1

<400> SEQUENCE: 95
gagattttgt tcttctgagc ttctg                                  25

<210> SEQ ID NO 96
<211> LENGTH: 25
<212> TYPE: DNA
<213> ORGANISM: artificial sequence
<220> FEATURE:
<223> OTHER INFORMATION: Primer rev deletion xks1

<400> SEQUENCE: 96
gaaattgcac ttagcatttt tgaat                                  25
```

<210> SEQ ID NO 97
<211> LENGTH: 897
<212> TYPE: DNA
<213> ORGANISM: Saccharomyces cerevisiae

<400> SEQUENCE: 97

```
atggaagaaa agcaaatctt gtgtgttggt ttggttgttt tggacgttat ctctttggtt      60
gacaagtacc caaaggaaga ctctgaaatc agatgtttgt ctcaaagatg gcaagaggt     120
ggtaacgctt ctaactcttg tactgttttg tctttgttgg gtgctccatg tgctttcatg     180
ggttctatgg ctccaggtca cgttgctgac ttcttggttg ctgacttcag aaggagaggt     240
gttgacgttt ctcaagttgc ttggcaatct aagggtgaca ctccatcttc ttgttgtatc     300
atcaacaact ctaacggtaa cagaactatc gttttgcacg acacttcttt gccagacgtt     360
tctgctactg acttcgaaaa ggttgacttg actcaattca gtggatcca catcgaaggt     420
agaaacgctt ctgaacaagt taagatgttg caaagaatcg acgctcacaa cactagacaa     480
ccaccagaac aaaagatcag agtttctgtt gaagttgaaa agccaagaga agaattgttc     540
caattgttcg gttacggtga cgttgttttc gtttctaagg acgttgctaa gcacttgggt     600
ttccaatctg ctgaagaagc tttgagaggt ttgtacggta gagttagaaa gggtgctgtt     660
ttggtttgtg cttgggctga agaaggtgct gacgctttgg gtccagacgg taagttgttg     720
cactctgacg ctttcccacc gccaagagtt gttgacactt gggtgctgg tgacactttc     780
aacgcttctg ttatcttctc tttgtctcaa ggtagatctg ttcaagaagc tttgagattc     840
ggttgtcaag ttgctggtaa gaagtgtggt ttgcaaggtt tcgacggtat cgtttaa       897
```

<210> SEQ ID NO 98
<211> LENGTH: 1095
<212> TYPE: DNA
<213> ORGANISM: saccharomyces cerevisiae

<400> SEQUENCE: 98

```
atggctcaca gattcccagc tttgactcaa gaacaaaaga aggaattgtc tgaaatcgct      60
caatctatcg ttgctaacgg taagggtatc ttggctgctg acgaatctgt tggtactatg     120
ggtaacagat tgcaaagaat caaggttgaa acactgaag aaaacagaag acaattcaga     180
gaaatcttgt ctctgttga ctcttctatc aaccaatcta tcggtggtgt tatcttgttc     240
cacgaaactt tgtaccaaaa ggactctcaa ggtaagttgt tcagaaacat cttgaaggaa     300
aagggtatcg ttgttggtat caagttggac caaggtggtg ctccattggc tggtactaac     360
aaggaaacta ctatccaagg tttggacggt ttgtctgaaa gatgtgctca atacaagaag     420
gacggtgttg acttcggtaa gtggagagct gttttgagaa tcgctgacca atgtccatct     480
tctttggcta tccaagaaaa cgctaacgct ttggctagat acgcttctat ctgtcaacaa     540
aacggtttgg ttccaatcgt tgaaccagaa gttatcccag acggtgacca cgacttggaa     600
cactgtcaat acgttactga aaaggttttg gctgctgttt acaaggcttt gaacgaccac     660
cacgtttact tggaaggtac tttgttgaag ccaaacatgg ttactgctgg tcacgcttgt     720
actaagaagt acactccaga acaagttgct atggctactg ttactgcttt gcacagaact     780
gttccagctg ctgttccagg tatctgtttc ttgtctggtg gtatgtctga agaagacgct     840
actttgaact tgaacgctat caacttgtgt ccattgccaa agccatggaa gttgtctttc     900
tcttacggta gagctttgca agcttctgct ttggctgctt ggggtggtaa ggctgctaac     960
aaggaagcta ctcaagaagc tttcatgaag agagctatgg ctaactgtca agctgctaag    1020
```

```
ggtcaatacg ttcacactgg ttcttctggt gctgcttcta ctcaatcttt gttcactgct    1080
tgttacactt actaa                                                      1095

<210> SEQ ID NO 99
<211> LENGTH: 10023
<212> TYPE: DNA
<213> ORGANISM: Saccharomyces cerevisiae

<400> SEQUENCE: 99
ggtaccttta cgatagagcc agagacgatg ccgacgaaga tgaagaagat cccgacacaa      60
gaagctccgg taagaagaag gacgccagcc aagaagaatc tctaatctaa gaggacggtt     120
gctgaagaaa aaggctttt ttattttgtc cgtttttttt ttgtaaaacc caaagatctg     180
aatctaaagc ttttttaaac gtatatagat gtcacatgt gtgttttgt ttttttacgt      240 acgtataccc acctatatat gcataatccg taattgaaaa aaaaaaaga aaaagatcaa     300 ggaacacatc accctgggca catcaagcgt gaggaatgcc gtccaactgg tggagacgct     360
tgatttgctc ttttttgttct gggtccaacc cggtctcgaa gaacatcagc accacgcccg     420
caacgacaaa gaacattgca atacacttgc atatgtgagc atagtcgagc ggtccgttct     480
gtggttgatg ctgttgttct ttcttctgtt tgtcaggggt gatagccata tcttcgtgct     540
cttgttgcga ttgttctgtt ccatctgcac cagaacaaag aacaaagaa caaggaacaa     600 agtccaagca cgtcagcgct gtttataagg ggattgacga gggatcgggc ctagagtgcc     660
agcgcgccag ggagagggag ccccctgggc cctcatccgc aggctgatag gggtcaccccc    720 gctgggcagg tcagggcagg ggctctcagg ggggcgccat ggacaaactg cactgaggtt     780
ctaagacaca tgtattattg tgagtatgta tatatagaga gagattaagg cgtacagccg     840
ggtggtagag attgattaac ttggtagtct tatcttgtca attgagtttc tgtcagtttc     900
ttcttgaaca agcacgcagc taagtaagca acaaagcagg ctaacaaact aggtactcac     960
atacagactt attaagacat agaactatga ctacggataa cgctaaggcg caactgacct    1020
cgtcttcagg gggtaacatt attgtggtgt ccaacaggct tcccgtgaca atcactaaaa    1080
acagcagtac gggacagtac gagtacgcaa tgtcgtccgg agggctggtc acggcgttgg    1140
aagggttgaa gaagacgtac actttcaagt ggttcggatg gcctgggcta gagattcctg    1200
acgatgagaa ggatcaggtg aggaaggact tgctggaaaa gtttaatgcc gtacccatct    1260
tcctgagcga tgaaatcgca gacttacact acaacgggtt cagtaattct attctatggc    1320
cgttattcca ttaccatcct ggtgagatca atttcgacga gaatgcgtgg ttggcataca    1380
acgaggcaaa ccagacgttc accaacgaga ttgctaagac tatgaaccat aacgatttaa    1440
tctgggtgca tgattaccat ttgatgttgg ttccggaaat gttgagagtc aagattcacg    1500
agaagcaact gcaaaacgtt aaggtcgggt ggttcctgca cacaccattc ccttcgagtg    1560 aaattacag aatcttacct gtcagacaag agatttgaa gggtgttttg agttgtgatt    1620
tagtcgggtt ccacacatac gattatgcaa gacatttctt gtcttccgtg caaagagtgc    1680
ttaacgtgaa cacattgcct aatggggtgg aataccaggg cagattcgtt aacgtagggg    1740
ccttccctat cggtatcgac gtggacaagt tcaccgatgg gttgaaaaag gaatccgtac    1800
aaaagagaat ccaacaattg aaggaaactt caagggctg caagatcata gttggtgtcg    1860
acaggctgga ttcatcaaa ggtgtgcctc agaagttgca cgccatggaa gtgtttctga    1920
acgagcatcc agaatggagg ggcaaggttg ttctggtaca ggttgcagtg ccaagtcgtg    1980
```

```
gagatgtgga agagtaccaa tatttaagat ctgtggtcaa tgagttggtc ggtagaatca    2040
acggtcagtt cggtactgtg gaattcgtcc ccatccattt catgcacaag tctataccat    2100
ttgaagagct gatttcgtta tatgctgtga gcgatgtttg tttggtctcg tccacccgtg    2160
atggtatgaa cttggtttcc tacgaatata ttgcttgcca agaagaaaag aaaggttcct    2220
taatcctgag tgagttcaca ggtgccgcac aatccttgaa tggtgctatt attgtaaatc    2280
cttggaacac cgatgatctt tctgatgcca tcaacgaggc cttgactttg cccgatgtaa    2340
agaaagaagt taactgggaa aaactttaca aatacatctc taaatacact tctgccttct    2400
ggggtgaaaa tttcgtccat gaattataca gtacatcatc aagctcaaca agctcctctg    2460
ccaccaaaaa ctgatgaacc cgatgcaaat gagacgatcg tctattcctg gtccggtttt    2520
ctctgccctc tcttctattc acttttttta tactttatat aaaattatat aaatgacata    2580
actgaaacgc cacacgtcct ctcctattcg ttaacgcctg tctgtagcgc tgttactgaa    2640
gctgcgcaag tagttttttc accgtatagg atgacaaccc ttaatataac ttcgtataat    2700
gtatgctata cgaagttatt aggtctagag atctgtttag cttgcctcgt cccgccgggg    2760
tcacccggcc agcgacatgg aggcccagaa taccctcctt gacagtcttg acgtgcgcag    2820 ctcagggggca tgatgtgact gtcgcccgta catttagccc atacatcccc atgtataatc    2880
atttgcatcc atacatttg atggccgcac ggcgcgaagc aaaaattacg gctcctcgct    2940
gcagacctgc gagcagggaa acgctcccct cacagacgcg ttgaattgtc cccacgccgc    3000
gcccctgtag agaaatataa aaggttagga tttgccactg aggttcttct ttcatatact    3060
tccttttaaa atcttgctag gatacagttc tcacatcaca tccgaacata aacaaccatg    3120
ggtaaggaaa agactcacgt ttcgaggccg cgattaaatt ccaacatgga tgctgattta    3180
tatgggtata aatgggctcg cgataatgtc gggcaatcag gtgcgacaat ctatcgattg    3240
tatgggaagc ccgatgcgcc agagttgttt ctgaaacatg gcaaaggtag cgttgccaat    3300
gatgttacag atgagatggt cagactaaac tggctgacgg aatttatgcc tcttccgacc    3360
atcaagcatt ttatccgtac tcctgatgat gcatggttac tcaccactgc gatccccggc    3420
aaaacagcat tccaggtatt agaagaatat cctgattcag gtgaaaatat tgttgatgcg    3480
ctggcagtgt tcctgcgccg gttgcattcg attcctgttt gtaattgtcc ttttaacagc    3540
gatcgcgtat ttcgtctcgc tcaggcgcaa tcacgaatga ataacggttt ggttgatgcg    3600
agtgattttg atgacgagcg taatggctgg cctgttgaac aagtctggaa agaaatgcat    3660
aagcttttgc cattctcacc ggattcagtc gtcactcatg gtgatttctc acttgataac    3720 cttattttg acgaggggaa attaataggt tgtattgatg ttggacgagt cggaatcgca    3780
gaccgatacc aggatcttgc catcctatgg aactgcctcg gtgagttttc tccttcatta    3840
cagaaacggc ttttttcaaaa atatggtatt gataatcctg atatgaataa attgcagttt    3900
catttgatgc tcgatgagtt tttctaatca gtactgacaa taaaaagatt cttgttttca    3960
agaacttgtc atttgtatag tttttttata ttgtagttgt tctatttaa tcaaatgtta    4020 gcgtgattta tatttttttt cgcctcgaca tcatctgccc agatgcgaag ttaagtgcgc    4080
agaaagtaat atcatgcgtc aatcgtatgt gaatgctggt cgctatactg ctgtcgattc    4140
gatactaacg ccgccatcca gtgtcgaaaa cgagctctcg agaacccttaa atataacttc    4200 gtataatgta tgctatacga agttattagg tgatatcgga tccggatcct cagcagcgaa    4260
acgttgttct gggaaaccat ggagaaactg aaagcgcttg cgccagctc gattctggta    4320 ctgccgatcg agaagatgat ggagtgagca tgcaagcttg gcgtaatcat ggtcatagct    4380
```

```
gtttcctgtg tgaaattgtt atccgctcac aattccacac aacatacgag ccggaagcat    4440
aaagtgtaaa gcctggggtg cctaatgagt gagctaactc acattaattg cgttgcgctc    4500
actgcccgct ttccagtcgg gaaacctgtc gtgccagctg cattaatgaa tcggccaacg    4560
cgcggggaga ggcggtttgc gtattgggcg ctcttccgct tcctcgctca ctgactcgct    4620
gcgctcggtc gttcggctgc ggcgagcggt atcagctcac tcaaaggcgg taatacggtt    4680
atccacagaa tcaggggata acgcaggaaa gaacatgtga gcaaaaggcc agcaaaaggc    4740
caggaaccgt aaaaaggccg cgttgctggc gtttttccat aggctccgcc cccctgacga    4800
gcatcacaaa aatcgacgct caagtcagag gtggcgaaac ccgacaggac tataaagata    4860
ccaggcgttt ccccctggaa gctccctcgt gcgctctcct gttccgaccc tgccgcttac    4920
cggatacctg tccgcctttc tcccttcggg aagcgtggcg ctttctcata gctcacgctg    4980
taggtatctc agttcggtgt aggtcgttcg ctccaagctg ggctgtgtgc acgaaccccc    5040
cgttcagccc gaccgctgcg ccttatccgg taactatcgt cttgagtcca acccggtaag    5100
acacgactta tcgccactgg cagcagccac tggtaacagg attagcagag cgaggtatgt    5160
aggcggtgct acagagttct tgaagtggtg gcctaactac ggctacacta aggacagt     5220 atttggtatc tgcgctctgc tgaagccagt taccttcgga aaaagagttg gtagctcttg    5280
atccggcaaa caaaccaccg ctggtagcgg tggttttttt gtttgcaagc agcagattac    5340
gcgcagaaaa aaaggatctc aagaagatcc tttgatcttt tctacggggt ctgacgctca    5400
gtggaacgaa aactcacgtt aagggatttt ggtcatgaga ttatcaaaaa ggatcttcac    5460
ctagatcctt ttaaattaaa aatgaagttt taaatcaatc taaagtatat atgagtaaac    5520
ttggtctgac agttaccaat gcttaatcag tgaggcacct atctcagcga tctgtctatt    5580
tcgttcatcc atagttgcct gactccccgt cgtgtagata actacgatac gggagggctt    5640
accatctggc cccagtgctg caatgatacc gcgagaccca cgctcaccgg ctccagattt    5700
atcagcaata accagccagc cggaagggc cgagcgcaga agtggtcctg caactttatc    5760
cgcctccatc cagtctatta attgttgccg ggaagctaga gtaagtagtt cgccagttaa    5820
tagtttgcgc aacgttgttg ccattgctac aggcatcgtg gtgtcacgct cgtcgtttgg    5880
tatggcttca ttcagctccg gttcccaacg atcaaggcga gttacatgat cccccatgtt    5940
gtgcaaaaaa gcggttagct ccttcggtcc tccgatcgtt gtcagaagta agttggccgc    6000
agtgttatca ctcatggtta tggcagcact gcataattct cttactgtca tgccatccgt    6060
aagatgcttt tctgtgactg gtgagtactc aaccaagtca ttctgagaat agtgtatgcg    6120
gcgaccgagt tgctcttgcc cggcgtcaat acgggataat accgcgccac atagcagaac    6180
tttaaaagtg ctcatcattg gaaaacgttc ttcggggcga aaactctcaa ggatcttacc    6240
gctgttgaga tccagttcga tgtaacccac tcgtgcaccc aactgatctt cagcatcttt    6300
tactttcacc agcgtttctg ggtgagcaaa aacaggaagg caaaatgccg caaaaaaggg    6360
aataagggcg acacggaaat gttgaatact catactcttc ctttttcaat attattgaag    6420
catttatcag ggttattgtc tcatgagcgg atacatattt gaatgtattt agaaaaataa    6480
acaaataggg gttccgcgca catttccccg aaaagtgcca cctgacgtct aagaaaccat    6540
tattatcatg acattaacct ataaaaatag gcgtatcacg aggccctttc gtcttcaaga    6600
attagctttt caattcaatt catcatttttt ttttattct ttttttttgat ttcggtttct    6660 ttgaaatttt tttgattcgg taatctccga acagaaggaa gaacgaagga aggagcacag    6720
```

```
acttagattg gtatatatac gcatatgtag tgttgaagaa acatgaaatt gcccagtatt   6780
cttaacccaa ctgcacagaa caaaaacatg caggaaacga agataaatca tgtcgaaagc   6840
tacatataag gaacgtgctg ctactcatcc tagtcctgtt gctgccaagc tatttaatat   6900
catgcacgaa aagcaaacaa acttgtgtgc ttcattggat gttcgtacca ccaaggaatt   6960
actggagtta gttgaagcat taggtcccaa aatttgttta ctaaaaacac atgtggatat   7020
cttgactgat ttttccatgg agggcacagt taagccgcta aaggcattat ccgccaagta   7080
caatttttta ctcttcgaag acagaaaatt tgctgacatt ggtaatacag tcaaattgca   7140
gtactctgcg ggtgtataca gaatagcaga atgggcagac attacgaatg cacacggtgt   7200
ggtgggccca ggtattgtta gcggtttgaa gcaggcggca gaagaagtaa caaaggaacc   7260
tagaggcctt ttgatgttag cagaattgtc atgcaagggc tccctatcta ctggagaata   7320
tactaagggt actgttgaca ttgcgaagag cgacaaagat tttgttatcg gctttattgc   7380
tcaaagagac atgggtggaa gagatgaagg ttacgattgg ttgattatga cacccggtgt   7440
gggtttagat gacaagggag acgcattggg tcaacagtat agaaccgtgg atgatgtggt   7500
ctctacagga tctgacatta ttattgttgg aagaggacta tttgcaaagg gaagggatgc   7560
taaggtagag ggtgaacgtt acagaaaagc aggctgggaa gcatatttga gaagatgcgg   7620
ccagcaaaac taaaaaactg tattataagt aaatgcatgt atactaaact cacaaattag   7680
agcttcaatt taattatatc agttattacc caattctcat gtttgacagc ttatcatcga   7740
tcgtccaact gcatggagat gagtcgtggc aagaatacca agagttcctc ggtttgccag   7800
ttattaaaag actcgtattt ccaaaagact gcaacatact actcagtgca gcttcacaga   7860
aacctcattc gtttattccc ttgtttgatt cagaagcagg tgggacaggt gaacttttgg   7920
attggaactc gatttctgac tgggttggaa ggcaagagag ccccgagagc ttacatttta   7980
tgttagctgg tggactgacg ccagaaaatg ttggtgatgc gcttagatta aatggcgtta   8040
ttggtgttga tgtaagcgga ggtgtggaga caaatggtgt aaaagactct aacaaaatag   8100
caaatttcgt caaaaatgct aagaaatagg ttattactga gtagtattta tttaagtatt   8160
gtttgtgcac ttgcctgcaa gccttttgaa aagcaagcat aaaagatcta aacataaaat   8220
ctgtaaaata caagatgta aagataatgc taaatcattt ggcttttga ttgattgtac   8280
aggaaaatat acatcgcagg gggttgactt ttaccatttc accgcaatgg aatcaaactt   8340
gttgaagaga atgttcacag gcgcatacgc tacaatgacc cgattcttgc tagccttttc   8400
tcggtcttgc aaacaaccgc cggcagctta gtatataaat acacatgtac atacctctct   8460
ccgtatcctc gtaatcattt tcttgtattt atcgtctttt cgctgtaaaa actttatcac   8520
acttatctca aatacactta ttaaccgctt ttactattat cttctacgct gacagtaata   8580
tcaaacagtg acacatatta aacacagtgg tttctttgca taaacaccat cagcctcaag   8640
tcgtcaagta aagatttcgt gttcatgcag atagataaca atctatatgt tgataattag   8700
cgttgcctca tcaatgcgag atccgtttaa ccggacccta gtgcacttac cccacgttcg   8760
gtccactgtg tgccgaacat gctccttcac tattttaaca tgtggaatta attctcatgt   8820
ttgacagctt atcatcgaac tctaagaggt gatacttatt tactgtaaaa ctgtgacgat   8880
aaaccggaa ggaagaataa gaaaactcga actgatctat aatgcctatt ttctgtaaag   8940
agtttaagct atgaaagcct cggcattttg gccgctccta ggtagtgctt ttttcaag   9000
gacaaaacag tttctttttc ttgagcaggt tttatgtttc ggtaatcata acaataaat   9060
aaattatttc atttatgttt aaaaataaaa aataaaaaag tatttaaat ttttaaaaaa   9120
```

| | | | |
|---|---|---|---|
| gttgattata | agcatgtgac | cttttgcaag caattaaatt | ttgcaatttg tgattttagg | 9180 |
| caaaagttac | aatttctggc | tcgtgtaata tatgtatgct | aaagtgaact tttacaaagt | 9240 |
| cgatatggac | ttagtcaaaa | gaaattttct taaaaatata | tagcactagc caatttagca | 9300 |
| cttctttatg | agatatatta | tagacttat taagccagat | ttgtgtatta tatgtattta | 9360 |
| cccggcgaat | catggacata | cattctgaaa taggtaatat | tctctatggt gagacagcat | 9420 |
| agataaccta | ggatacaagt | taaaagctag tactgttttg | cagtaatttt tttctttttt | 9480 |
| ataagaatgt | taccacctaa | ataagttata aagtcaatag | ttaagtttga tatttgattg | 9540 |
| taaaataccg | taatatattt | gcatgatcaa aaggctcaat | gttgactagc cagcatgtca | 9600 |
| accactatat | tgatcaccga | tatggact tccacaccaa | ctagtaatat gacaataaat | 9660 |
| tcaagatatt | cttcatgaga | atggcccagc gatatatgcg | gtgtgaaata ccgcacagat | 9720 |
| gcgtaaggag | aaaataccgc | atcaggcgcc attcgccatt | caggctgcgc aactgttggg | 9780 |
| aagggcgatc | ggtgcgggcc | tcttcgctat tacgccagct | ggcgaaaggg ggatgtgctg | 9840 |
| caaggcgatt | aagttgggta | acgccagggt tttcccagtc | acgacgttgt aaaacgacgg | 9900 |
| ccagtgaatt | cgagctcatg | ttagacaaca cccgcttacg | catagctatt cagaaatcag | 9960 |
| gccgtttaag | cgatgattca | cgagaattgc tggcccgctg | cggcataaaa attaattggt | 10020 |
| acc | | | | 10023 |

<210> SEQ ID NO 100
<211> LENGTH: 1701
<212> TYPE: DNA
<213> ORGANISM: Saccharomyces cerevisiae

<400> SEQUENCE: 100

| | | | |
|---|---|---|---|
| atggcgattg | caattggcct | cgattttggc agtgattctg | tgcgagcttt ggcggtggac | 60 |
| tgcgctaccg | gtgaagagat | cgccaccagc gtagagtggt | atcccgttg gcagaaaggg | 120 |
| caattttgtg | atgccccgaa | taaccagttc cgtcatcatc | cgcgtgacta cattgagtca | 180 |
| atggaagcgg | cactgaaaac | cgtgcttgca gagcttagcg | tcgaacagcg cgcagctgtg | 240 |
| gtcgggattg | gcgttgacag | taccggctcg acgcccgcac | cgattgatgc cgacggaaac | 300 |
| gtgctggcgc | tgcgcccgga | gtttgccgaa acccgaacg | cgatgttcgt attgtggaaa | 360 |
| gaccacactg | cggttgaaga | gcggaagag attacccgtt | tgtgccacgc gccgggcaac | 420 |
| gttgactact | cccgctacat | tggtggtatt tattccagcg | aatggttctg gcaaaaatc | 480 |
| ctgcatgtga | ctcgccagga | cagcgccgtg gcgcaatctg | ccgcatcgtg gattgagctg | 540 |
| tgcgactggg | tgccagctct | gctttccggt accacccgcc | cgcaggatat tcgtcgcgga | 600 |
| cgttgcagcg | ccgggcataa | atctctgtgg cacgaaagct | ggggcggcct gccgccagcc | 660 |
| agtttctttg | atgagctgga | cccgatcctc aatcgccatt | gccttccc gctgttcact | 720 |
| gacacttgga | ctgccgatat | tccggtgggc accttatgcc | cggaatgggc gcagcgtctc | 780 |
| ggcctgcctg | aaagcgtggt | gatttccggc ggcgcgtttg | actgccatat gggcgcagtt | 840 |
| ggcgcaggcg | cacagcctaa | cgcactggta aaagttatcg | gtacttccac ctgcgacatt | 900 |
| ctgattgccg | acaaacagag | cgttggcgag cgggcagtta | aggtatttg cggtcaggtt | 960 |
| gatggcagcg | tggtgcctgg | atttatcggt ctggaagcag | gccaatcggc gtttggtgat | 1020 |
| atctacgcct | ggtttggtcg | cgtactcggc tggcgctgg aacagcttgc | cgcccagcat | 1080 |
| ccggaactga | aaacgcaaat | caacgccagc cagaaacaac | tgcttccggc gctgaccgaa | 1140 |

-continued

| | |
|---|---|
| gcatgggcca aaaatccgtc tctggatcac ctgccggtgg tgctcgactg gtttaacggc | 1200 |
| cgccgcacac cgaacgctaa ccaacgcctg aaagggtga ttaccgatct taacctcgct | 1260 |
| accgacgctc cgctgctgtt cggcggtttg attgctgcca ccgcctttgg cgcacgcgca | 1320 |
| atcatggagt gctttaccga tcaggggatc gccgttaata acgtgatggc actgggcggc | 1380 |
| atcgcgcgga aaaccaggt cattatgcag gcctgctgcg acgtgctgaa tcgcccgctg | 1440 |
| caaattgttg cctctgacca gtgctgtgcg ctcggtgcgg cgattttgc tgccgtcgcc | 1500 |
| gcgaaagtgc acgcagacat cccatcagct cagcaaaaaa tggccagtgc ggtagagaaa | 1560 |
| accctgcaac cgtgcagcga gcaggcacaa cgctttgaac agctttatcg ccgctatcag | 1620 |
| caatgggcga tgagcgccga acaacactat cttccaactt ccgccccggc acaggctgcc | 1680 |
| caggccgttg cgactctata a | 1701 |

<210> SEQ ID NO 101
<211> LENGTH: 1803
<212> TYPE: DNA
<213> ORGANISM: Saccharomyces cerevisiae

<400> SEQUENCE: 101

| | |
|---|---|
| atgttgtgtt cagtaattca gagacagaca agagaggttt ccaacacaat gtctttagac | 60 |
| tcatactatc ttgggtttga tctttcgacc caacaactga aatgtctcgc cattaaccag | 120 |
| gacctaaaaa ttgtccattc agaaacagtg gaatttgaaa aggatcttcc gcattatcac | 180 |
| acaaagaagg gtgtctatat acacggcgac actatcgaat gtcccgtagc catgtggtta | 240 |
| gaggctctag atctggttct ctcgaaatat cgcgaggcta aatttccatt gaacaaagtt | 300 |
| atggccgtct cagggtcctg ccagcagcac gggtctgtct actggtcctc ccaagccgaa | 360 |
| tctctgttag agcaattgaa taagaaaccg gaaaagatt tattgcacta cgtgagctct | 420 |
| gtagcatttg caaggcaaac cgcccccaat tggcaagacc acagtactgc aaagcaatgt | 480 |
| caagagtttg aagagtgcat aggtgggcct gaaaaaatgg ctcaattaac agggtccaga | 540 |
| gcccatttta gatttactgg tcctcaaatt ctgaaaattg cacaattaga accagaagct | 600 |
| tacgaaaaaa caaagaccat ttctttagtg tctaattttt tgacttctat cttagtgggc | 660 |
| catcttgttg aattagagga ggcagatgcc tgtggtatga acctttatga tatacgtgaa | 720 |
| agaaaattca gtgatgagct actacatcta attgatagtc cttctaagga taaaactatc | 780 |
| agacaaaaat taatgagagc acccatgaaa aatttgatag cgggtaccat ctgtaaatat | 840 |
| tttattgaga agtacggttt caatacaaac tgcaaggtct ctcccatgac tggggataat | 900 |
| ttagccacta tatgttcttt accccctgcgg aagaatgacg ttctcgtttc cctaggaaca | 960 |
| agtactacag ttcttctggt caccgataag tatcacccct ctccgaacta tcatcttttc | 1020 |
| attcatccaa ctctgccaaa ccattatatg ggtatgattt gttattgtaa tggttctttg | 1080 |
| gcaagggaga ggataagaga cgagttaaac aaagaacggg aaaataatta tgagaagact | 1140 |
| aacgattgga ctcttttaa tcaagctgtg ctagatgact cagaaagtag tgaaaatgaa | 1200 |
| ttaggtgtat attttcctct gggggagatc gttcctagcg taaaagccat aaacaaaagg | 1260 |
| gttatcttca atccaaaaac gggtatgatt gaaagagagg tggccaagtt caaagacaag | 1320 |
| aggcacgatg ccaaaaatat tgtagaatca caggctttaa gttgcagggt aagaatatct | 1380 |
| cccctgcttt cggattcaaa cgcaagctca caacagagac tgaacgaaga tacaatcgtg | 1440 |
| aagtttgatt acgatgaatc tccgctgcgg gactacctaa ataaaggcc agaaaggact | 1500 |
| ttttttgtag gtgggcttc taaaaacgat gctattgtga agaagtttgc tcaagtcatt | 1560 |

```
ggtgctacaa agggtaattt taggctagaa acaccaaact catgtgccct tggtggttgt    1620
tataaggcca tgtggtcatt gttatatgac tctaataaaa ttgcagttcc ttttgataaa    1680
tttctgaatg acaattttcc atggcatgta atggaaagca tatccgatgt ggataatgaa    1740
aattgggatc gctataattc caagattgtc cccttaagcg aactggaaaa gactctcatc    1800
taa                                                                  1803

<210> SEQ ID NO 102
<211> LENGTH: 160
<212> TYPE: DNA
<213> ORGANISM: Saccharomyces cerevisiae

<400> SEQUENCE: 102
ttctagagca cagctaacac cacgtcgtcc ctatctgctg ccctaggtct atgagtggtt      60
gctggataac tttacgggca tgcataaggc tcgtataata tattcaggga gaccacaacg     120
gtttccctct acaaataatt ttgtttaact tttactagag                            160
```